(12) United States Patent
Lohray et al.

(10) Patent No.: US 6,987,123 B2
(45) Date of Patent: Jan. 17, 2006

(54) HETEROCYCLIC COMPOUNDS, THEIR PREPARATION, PHARMACEUTICAL COMPOSITIONS CONTAINING THEM AND THEIR USE IN MEDICINE

(75) Inventors: Braj Bhushan Lohray, Gujarat (IN); Vidya Bhushan Lohray, Gujarat (IN); Vijay Kumar Gajubhai Barot, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 333 days.

(21) Appl. No.: 09/928,242

(22) Filed: Aug. 10, 2001

(65) Prior Publication Data

US 2003/0199498 A1 Oct. 23, 2003

(51) Int. Cl.
*A61K 31/40* (2006.01)
*C07D 207/327* (2006.01)
*C07D 207/333* (2006.01)

(52) U.S. Cl. .................... 514/423; 514/427; 548/540; 548/562

(58) Field of Classification Search ........... 514/427, 514/423; 548/562, 540
See application file for complete search history.

(56) References Cited

U.S. PATENT DOCUMENTS 6,077,963 A * 6/2000 Gage et al.

* cited by examiner

*Primary Examiner*—Joseph K. McKane
*Assistant Examiner*—Sonya Wright
(74) *Attorney, Agent, or Firm*—Steven J. Moore

(57) ABSTRACT

The present invention relates to compounds of the general formula (I),

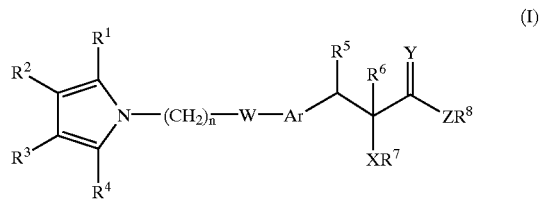

there derivatives, their analogs, their tautomeric forms, their stereoisomers, their polymorphs, their pharmaceutically acceptable salts, and their pharmaceutically acceptable solvates, wherein all variables are as defined in the specification.

21 Claims, No Drawings

HETEROCYCLIC COMPOUNDS, THEIR PREPARATION, PHARMACEUTICAL COMPOSITIONS CONTAINING THEM AND THEIR USE IN MEDICINE

FIELD OF INVENTION

The present invention relates to novel hypolipidaemic and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-substituted propanoic acids of the general formula (I), their derivatives, their analogs, their tautomeric forms, their stereoisomers, their polyinorphs, their pharmaceutically acceptable salts, their pharmaceutically acceptable solvates, pharmaceutical compositions containing them, use of these compounds in medicine and the intermediates involved in their preparation.

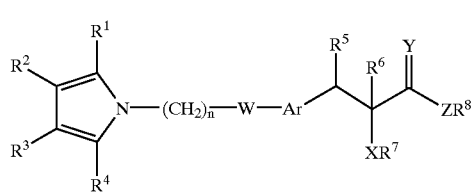

(I)

The present invention also relates to a process for the preparation of the above said novel compounds, their derivatives, their analogs, their tautomeric forms, their stereoisomers, their polymorphs, their pharmaceutically acceptable salts, their pharmaceutically acceptable solvates, and pharmaceutical compositions containing them.

The compounds of general formula (I) are useful in lowering elevated levels of cholesterol (TC), low-density lipoproteins (LDL), triglycerides, free fatty acids, glucose, insulin and the like; while increasing high-density lipoproteins, which results in beneficial effect in the mammals.

The compounds of the general formula (D) lower or modulate triglyceride levels and/or cholesterol levels and/or low-density lipoproteins (LDL) and raise HDL plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders. These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such, as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

The compounds of the present invention can be useful as aldose reductase inhibitors; for improving cognitive functions in dementia, and in the treatment and/or prophylaxis of disorders such as psoriasis, polycystic ovarian syndrome (PCOS), cancer, osteoporosis, leptin resistance, inflammation and inflammatory bowel diseases, xanthoma, pancreatitis, myotonic dystrophy, endothelial cell dysfunction and hyperlipidemia.

The compounds of the present invention are useful in the treatment of the diseases mentioned herein, alone or in combination one or more hypoglycemic, antihyperglycemic, hypolipidaemic, hypolipoproteinemic agents, antioxidants, antihypertensives, such as HMG CoA reductase inhibitor, fibrate, statins, glitazones, sulfonyl ureas, insulin, α-glycosidase inhibitors, nicotinic acid, cholestyramine, cholestipol or probucol, and the like.

BACKGROUND OF THE INVENTION

Hyperlipidaemia has been recognized as the major risk factor in causing cardiovascular diseases due to atherosclerosis. Atherosclerosis and other such peripheral vascular diseases affect the quality of life of a large population in the world. The emphasis during the therapy is laid on lowering the elevated plasma LDL cholesterol, low-density lipoprotein and plasma triglycerides in order to prevent or reduce the risk of occurrence of cardiovascular diseases. The details of etiology in atherosclerosis and coronary artery diseases is discussed by Ross and Glomset [New Engl. J. Med., 295, 369–377 (1976)]. Plasma cholesterol is generally esterified with various serum lipoproteins and numerous studies suggest an inverse relation between serum HDL-cholesterol level and risk for occurrence of cardiovascular disease. Many studies have suggests an increased risk of coronary artery diseases (CAD) due to elevated LDL and VLDL-cholesterol levels [Stampfer et al., N. Engl. J. Med., 325, 373–381(1991)]. The other studies illustrate protective effects of HDL against progression of atherosclerosis. Thus, HDL has become a crucial factor in treating diseases with increased levels of cholesterol [Miller et. al., Br. Med. J. 282, 1741–1744(1981); Picardo et al., Arteriosclerosis, 6, 434–441 (1986); Macikinnon et al., J. Biol. Chem. 261, 2548–2552 (1986)].

Diabetes is associated with a number of complications and also affects a large population. Usually, the disease is closely associated with other diseases such as obesity, hyperlipidemia, hypertension and angina. It is a well recognized that improper treatment aggravates impaired glucose tolerance and insulin resistance, leading to frank diabetes. Further, patients with insulin resistance and type 2 diabetes often have raised triglycerides and low HDL-cholesterol concentrations and therefore, have greater risk of cardiovascular diseases. The present therapy mostly includes sulfonylureas and biguamides along with insulin. This drug therapy have limitations such as mild to severe hypoglycemia, which may lead to coma or in some cases may lead to death. The later mainly results due to unsatisfactory glycaemic control. The recent addition of thiazolidinediones, drugs having insulin-sensitizing action. Thiazolidinediones are prescribed alone or in combination with other anti-diabetic agents like troglitazone, rosiglitazone and pioglitazone. These are useful in treating diabetes, affects lipid metabolism but are suspected to have tumor-inducing potential and cause hepatic dysfunction, which may lead to liver failure. Further, serious undesirable side-effects have occurred in animal and/or human studies including cardiac hypertrophy, hema dilution and liver toxicity in a few glitazones progressing to advanced human trials. The drawback is considered to be idiosyncratic. Presently, there is need for a safe and an effective drug, to treat insulin resistance, diabetes and hyperlipidemia.

Obesity is another major health problem being associated with increased morbidity and mortality. It is a metabolic disorder, in which excess of fat is accumulated in the body. Although, its etiology is unclear, the general feature includes excess of calorie intake than it is consumed. Various therapies such as dieting, exercise, appetite suppression, inhibition of fat absorption etc. have been used to combat obesity. However, more efficient therapies to treat this abnormality is essential as obesity is closely related to several diseases such as coronary heart disease, stroke, diabetes, gout, osteoarthritis, hyperlipidaemia and reduced fertility. It also leads to social and psychological problems.

Peroxisome Proliferator Activated Receptor (PPAR) is a member of the steroid/retinoid/thyroid hormone receptor family. PPARα, PPARγ and PPARδ have been identified as subtypes of PPARs. Extensive reviews regarding PPAR, their role in different diseased conditions are widely published [*Endocrine Reviews*, 20(5), 649–688 (1999); *J. Medicinal Chemistry*, 43(4), 58–550 (2000); *Cell*, 55, 932–943 (1999); *Nature*, 405, 421–424 (2000); *Trends in pharmacological Sci.*, 469–473 (2000)]. PPARγ activation has been found to play a central role in initiating and regulating adipocyte differentiation [Endocrinology 135, 798–800, (1994)] and energy homeostasis, [*Cell*, 83, 803–812 (1995); *Cell*, 99, 239–242 (1999)]. PPARγ agonists would stimulate the terminal differentiation of adipocyte precursors and cause morphological and molecular changes characteristic of a more differentiated, less malignant state. During adipocyte differentiation, several highly specialized proteins are induced, which are being involved in lipid storage and metabolism. It is accepted that PPARγ activation leads to expression of CAP gene [Cell biology, 95, 14751–14756, (1998)], however, the exact link from PPARγ activation to changes in glucose metabolism and decrease in insulin resistance in muscle has not been clear. PPARα is involved in stimulating β-oxidation of fatty acids [*Trends Endocrine. Metabolism*, 4, 291–296 (1993)] resulting in plasma circulating free fatty acid reduction [*Current Biol.*, 5, 618–621 (1995)]. Recently, role of PPARγ activation in the terminal differentiation of adipocyte precursors has been implicated in the treatment of cancer. [*Cell*, 79, 1147–1156 (1994); *Cell*, vol. No., 377–389 (1996); *Molecular Cell*, 465–470 (1998); *Carcinogenesis*, 1949–1953 (1998); *Proc. Natl. Acad. Sci.*, 94, 237–241 (1997); *Cancer Research*, 58, 3344–3352 (1998)]. Since PPARγ is expressed in certain cells consistently, PPARγ agonists would lead to nontoxic chemotherapy. There is growing evidence that PPAR agonists may also influence the cardiovascular system through PPAR receptors as well as directly by modulating vessel wall function [*Med. Res. Rev.*, 20 (5), 350–366 (2000)].

PPAR α agonists have been found useful in the treatment of obesity (WO 97/36579). Dual PPAR α and γ agonists have been suggested to be useful for Syndrome X (WO 97/25042). PPAR γ agonists and HMG-CoA reductase inhibitors have exhibited synergism and indicated the usefulness of the combination in the treatment of atherosclerosis and xanthoma (EP 0753 298).

Leptin is a protein when bound to leptin receptors is involved in sending satiety signal to the hypothalamus. Leptin resistance would therefore lead to excess food in-take, reduced energy expenditure, obesity, impaired glucose tolerance and diabetes. It has been reported that insulin sensitizers lower plasma leptin concentration [*Proc. Natl. Acad. Sci.* 93, 5793–5796 (1996): WO 98/02159)].

A number of compounds have been reported to be useful in the treatment of hyperlipidemia, hypercholesterolemia and hyperglycemia [U.S. Pat. Nos. 5,306,726, 5,985,884, 6,054,453, EP 90 3343, PCT publications Nos. WO 91/19702, WO 94/01420, WO 94/13650, WO 95/03038, WO 95/17394, WO 96/04260, WO 96/04261, WO 96/33998, WO 97/25042, WO 97/36579, WO 98/28534, WO 99/08501, WO 99/16758, WO 99/19313, WO99/20614, WO 00/23417, WO 00/23445, WO 00/23451].

A few β-aryl-α-hydroxypropanoic acids, their derivatives, and their analogs have been reported to be useful in the treatment of hyperglycemia and hypercholesterolemia. Some of such compounds described in the prior art are outlined below:

1. U.S. Pat. No. 5,306,726 and U.S. Pat. No. 5,089,514 disclose several 3-aryl-2-hydroxypropionic acid derivatives of general formulae (II) and (III) as hypolipidaemic and hypoglycemic agents. Examples of these compounds are shown in the formulae (IV) and (V).

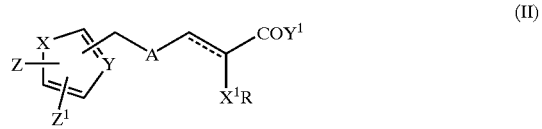

(II)

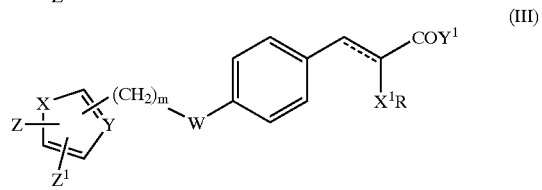

(III)

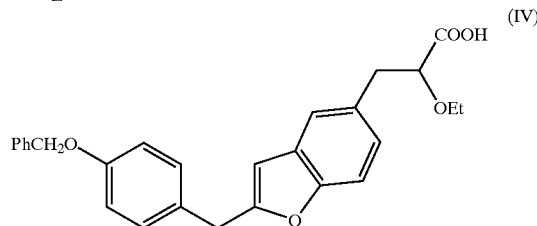

(IV)

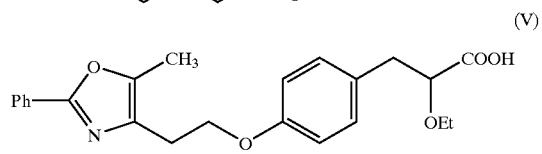

(V)

2. International Patent Applications, U.S. Pat. No. 6,166,049 and WO 96/04260 disclose compounds of general formula (VI) wherein, $R^a$ represents 2-benzoxazolyl or 2-pyridyl and $R^b$ represent $CF_3$, $CH_2OCH_3$ or $CH_3$. A typical example is (S)-3-[4-[2-[N-(2-benzoxazolyl)N-methylamino]ethoxy]phenyl]-2-(2,2,2-trifluoro ethoxy) propanoic acid (VII).

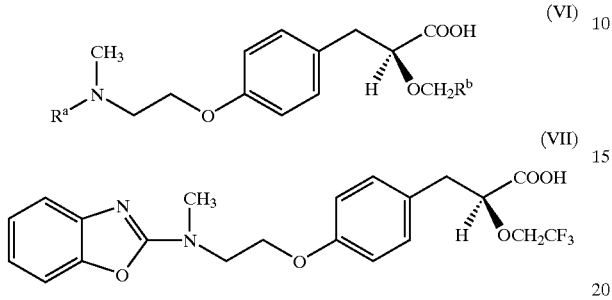

(VI)

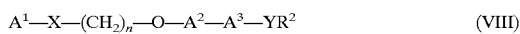

(VII)

3. International patent applications, WO 94/13650, WO 94/29302, U.S. Pat. No. 6,048,883, WO 95/17394 and WO 97/31970 disclose the compounds of general formula (VIII) wherein, $$A^1\text{—}X\text{—}(CH_2)_n\text{—}O\text{—}A^2\text{—}A^3\text{—}YR^2 \quad \text{(VIII)}$$

$A^1$ represents aromatic heterocycle moiety, $A^2$ represents substituted benzene ring and $A^3$ represents moiety of formula $(CH_2)_m\text{—}CH\text{—}(OR^1)$, where $R^1$ represents alkyl groups, m is integer of the range of 1–5; X represents substituted or unsubstituted N; Y represents C=O or C=S and $R^2$ represents $OR^3$ where $R^3$ may be hydrogen, alkyl, aralkyl, or aryl group and n is integer in the range of 2–6. An example of these compounds is shown in formula (IX).

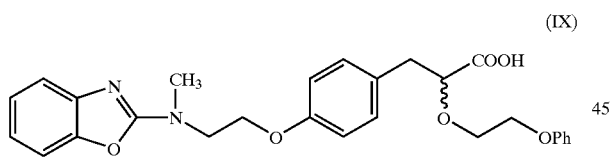

(IX)

4. International patent application, WO 00/23,445, WO 00/23,417 and WO 00/23,451 disclose cyclic compounds of the general formula (X) useful in treatment of diabetes and obesity. A typical example of these compounds is shown formulae (XI) and (XII).

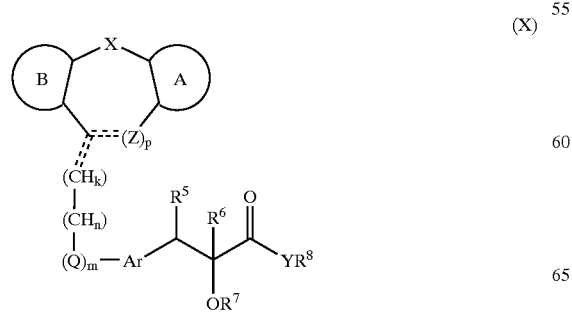

(X)

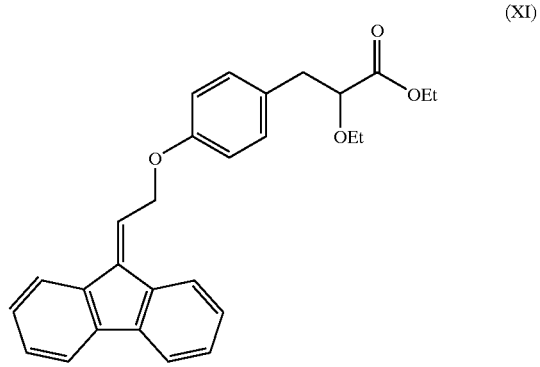

(XI)

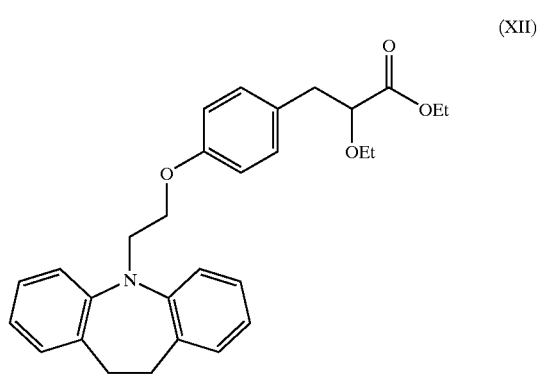

(XII)

5. International patent application, WO 99/08501 and WO 97/3197707, disclose cyclic compounds of the formulae (XIII) and (XIV) active as PPAR-gamma agonist. A typical examples of these compounds is shown formulae (XV) and (XVI).

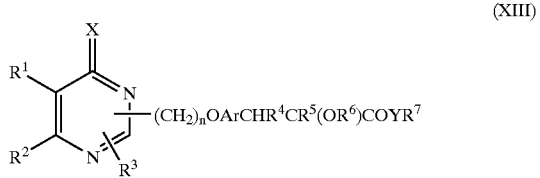

(XIII)

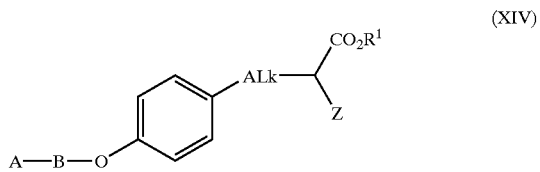

(XIV)

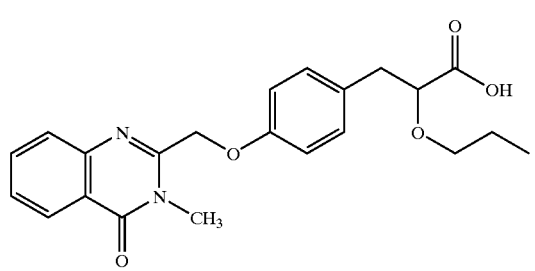

(XV)

(XVI)

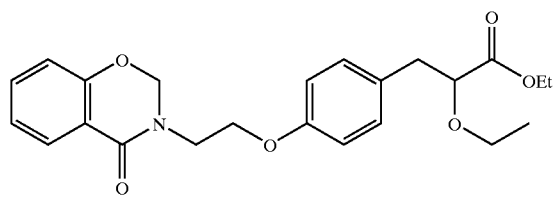

(XXI)

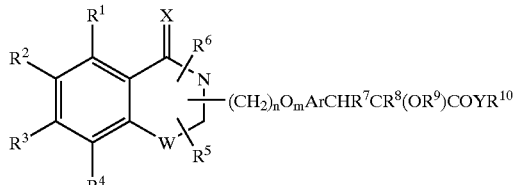

(XXII)

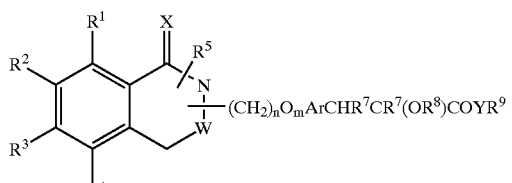

6. U.S. Pat. No. 6,054,453 and WO 99/16758 reports compounds of general formulae (XVII), (XVIII), which reduce glucose, cholesterol and triglycerides exemplified by compounds of formula (XIX).

(XVII)

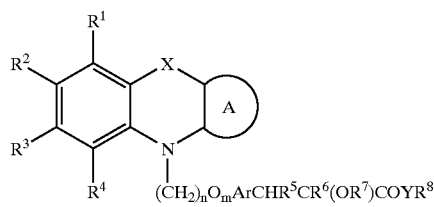

(XVIII)

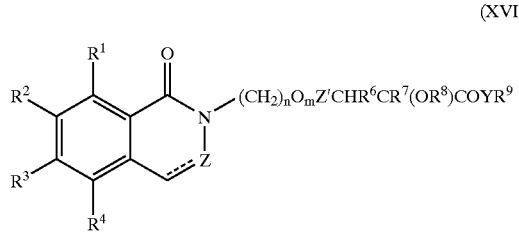

(XIX)

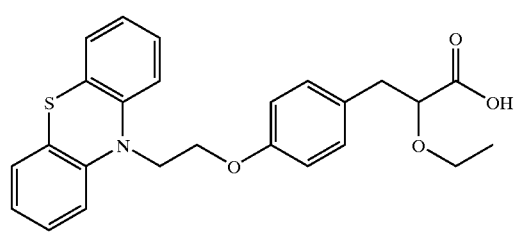

7. WO 99/19,313, U.S. Pat. No. 6,130,214 and WO 99/38850 reports compounds of general formula (XX) and (XXI) and (XXII) which reduce glucose, cholesterol and triglycerides.

(XX)

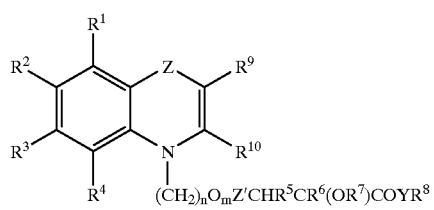

SUMMARY OF INVENTION

The objective of this invention is to develop novel compounds represented by the general formula (I) used as hypocholesterolemic, hypolipidaemic, hypolipoproteinemic, anti-obesity and antihyperglycemic agents which may have additional body weight lowering effect and beneficial effect in the treatment and/or prophylaxis of diseases caused by hyperlipidaemia, diseases classified under syndrome X and atherosclerosis.

The main objective of the present invention is to provide novel β-aryl-α-substituted propanoic acids represented by the general formula (I), their derivatives, their analogs, their tautomeric forms, their stereoisomers, their polymorphs, their pharmaceutically acceptable salts, their pharmaceutically acceptable solvates, and pharmaceutical compositions containing them or their mixtures thereof Another objective of the present invention is to provide novel β-aryl-α-substituted propanoic acids represented by the general formula (I), their derivatives, their analogs, their tautomeric forms, their stereoisomers, their polymorphs, their pharmaceutically acceptable salts, their pharmaceutically acceptable solvates, and pharmaceutical compositions containing them or their mixtures thereof having enhanced activities, without toxic effects or with reduced toxic effect.

Yet another objective of this invention is to provide a process for the preparation of novel β-aryl-α-substituted propanoic acids represented by the general formula (I), their derivatives, their analogs, their tautomeric forms, their stereoisomers, their polymorphs, their pharmaceutically acceptable salts, their pharmaceutically acceptable solvates.

Still another objective of the present invention is to provide pharmaceutical compositions containing compounds of the general formula (I), their derivatives, their analogs, their tautomeric forms, their stereoisomers, their polymorphs, their pharmaceutically acceptable salts, their pharmaceutically acceptable solvates or their mixtures in combination with suitable carriers, solvents, diluents and other media normally employed in preparing such compositions.

A further objective of the present invention is to provide process for preparation of intermediates involved in the process.

DETAILED DESCRIPTION OF THE INVENTION

Accordingly, the present invention relates to compounds of the general formula (I),

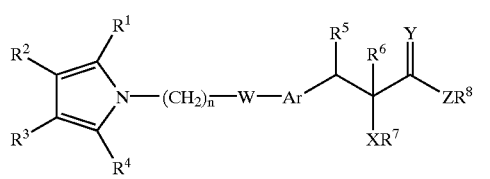

their derivatives, their analogs, their tautomeric forms, their stereoisomers, their polymorphs, their pharmaceutically acceptable salts, their pharmaceutically acceptable solvates, wherein one or more groups $R^1$, $R^2$, $R^3$, $R^4$ may be same or different and represent hydrogen, halogen, perhaloalkyl, hydroxy, thio, amino, nitro, cyano, formyl, amidino, guanidino, substituted or unsubstituted groups selected from linear or branched $(C_1-C_{12})$alkyl, linear or branched $(C_2-C_{12})$alkenyl, $(C_3-C_7)$cycloalkyl, $(C_3-C_7)$cycloalkenyl, bicycloalkyl, bicycloalkenyl, $(C_1-C_{12})$alkoxy, cyclo$(C_3-C_7)$ alkoxy, aryl, aryloxy, aralkyl, ar$(C_1-C_{12})$alkoxy, heterocyclyl, heteroaryl, heterocyclyl$(C_1-C_{12})$alkyl, heteroar$(C_1-C_{12})$alkyl, heteroaryloxy, heteroar$(C_1-C_{12})$ alkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, amimoalkyl, monoalkylaminoalkyl, dialkylaminoalkyl, alkoxyalkyl, aryloxyalkyl, aralkoxyalkyl, $(C_1-C_{12})$alkylthio, thio $(C_1-C_{12})$alkyl, arylthio, $(C_1-C_{12})$alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and its derivatives, sulfonic acid and its derivatives, phosphonic acid and its derivatives; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, $(C_1-C_{12})$alkyl or aryl; Ar represents a substituted or unsubstituted divalent single or fused aromatic, heteroaromatic or heterocyclic group; $R^5$ and $R^6$ represent both hydrogen or together represent a bond; $R^5$ and $R^6$ may also represent a hydroxy, $(C_1-C_{12})$ alkyl, $(C_1-C_{12})$alkoxy, halogen, acyl, substituted or unsubstituted aralkyl group; X represents O or S; $R^7$ represents hydrogen, perfluoro$(C_1-C_{12})$alkyl, substituted or unsubstituted groups selected from $(C_1-C_{12})$alkyl, cyclo$(C_1-C_{12})$ alkyl, aryl, ar$(C_1-C_{12})$alkyl, heteroaryl, heteroar$(C_1-C_{12})$ alkyl, heterocyclyl, alkoxyalkyl, aryloxyalkyl, alkoxycarbonyl, aryloxycarbonyl, cycloalkyloxycarbonyl, alkylaminocarbonyl, arylaminocarbonyl, acyl groups; Y represents O or S; Z represents oxygen, sulfur or $NR^{10}$, where $R^{10}$ represents hydrogen or substituted or unsubstituted groups selected from (C—$C_{12}$)alkyl, aryl, ar$(C_1-C_{12})$alkyl, hydroxy$(C_1-C_{12})$alkyl, amino$(C_1-C_{12})$alkyl, heteroaryl, heteroar$(C_1-C_{12})$ alkyl groups; $R^8$ represents hydrogen, substituted or unsubstituted groups selected from $(C_1-C_{12})$ alkyl, aryl, ar$(C_1-C_{12})$alkyl, heteroaryl, heteroar$(C_1-C_{12})$ alkyl, heterocyclyl, heterocyclylalkyl, hydroxyalkyl, alkoxyalkyl, alkylaminoalkyl groups; $R^{10}$ and $R^8$ together may form a 5 or 6 membered substituted or unsubstituted cyclic ring structure containing carbon atoms or containing one or more heteroatoms selected from O, N and S Suitable groups represented by $R^1$, $R^2$, $R^3$ and $R^4$ may be selected from hydrogen, halogen atom such as fluorine, chlorine, bromine or iodine; perhaloalkyl particularly, perfluoro$(C_1-C_6)$alkyl such as fluoromethyl, difluoromethyl, trifluoromethyl, trifluoroethyl, fluoroethyl, difluoroethyl, mono or polyhalo substituted methyl, ethyl, propyl, butyl, pentyl or hexyl groups and the like; hydroxy, thio, amino, nitro, cyano, formyl, amidino, guanidino groups; substituted or unsubstituted $(C_1-C_{12})$ alkyl group, especially, linear or branched $(C_1-C_8)$alkyl group, such as methyl, ethyl, n-propyl, iso-propyl, n-butyl, iso-butyl, t-butyl, n-pentyl, iso-pentyl, hexyl, iso-hexyl, heptyl, octyl and the like; cyclo$(C_3-C_7)$alkyl group such as cyclopropyl, cyclobutyl, cyclopentyl, cyclohexyl, cycloheptyl, the cycloalkyl group may be substituted; cyclo$(C_3-C_7)$alkenyl group such as cyclopropenyl, cyclobutenyl, cyclopentenyl, cyclohexenyl, cycloheptenyl, cycloheptadienyl, cycloheptatrienyl and the like, the cycloalkenyl group may be substituted; $(C_1-C_{12})$alkoxy, especially, $(C_1-C_6)$alkoxy group such as methoxy, ethoxy, propyloxy, iso-propyloxy, butyloxy, iso-butyloxy, pentyloxy, hexyloxy and the like, which may be substituted; cyclo$(C_3-C_7)$alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aryloxy group such as phenoxy, naphthyloxy, the aryloxy group may be substituted; aralkyl group such as benzyl, phenethyl, $C_6H_5CH_2CH_2CH_2$, naphthylmethyl and the like, the aralkyl group may be substituted; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, thiomorpholinyl, oxazolinyl, piperidinyl, piperazinyl and the like, the heterocyclyl group may be substituted; heteroaryl group such as pyridyl, thienyl, furyl, pyrrolyl, oxazolyl, thiazolyl, imidazolyl, isoxazolyl, oxadiazolyl, tetrazolyl, benzopyranyl, benzofuranyl, indolinyl, indolyl, quinolinyl, pyrimidinyl, pyrazolyl, quinazolinyl, pyrimidonyl, benzoxazinyl, benzothiazinyl, benzoxazolyl, benzothiazolyl, benzimidazolyl and the like, the heteroaryl group may be substituted; heterocyclyl $(C_1-C_6)$alkyl, such as pyrrolidinealkyl, piperidinealkyl, morpholinealkyl, thiomorpholinealkyl, oxazolinealkyl and the like, the heterocyclyl$(C_1-C_6)$alkyl group may be substituted; heteroar$(C_1-C_5)$alkyl group, wherein heteroaryl group is as defined earlier and the heteroaralkyl group may be substituted; heteroaryloxy, heteroaralkoxy, heterocyclylalkoxy, heterocyclylalkoxy wherein heteroaryl, heteroaralkyl, heterocyclylalkyl and heterocyclylalkyl moieties are as defined earlier and may be substituted; acyl group such as acetyl, propanoyl, butanoyl, pentanoyl, hexanoyl, iso-butyroyl, or benzoyl, the acyl group may be substituted and may be branched; acyloxy group wherein acyl moiety is as defined earlier, may be MeCOO, EtCOO, PrCOO, BuCOO, PhCOO and the like, which may optionally be substituted; acylamino groups, wherein acyl moiety is as defined earlier, may be $CH_3CONH$, $C_2H_5CONH$, $C_3H_7CONH$, $C_4H_9CONH$, $C_6H_5CONH$ which may be substituted; $(C_1-C_6)$monoalkylamino group such as $CH_3NH$, $C_2H_5NH$, $C_3H_7NH$, $C_4H_9NH$, $C_5H_{11}NH$, $C_6H_{13}NH$ and the like, which may be substituted; $(C_1-C_6)$dialkylamino group such as $N(CH_3)_2$, $N(Et)_2$, $CH_3(C_2H_5)N$ and the like, which may be substituted; arylamino group such as $C_6H_5NH$, $CH_3(C_6H_5)N$, $C_6H_4(CH_3)NH$, $NHC_6H_4$-Hal and the like, which may be substituted; aralkylamino group wherein aralkyl group is as defined earlier, may be such as $C_6H_5CH_2NH$, $C_6H_5CH_2CH_2NH$, $C_6H_5CH_2NCH_3$ and the like, which may be substituted; hydroxy($C_1-C_6$)alkyl which may be substituted; amino($C_1-C_6$)alkyl which may be substituted; mono($C_1-C_6$)alkylamino($C_1-C_6$)alkyl, di($C_1-C_6$) alkylamino($C_1-C_6$)alkyl group which may be substituted; alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; ($C_1-C_6$)alkylthio, thio($C_1-C_6$)alkyl which may be substituted; arylthio which may be substituted alkoxycarbonylamino group such as $C_2H_5OCONH$, $CH_3OCONH$ and the like which may be substituted; aryloxycarbonylamino group such as $C_6H_5OCONH$, $C_6H_5OCONCH_3$, $C_6H_5OCONC_2H_5$, $C_6H_4CH_3OCONH$, $C_6H_4(OCH_3)OCONH$ and the like which may be substituted; aralkoxycarbonylamino group such as $C_6H_5CH_2OCONH$, $C_6H_5CH_2CH_2OCONH$, $C_6H_5CH_2OCONCH_3$, $C_6H_5CH_2OCONC_2H_5$, $C_6H_4(CH_3)CH_2OCONH$, $C_6H_4(OCH_3)CH_2OCONH$ and the like, which may be substituted; aminocarbonylamino group, which may optionally be substituted; ($C_1-C_6$) alkylaminocarbonylamino group, di($C_1-C_6$) alkylaminocarbonyl amino group, ($C_1-C_6$)alkylamidino group, ($C_1-C_6$)alkylguanidino group, di($C_1-C_6$) alkylguanidino groups, hydrazino, ($C_1-C_6$)alkyl hydrazino groups, ($C_1-C_6$)alkoxyamino and hydroxylamino groups, which may optionally be substituted; carboxylic acid or its derivatives such as amides, like $CONH_2$, alkylaminocarbonyl like MeNHCO, $Me_2NCO$, EtNHCO, $Et_2NCO$, arylaminocarbonyl like PhNHCO, NapthNHCO and the like, which may be substituted; aralkylaminocarbonyl such as $PhCH_2NHCO$, $PhCH_2CH_2NHCO$ and the like, which may be substituted; heteroarylaminocarbonyl and heteroaralkylamino carbonyl groups where the heteroaryl groups are as defined earlier, which may be substituted; heterocyclylaminocarbonyl where the heterocyclyl group is as defined earlier, which may be substituted; carboxylic acid derivatives such as esters, wherein the ester moieties are alkoxycarbonyl such as methoxycarbonyl or ethoxycarbonyl, which may be substituted; aryloxycarbonyl group such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, which may be substituted; heteroaryloxycarbonyl, heteroaralkoxycarbonyl, wherein the heteroaryl group is as defined earlier, which may be substituted; heterocyclyloxycarbonyl where heterocycle is as defined earlier and may be substituted; sulfinyl or its derivatives like $CH_3SO$ and RSO, wherein R is substituted or unsubstituted alkyl, aryl, heteroaryl, heterocycyl and the like; sulfones or its derivatives like $RSO_2$, wherein R is substituted or unsubstituted groups selected from alkyl, aryl, heteroaryl, heterocyclyl and the like; sulfonic acid or its derivatives such as $SO_2NH_2$, $SO_2NHMe$, $SO_2NMe_2$, $SO_2NHCF_3$, $SO_2NHCO(C_1-C_6)$alkyl, $SO_2NHCOaryl$ where the aryl group is as defined earlier and the sulfonic acid derivatives may be substituted; phosphonic acid and its derivatives such as $P(O)(OH)_2$, $P(O)(O\ C_1-C_6\ alkyl)_2$, $P(O)(O\ aryl)_2$, $P(O)(OH)\ (O\ C_1-C_6\ alkyl)$ and the like.

When the groups represented by $R^1$, $R^2$, $R^3$ and $R^4$ are substituted by one or more than one, same or different groups, the substituents are selected from halogen, hydroxy, nitro, oxo, thio or unsubstituted or substituted groups selected from ($C_1-C_{12}$)alkyl, cyclo($C_1-C_{12}$)alkyl, ($C_1-C_{12}$) alkoxy, cyclo($C_1-C_{12}$)alkoxy, aryl, ar($C_1-C_{12}$)alkyl, aralkoxy($C_1-C_{12}$)alkyl, heterocyclyl, heteroaryl, heteroar ($C_1-C_{12}$)alkyl, acyl, acyloxy, hydroxy($C_1-C_{12}$)alkyl, amino, acylamino, arylamino, amino($C_1-C_{12}$)alkyl, aryloxy, aralkoxy, ($C_1-C_{12}$)alkylamino, alkoxy($C_1-C_{12}$)alkyl, ($C_1-C_{12}$)alkylthio, thio($C_1-C_{12}$)alkyl, aryl thio groups, carboxylic acid or its derivatives, or sulfenyl or its derivatives or sulfones or its derivatives or sulfonic acid or its derivatives or phosphonic acid or its derivatives.

Preferably the substituents on the pyrrole namely, $R^1$ to $R^4$ represent halogen atom such as fluorine, chlorine, bromine; hydroxy group, formyl, nitro, oxo, thio, also linear or branched alkyl such as methyl, ethyl, propyl, iso-propyl, butyl, iso-butyl, pentyl, hexyl, heptyl, octyl groups, which may be substituted; cycloalkyl group such as cyclopropyl, cyclobutyl, cyclopentyl, cyclohexyl which may be substituted; aryl group such as phenyl or naphthyl, which may be substituted; aralkyl group such as benzyl, or naphthyhnethyl, which may be substituted; ($C_1-C_6$)alkoxy, benzyloxy, acyl or acyloxy groups; heteroaryl group such as pyridyl, thienyl, furyl, pyrrolyl, oxazolyl, thiazolyl, imidazolyl, isoxazolyl, oxadiazolyl, tetrazolyl, benzopyranyl, benzofuranyl, indolinyl, indolyl, quinolinyl, pyrimidinyl, pyrazolyl, quinazolinyl, pyrimidonyl, benzoxazinyl, benzothiazinyl, benzoxazolyl, benzothiazolyl, benzimidazolyl and the like, the heteroaryl group may be substituted; heterocyclyl groups such as aziridinyl, pyrrolidinyl, morpholinyl, thiomorpholinyl, oxazolinyl, piperidinyl, piperazinyl and the like, the heterocyclyl group may be substituted; carboxylic acid and its derivatives; alkylaminocarbonyl or arylaminocarbonyl groups which may be substituted; thioalkyl, alkylsulfenyl, arylthio, alkylsulfonyl, arylsulfenyl, arylsulfonyl, which may be optionally halogenated.

Suitable cyclic structures formed by the two adjacent groups $R^2$ and $R^3$ together with the carbon atoms to which they are attached contain 5 to 6 ring atoms which may optionally contain one or more heteroatoms selected from oxygen, nitrogen or sulfur and optionally contain one or more double bonds. The cyclic structure may further be optionally substituted phenyl, pyridyl, furanyl, thienyl, pyrrolyl, imidazolyl, isoxazolyl, pyrimidinyl, pyrazinyl and the like. Suitable substituents on the cyclic structure formed by $R^2$ and $R^3$ together with the adjacent carbon atoms to which they are attached include oxo, hydroxy, halogen atom such as chlorine, bromine and iodine; nitro, cyano, amino, formyl, ($C_1-C_3$)alkyl, ($C_1-C_6$)alkoxy, thioalkyl, arylthio, alkylthio, phenyl or benzyl groups.

The $R^1$, $R^2$, $R^3$ and $R^4$ groups on the pyrrole, when further substituted preferable substitutents are halogen, hydroxy, formyl, nitro, oxo, thio, or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkylamino, alkoxyalkyl, alkylthio, thioalkyl, arylthio, alkylsulfenyl, alkylsulfonyl, arylsulfenyl, arylsulfonyl, carboxylic acid or its derivatives, or sulfonic acid or its derivatives or phosphonic acid or its derivatives.

n is an integer in the range of 1 to 8. It is preferred that n be 1 to 4.

Suitable groups represented by Ar include substituted or unsubstituted groups selected from divalent moieties selected from phenylene, naphthalene, pyridyl, quinolinyl, benzofuryl, dihydrobenzofuryl, benzopyranyl, indolyl, indolinyl, azaindolyl, azaindolyl, pyrazolyl, benzothiazolyl, benzoxazolyl and the like.

The substituents on the group represented by Ar may be selected from substituted or unsubstituted linear or branched $(C_1–C_6)$alkyl, $(C_1–C_6)$alkoxy, halogen, haloalkyl, haloalkoxy, acyl, amino, acylamino, oxo, thio, thioalkyl, arylthio or carboxylic or sulfonic acids and their derivatives or phosphonic acid and their derivatives.

It is preferred that Ar represents substituted or unsubstituted divalent phenylene, naphthylene, benzofuryl, indolyl, indolinyl, quinolinyl, azaindolyl, azaindolinyl, benzothiazolyl or benzoxazolyl groups.

It is more preferred that Ar is represented by divalent phenylene or naphthylene, which may be unsubstituted or substituted by halogen, methyl, halomethyl, methoxy or halomethoxy groups.

Suitable $R^5$ includes hydrogen, lower alkyl groups such as methyl, ethyl or propyl; hydroxy, $(C_1–C_6)$alkoxy, halogen atom such as fluorine, chlorine, bromine, or iodine; aralkyl such as benzyl, phenethyl, which may be unsubstituted or substituted or $R^5$ together with $R^6$ represent a bond.

Suitable $R^6$ may be hydrogen, lower alkyl groups such as methyl, ethyl or propyl; hydroxy, $(C_1–C_6)$alkoxy; halogen atom such as fluorine, chlorine, bromine, iodine; acyl group such as linear or branched $(C_2–C_{10})$ acyl group such as acetyl, propanoyl, butanoyl, pentanoyl, benzoyl and the like; aralkyl such as benzyl, phenethyl, which may be unsubstituted or substituted or together with $R^5$ forms a bond.

When $R^5$ or $R^6$ represent substituted aralkyl, the preferred substituents are hydroxy, halogen, alkyl and alkoxy.

It is preferred that $R^5$ or $R^6$ represent hydrogen atom or $R^5$ and $R^6$ together represent a bond.

Suitable groups represented by $R^7$ may be selected from hydrogen, substituted or unsubstituted, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like; $(C_3–C_7)$cycloalkyl group such as cyclopropyl, cyclobutyl, cyclopentyl, cyclohexyl and the like, the cycloalkyl group may be substituted; aryl group such as phenyl, naphthyl, the aryl group may be substituted; heteroaryl group such as pyridyl, thienyl, furyl, pyrrolyl, oxazolyl, thiazolyl, imidazolyl, isoxazolyl, oxadiazolyl, tetrazolyl, benzopyranyl, benzofuranyl, indolinyl, indolyl, quinolinyl, pyrimidinyl, pyrazolyl, quinazolinyl, pyrimidonyl, benzoxazinyl, benzothiazinyl, benzoxazolyl, benzothiazolyl, benzimidazolyl and the like, the heteroaryl group may be substituted; heteroar$(C_1–C_6)$alkyl group wherein the heteroaryl groups are as defined earlier and the heteroar$(C_1–C_6)$alkyl group may be substituted; aralkyl group wherein the alkyl moiety may contain $C_1–C_6$ atoms such as benzyl and phenethyl etc, wherein the aryl moiety may be substituted; heterocyclyl groups such as aziridinyl, pyrrolidinyl, morpholinyl, thiomorpholinyl, oxazolinyl, piperidinyl, piperazinyl and the like, the heterocyclyl group may be substituted; $(C_1–C_6)$alkoxy$(C_1–C_6)$alkyl group such as methoxymethyl, ethoxymethyl, methoxyethyl, ethoxypropyl and the like, the alkoxyalkyl group may be substituted; substituted or unsubstituted, linear or branched $(C_2–C_{16})$acyl group such as acetyl, propanoyl, butanoyl, benzoyl, octanoyl, decanoyl and the like; $(C_1–C_6)$alkoxycarbonyl, the alkyl group may be substituted; aryloxycarbonyl such as phenoxycarbonyl, naphthyloxycarbonyl, the aryl group may be substituted; $(C_1–C_6)$alkylaminocarbonyl, the alkyl group may be substituted; arylaminocarbonyl such as PhNHCO, or naphthylaminocarbonyl, the aryl moiety may be substituted. The substituents on $R^7$ may be selected from the group consisting of halogen, hydroxy, nitro, oxo, thio or unsubstituted/substituted groups selected from alkyl, cycloalkyl, alkoxy, cycloalkoxy, aryl, aralkyl, aryloxy, aryloxy, alkyl, aralkoxyalkyl, heterocyclyl, heteroaryl, heteroaryloxy, heteroaralkyl, acyl, acyloxy, hydroxyalkyl, amino, acylamino, arylamino, aminoalkyl, alkoxycarbonyl, alkylamino, alkoxyalkyl, alkylthio, thioalkyl, arylthio groups, carboxylic acid or its derivatives, or sulfonic acid or its derivatives.

Suitable groups represented by $R^8$ may be selected from hydrogen, substituted or unsubstituted, linear or branched $(C_1–C_{16})$alkyl, preferably $(C_1–C_{12})$alkyl group such as methyl, ethyl, n-propyl, iso-propyl, n-butyl, iso-butyl, pentyl, hexyl, octyl and the like; $(C_3–C_7)$cycloalkyl such as cyclopropyl, cyclobutyl, cyclopentyl, cyclohexyl and the like, the cycloalkyl group may be substituted; aryl group such as phenyl, naphthyl, the aryl group may be substituted; heteroaryl group such as pyridyl, thienyl, furyl, pyrrolyl, oxazolyl, thiazolyl, imidazolyl, isoxazolyl, oxadiazolyl, tetrazolyl, benzopyranyl, benzofuranyl, indolinyl, indolyl, quinolinyl, pyrimidinyl, pyrazolyl, quinazolinyl, pyrimidonyl, benzoxazinyl, benzothiazinyl, benzoxazolyl, benzothiazolyl, benzimidazolyl and the like, the heteroaryl group may be substituted; heteroaralkyl group such as furanemethyl, pyridinemethyl, oxazolemethyl, oxazolethyl and the like, the heteroaralkyl group may be substituted; aralkyl group such as benzyl and phenethyl, the aralkyl group may be substituted; heterocyclyl groups such as aziridinyl, pyrrolidinyl, morpholinyl, thiomorpholinyl, oxazolinyl, piperidinyl, piperazinyl and the like, the heterocyclyl group may be substituted. The substituents on $R^8$ may be selected from halogen, hydroxy, nitro formyl, oxo, thio or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl aryloxy, aralkoxy, alkoxycarbonyl, alkylamino, alkoxyalkyl, alkylthio, thioalkyl, arylthio, carboxylic acid or its derivatives, or sulfonic acid or its derivatives.

Z represents oxygen, sulfur or $NR^{10}$.

Suitable groups represented by $R^{10}$ may be selected from hydrogen, substituted or unsubstituted, linear or branched $(C_1–C_{16})$alkyl, preferably $(C_1–C_{12})$alkyl; hydroxy$(C_1–C_6)$alkyl; aryl group such as phenyl, naphthyl; aralkyl group such as benzyl and phenethyl; heterocyclyl groups such as aziridinyl, pyrrolidinyl, morpholinyl, thiomorpholinyl, oxazolinyl, piperidinyl, piperazinyl and the like, the heterocyclyl group may be substituted; heteroaryl group such as pyridyl, thienyl, furyl, pyrrolyl, oxazolyl, thiazolyl, imidazolyl, isoxazolyl, oxadiazolyl, tetrazolyl, benzopyranyl, benzofuranyl, indolinyl, indolyl, quinolinyl, pyrimidinyl, pyrazolyl, quinazolinyl, pyrimidonyl, benzoxazinyl, benzothiazinyl, benzoxazolyl, benzothiazolyl, benzimidazolyl and the like, the heteroaryl group may be substituted.

The cyclic structure formed by $R^8$ and $R^{10}$ together with the carbon atoms to which they are attached may be a substituted or unsubstituted 5 or 6 membered cyclic structure containing carbon atoms which may optionally contain one or two heteroatoms selected from oxygen, nitrogen or sulfur. The cyclic structure may contain one or more double bonds.

Suitable ring structures formed by $R^8$ and $R^{10}$ together may be selected from pyrrolidinyl, piperidinyl, morpholinyl, thiomorpholinyl, piperazinyl, oxazolinyl, diazolinyl and the like. Suitable substituents on the cyclic structure formed by R$^8$ and R$^{10}$ taken together may be selected from halogen, hydroxy, alkyl, oxo, thio, aryl, aralkyl and the like.

For any R$^1$, R$^2$, R$^3$, R$^4$, R$^5$, R$^6$, R$^7$, R$^8$, R$^9$, R$^{10}$ and Ar that may be substituted, the substituents are as defined anywhere in this specification.

Suitable n is an integer ranging from 1 to 6, preferably n represents an integer 2 to 4.

Pharmaceutically acceptable salts forming part of this invention are intended to define but not limited to salts of the carboxylic acid moiety such as alkali metal salts like Li, Na, and K salts; alkaline earth metal salts like Ca and Mg salts; salts of organic bases such as lysine, arginine, guanidine and its derivatives, which may be optionally substituted, diethanolamine, choline, tromethamine and the like; ammonium or substituted ammonium salts and aluminium salts. Salts may be acid addition salts which defines but not limited to sulfates, bisulfates, nitrates, phosphates, perchlorates, borates, hydrohalides, acetates, tartrates, maleates, fumarates, maleiates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention includes (±) Ethyl 3-{4-[2-(pyrrol-1-yl)ethoxy]phenyl}-2-ethoxypropanoate;
(+) Ethyl 3-{4-[2-(pyrrol-1-yl)ethoxy]phenyl}-2-ethoxypropanoate;
(−) Ethyl 3-{4-[2-(pyrrol-1-yl)ethoxy]phenyl}-2-ethoxypropanoate;
(±) Ethyl 3-{4-[2-(2,5-dimethylpyrrol-1-yl)ethoxy]phenyl}-2-ethoxypropanoate;
(+) Ethyl 3-{4-[2-(2,5-dimnethylpyrrol-1-yl)ethoxy]phenyl}-2-ethoxypropanoate;
(−) Ethyl 3-{4-[2-(2,5-dimethylpyrrol-1-yl)ethoxy]phenyl}-2-ethoxypropanoate;
(±) Ethyl 3-{4-[2-(2,4-dimethylpyrrol-1-yl)ethoxy]phenyl}-2-ethoxypropanoate;
(+) Ethyl 3-{4-[2-(2,4-dimethylpyrrol-1-yl)ethoxy]phenyl}-2-ethoxypropanoate;
(−) Ethyl 3-{4-[2-(2,4-dimethylpyrrol-1-yl)ethoxy]phenyl}-2-ethoxypropanoate;
(±) Ethyl 3-{4-[2-(2-formylpyrrol-1-yl)ethoxy]phenyl}-2-ethoxypropanoate;
(+) Ethyl 3-{4-[2-(2-formylpyrrol-1-yl)ethoxy]phenyl}-2-ethoxypropanoate;
(−) Ethyl 3-{4-[2-(2-formylpyrrol-1-yl)ethoxy]phenyl}-2-ethoxypropanoate;
(±) Ethyl 3-{4-[2-(2-acetylpyrrol-1-yl)ethoxy]phenyl}-2-ethoxypropanoate;
(+) Ethyl 3-{4-[2-(2-acetylpyrrol-1-yl)ethoxy]phenyl}-2-ethoxypropanoate;
(−) Ethyl 3-{4-[2-(2-acetylpyrrol-1-yl)ethoxy]phenyl}-2-ethoxypropanoate;
(±) Ethyl 3-{4-[2-(2-ethylpyrrol-1-yl)ethoxy]phenyl}-2-ethoxypropanoate;
(+) Ethyl 3-{4-[2-(2-ethylpyrrol-1-yl)ethoxy]phenyl}-2-ethoxypropanoate;
(−) Ethyl 3-{4-[2-(2-ethylpyrrol-1-yl)ethoxy]phenyl}-2-ethoxypropanoate;
(±) Ethyl 3-{4-[2-(2-ethyl-5-methylpyrrol-1-yl)ethoxy]phenyl}-2-ethoxypropanoate;
(+) Ethyl 3-{4-[2-(2-ethyl-5-methylpyrrol-1-yl)ethoxy]phenyl}-2-ethoxypropanoate;
(−) Ethyl 3-{4-[2-(2-ethyl-5-methylpyrrol-1-yl)ethoxy]phenyl}-2-ethoxypropanoate;
(±) Ethyl 3-{4-[2-(5-methyl-2-propylpyrrol-1-yl)ethoxy]phenyl}-2-ethoxypropanoate;
(+) Ethyl 3-{4-[2-(5-methyl-2-propylpyrrol-1-yl)ethoxy]phenyl}-2-ethoxypropanoate;
(−) Ethyl 3-{4-[2-(5-methyl-2-propylpyrrol-1-yl)ethoxy]phenyl}-2-ethoxypropanoate;
(±) Ethyl 3-{4-[2-(5-methyl-2-n-butylpyrrol-1-yl)ethoxy]phenyl}-2-ethoxypropanoate;
(+) Ethyl 3-{4-[2-(5-methyl-2-n-butylpyrrol-1-yl)ethoxy]phenyl}-2-ethoxypropanoate;
(−) Ethyl 3-{4-[2-(5-methyl-2-n-butylpyrrol-1-yl)ethoxy]phenyl}-2-ethoxypropanoate;
(±)Ethyl 3-{4-[2-(5-methyl-2-phenylpyrrol-1-yl)ethoxy]phenyl}-2-ethoxypropanoate;
(+) Ethyl 3-{4-[2-(5-methyl-2-phenylpyrrol-1-yl)ethoxy]phenyl}-2-ethoxypropanoate;
(−)Ethyl 3-{4-[2-(5-methyl-2-phenylpyrrol-1-yl)ethoxy]phenyl}-2-ethoxypropanoate;
(±) Ethyl 3-{4-[2-(5-methyl-3-phenylpyrrol-1-yl)ethoxy]phenyl}-2-ethoxypropanoate;
(+) Ethyl 3-{4-[2-(5-methyl-3-phenylpyrrol-1-yl)ethoxy]phenyl}-2-ethoxypropanoate;
(−) Ethyl 3-{4-[2-(5-methyl-3-phenylpyrrol-1-yl)ethoxy]phenyl}-2-ethoxypropanoate;
(±) Ethyl 3-{4-[2-(5-methyl-2-phenylpyrrol-1-yl)ethoxy]phenyl}-2-methoxypropanoate;
(+) Ethyl 3-{4-[2-(5-methyl-2-phenylpyrrol-1-yl)ethoxy]phenyl}-2-methoxypropanoate;
(−) Ethyl 3-{4-[2-(5-methyl-2-phenylpyrrol-1-yl)ethoxy]phenyl}-2-methoxypropanoate;
(±) Methyl 3-{4-[2-(5-methyl-2-phenylpyrrol-1-yl)ethoxy]phenyl}-2-methoxypropanoate;
(+) Methyl 3-{4-[2-(5-methyl-2-phenylpyrrol-1-yl)ethoxy]phenyl}-2-methoxypropanoate;
(−) Methyl 3-{4-[2-(5-methyl-2-phenylpyrrol-1-yl)ethoxy]phenyl}-2-methoxypropanoate;
(±) Ethyl 3-{4-[2-(5-methyl-2-phenylpyrrol-1-yl)ethoxy]phenyl}-2-propoxypropanoate;
(+) Ethyl 3-{4-[2-(5-methyl-2-phenylpyrrol-1-yl)ethoxy]phenyl}-2-propoxypropanoate;
(−) Ethyl 3-{4-[2-(5-methyl-2-phenyl)pyrrol-1-yl)ethoxy]phenyl}-2-propoxypropanoate;
(±) Propyl 3-{4-[2-(5-methyl-2-phenylpyrrol-1-yl)ethoxy]phenyl}-2-propoxypropanoate;
(+) Propyl 3-{4-[2-(5-methyl-2-phenylpyrrol-1-yl)ethoxy]phenyl}-2-propooxypropanoate;
(−) Propyl 3-{4-[2-(5-methyl-2-phenylpyrrol-1-yl)ethoxy]phenyl}-2-propoxypropanoate;
(±) Ethyl 3-{4-[2-(5-methyl-2-(4-methylphenyl)pyrrol-1-yl)ethoxy]phenyl}-2-ethoxypropanoate;
(+) Ethyl 3-{4-[2-(5-methyl-2-(4-methylphenyl)pyrrol-1-yl)ethoxy]phenyl}-2-ethoxypropanoate;
(−) Ethyl 3-{4-[2-(5-methyl-2-(4-methylphenyl)pyrrol-1-yl)ethoxy]phenyl}-2-propoxypropanoate;
(±) Ethyl 3-{4-[2-5-methyl-2-(3-methylphenyl)pyrrol-1-yl)ethoxy]phenyl}-2-ethoxypropanoate;
(+) Ethyl 3-{4-[2-(5-methyl-2-(3-methylphenyl)pyrrol-1-yl)ethoxy]phenyl}-2-ethoxypropanoate;
(−) Ethyl 3-{4-[2-(5-methyl-2-(3-methylphenyl)pyrrol-1-yl)ethoxy]phenyl}-2-ethoxypropanoate;
(±) Ethyl 3-{4-[2-(5-methyl-2-(2-methylphenyl)pyrrol-1-yl)ethoxy]phenyl}-2-ethoxypropanoate;
(+) Ethyl 3-{4-[2-(5-methyl-2-(2-methylphenyl)pyrrol-1-yl)ethoxy]phenyl}-2-ethoxypropanoate;
(−) Ethyl 3-{4-[2-(5-methyl-2-(2-methylphenyl)pyrrol-1-yl)ethoxy]phenyl}-2-ethoxypropanoate;

(±) Ethyl 3-{4-[2-(5-methyl-2-(4-methoylphenyl)pyrrol-1-yl)ethoxy]phenyl}-2-ethoxypropanoate;
(+) Ethyl 3-{4-[2-(5-methyl-2-(4-methylphenyl)pyrrol-1-yl)ethoxy]phenyl}-2-ethoxypropanoate,
(−) Ethyl 3-{4-[2-(5-methyl-2-(4-methoxyphenyl)pyrrol-1-yl)ethoxy]phenyl}-2-ethoxypropanoate;
(±) Ethyl 3-{4-[2-(5-methyl-2-(4-bromophenyl)pyrrol-1-yl)ethoxy]phenyl}-2-ethoxypropanoate;
(+) Ethyl 3-{4-[2-(5-methyl-2-(4-bromophenyl)pyrrol-1-yl)ethoxy]phenyl}-2-ethoxypropanoate;
(−) Ethyl 3-{4-[2-(5-methyl-2-(4-bromophenyl)pyrrol-1-yl)ethoxy]phenyl}-2-ethoxypropanoate;
(±) Ethyl 3-{4-[2-(5-methyl-2-(4-fluorophenyl)pyrrol-1-yl)ethoxy]phenyl}-2-ethoxypropanoate;
(+) Ethyl 3-{4-[2-(5-methyl-2-(4-fluorophenyl)pyrrol-1-yl)ethoxy]phenyl}-2-ethoxypropanoate;
(−) Ethyl 3-{4-[2-(5-methyl-2-(4-fluorophenyl)pyrrol-1-yl)ethoxy]phenyl}-2-ethoxypropanoate;
(±) Ethyl 3-{4-[2-(5-methyl-2-(4-chlorophenyl)pyrrol-1-yl)ethoxy]phenyl}-2-ethoxypropanoate;
(+) Ethyl 3-{4-[2-(5-methyl-2-(4-chlorophenyl)pyrrol-1-yl)ethoxy]phenyl}-2-ethoxypropanoate;
(−) Ethyl 3-{4-[2-(5-methyl-2-(4-chlorophenyl)pyrrol-1-yl)ethoxy]phenyl}-2-ethoxypropanoate;
(±) Ethyl 3-{4-[2-(4-methyl-2-phenylpyrrol-1-yl)ethoxy]phenyl}-2-ethoxypropanoate;
(+) Ethyl 3-{4-[2-(4-methyl-2-phenylpyrrol-1-yl)ethoxy]phenyl}-2-ethoxypropanoate;
(−) Ethyl 3-{4-[2-(4-methyl-2-phenylpyrrol-1-yl)ethoxy]phenyl}-2-ethoxypropanoate;
(±) Ethyl 3-{4-[2-(5-methyl-2,3-diphenylpyrrol-1-yl)ethoxy]phenyl}-2-ethoxypropanoate;
(+) Ethyl 3-{4-[2-(5-methyl-2,3-diphenylpyrrol-1-yl)ethoxy]phenyl}-2-ethoxypropanoate;
(−) Ethyl 3-{4-[2-(5-methyl-2,3-diphenylpyrrol-1-yl)ethoxy]phenyl}-2-ethoxypropanoate;
(±) Ethyl 3-{4-[2-(2-isopropyl-5-methylpyrrol-1-yl)ethoxy]phenyl}-2-ethoxypropanoate;
(+) Ethyl 3-{4-[2-(2-isopropyl-5-methylpyrrol-1-yl)ethoxy]phenyl}-2-ethoxypropanoate;
(−) Ethyl 3-{4-[2-(2-isopropyl-5-methylpyrrol-1-yl)ethoxy]phenyl}-2-ethoxypropanoate;
(±) Ethyl 3-{4-[2-(2,5-diisopropylpyrrol-1-yl)ethoxy]phenyl}-2-ethoxypropanoate;
(+) Ethyl 3-{4-[2-(2,5-diisopropylpyrrol-1-yl)ethoxy]phenyl}-2-ethoxypropanoate;
(−) Ethyl 3-{4-[2-(2,5-diisopropylpyrrol-1-yl)ethoxy]phenyl}-2-ethoxypropanoate;
(±) Ethyl 3-{4-[2-(5-isopropyl-2-phenylpyrrol-1-yl)ethoxy]phenyl}-2-ethoxypropanoate;
(+) Ethyl 3-{4-[2-(5-isopropyl-2-phenylpyrrol-1-yl)ethoxy]phenyl}-2-ethoxypropanoate;
(−) Ethyl 3-{4-[2-(5-isopropyl-2-phenylpyrrol-1-yl)ethoxy]phenyl}-2-ethoxypropanoate;
(±) Ethyl 3-{4-[2-(2,5-diisopropyl-3-phenylpyrrol-1-yl)ethoxy]phenyl}-2-ethoxypropanoate;
(+) Ethyl 3-{4-[2-(2,5-diisopropyl-3-phenylpyrrol-1-yl)ethoxy]phenyl}-2-ethoxypropanoate;
(−) Ethyl 3-{4-[2-(2,5-diisopropyl-3-phenylpyrrol-1-yl)ethoxy]phenyl}-2-ethoxypropanoate;
(±) Ethyl 3-(4-{2-[5-isopropyl-2-(4-methoxyphenyl)pyrrol-1-yl]ethoxy}phenyl)-2-ethoxypropanoate;
(+) Ethyl 3-(4-{2-[5-isopropyl-2-(4-methloxyphenyl)pyrrol-1-yl]ethoxy}phenyl)-2-ethoxypropanoate;
(−) Ethyl 3-(4-{2-[5-isopropyl-2-(4-methoxyphenyl)pyrrol-1-yl]ethoxy}phenyl)-2-ethoxypropanoate;
(±) Ethyl 3-(4-{2-[2-(4-fluorophenyl)-5-isopropylpyrrol-1-yl]ethoxy}phenyl)-2-ethoxypropanoate;
(+) Ethyl 3-(4-{2-[2-(4-fluorophenyl)-5-isopropylpyrrol-1-yl]ethoxy}phenyl)-2-ethoxypropanoate;
(−) Ethyl 3-(4-{2-[2-(4-fluorophenyl)-5-isopropylpyrrol-1-yl]ethoxy}phenyl)-2-ethoxypropanoate;
(±) Ethyl 3-(4-{2-[2-(4-fluorophenyl)-5-isopropyl-3-phenylpyrrol-1-yl]ethoxy}phenyl)-2-ethoxy propanoate;
(+) Ethyl 3-(4-{2-[2-(4-fluorophenyl)-5-isopropyl-3-phenylpyrrol-1-yl]ethoxy}phenyl)-2-ethoxy propanoate;
(−) Ethyl 3-(4-{2-[2-(4-fluorophenyl)-5-isopropyl-3-phenylpyrrol-1-yl]ethoxy}phenyl)-2-ethoxy propanoate;
(±) Ethyl 3-(4-{2-[2-(4-fluorophenyl)-5-isopropyl-4-phenylcarbamoylpyrrol-1-yl]ethoxy}phenyl)-2-ethoxypropanoate;
(+) Ethyl 3-(4-{2-[2-(4-fluorophenyl)-5-isopropyl-4-phenylcarbamoylpyrrol-1-yl]ethoxy}phenyl)-2-ethoxypropanoate;
(−) Ethyl 3-(4-{2-[2-(4-fluorophenyl)-5-isopropyl-4-phenylcarbamoylpyrrol-1-yl]ethoxy}phenyl)-2-ethoxypropanoate;
(±) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate;
(+) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate;
(−) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate;
(±) Ethyl 3-(4-{3-[2-(4-fluorophenyl)-5-isopropyl-3-phenyl-4-phenylcarbamoylpyrrol-1-yl]propoxy}phenyl)-2-ethoxypropanoate;
(+) Ethyl 3-(4-{3-[2-(4-fluorophenyl)-5-isopropyl-3-phenyl-4-phenylcarbamoylpyrrol-1-yl]propoxy}phenyl)-2-ethoxypropanoate;
(−) Ethyl 3-(4-{3-[2-(4-fluorophenyl)-5-isopropyl-3-phenyl-4-phenylcarbamoylpyrrol-1-yl]propoxy}phenyl)-2-ethoxypropanoate;
(±) Ethyl 3-(4-{2-[2-(4-fluorophenyl)-5-phenylpyrrol-1-yl]ethoxy}phenyl)-2-ethoxypropanoate;
(+) Ethyl 3-(4-{2-[2-(4-fluorophenyl)-5-phenylpyrrol-3-yl]ethoxy}phenyl)-2-ethoxypropanoate;
(−) Ethyl 3-(4-{2-[2-(4-fluorophenyl)-5-phenylpyrrol-1-yl]ethoxy}phenyl)-2-ethoxyropanoate;
(±) Ethyl 3-[4-[2-[3-carboxy-5-phenyl-2-(4-fluorophenyl)pyrrol-1-yl)ethoxy]phenyl-2-ethoxy propanoate;
(+) Ethyl 3-[4-[2-[3-carboxy-5-phenyl-2-(4-fluorophenyl)pyrrol-1-yl)ethoxy]phenyl-2-ethoxy propanoate;
(−) Ethyl 3-[4-[2-[3-carboxy-5-phenyl-2-(4-fluorophenyl)pyrrol-1-yl)ethoxy]phenyl-2-ethoxy propanoate;
(±) Ethyl 3-{4-[2-(2-methylthiopyrrol-1-yl)ethoxy]phenyl}-2-ethoxypropanoate;
(+) Ethyl 3-{4-[2-(2-methylthiopyrrol-1-yl)ethoxy]phenyl}-2-ethoxypropanoate;
(−) Ethyl 3-{4-[2-(2-methylthiopyrrol-1-yl)ethoxy]phenyl}-2-ethoxypropanoate;
Ethyl (E/Z) 3-{4-[2-(5-methyl-2-phenyl-pyrrol-1-yl)ethoxy]phenyl}-2-ethoxyprop-2-enenoate;
Ethyl (Z) 3-{4-[2-(5-methyl-2-phenyl-pyrrol-1-yl)ethoxy]phenyl}-2-ethoxyprop-2-enenoate;
Ethyl (E) 3-{4-[2-(5-methyl-2-phenyl-pyrrol-1-yl)ethoxy]phenyl}-2-ethoxyprop-2-enenoate;
[(2R)—N(1S)]-2-Ethoxy-3-{4-[2-(5-methyl-2-phenylpyrrol-1-yl)ethoxy]phenyl}-N-(2-hydroxy-1-phenylethyl)propanamide;
[(2S)—N(1S)]-2-Ethoxy-{3-14-[2-(5-methyl-2-phenylpyrrol-1-yl)ethoxy]phenyl}-N-(2-hydroxy-1-phenylethyl) propanamide (±) 3-{4-[2-(pyrrol-1-yl)ethoxy]phenyl}-2-ethoxypropanoic acid and its pharmaceutically acceptable salts;
(+) 3-{4-[2-(pyrrol-1-yl)ethoxy]phenyl}-2-ethoxypropanoic acid and its pharmaceutically acceptable salts;
(−) 3-{4-[2-(pyrrol-1-yl)ethoxy]phenyl}-2-ethoxypropanoic acid and its pharmaceutically acceptable salts;
(±) 3-{4-[2-(2,5-dimethylpyrrol-1-yl)ethoxy]phenyl}-2-ethoxypropanoic acid and its pharmaceutically acceptable salts;
(+) 3-{4-[2-(2,5-dimethylpyrrol-1-yl)ethoxy]phenyl}-2-ethoxypropanoic acid and its pharmaceutically acceptable salts;
(−) 3-{4-[2-(2,5-dimethylpyrrol-1-yl)ethoxy]phenyl}-2-ethoxypropanoic acid and its pharmaceutically acceptable salts;
(±) 3-{4-[2-(2,4-dimethylpyrrol-1-yl)ethoxy]phenyl}-2-ethoxypropanoic acid and its pharmaceutically acceptable salts;
(+) 3-{4-[2-(2,4-dimethylpyrrol-1-yl)ethoxy]phenyl}-2-ethoxypropanoic acid and its pharmaceutically acceptable salts;
(−) 3-{4-[2-(2,4-di-methylpyrrol-1-yl)ethoxy]phenyl}-2-ethoxypropanoic acid and its pharmaceutically acceptable salts;
(±) 3-{4-[2-(2-ethylpyrrol-1-yl)ethoxy]phenyl}-2-ethoxypropanoic acid and its pharmaceutically acceptable salts;
(+) 3-{4-[2-(2-ethylpyrrol-1-yl)ethoxy]phenyl}-2-ethoxypropanoic acid and its pharmaceutically acceptable salts;
(−) 3-{4-[2-(2-ethylpyrrol-1-yl)ethoxy]phenyl}-2-ethoxypropanoic acid and its pharmaceutically acceptable salts;
(±) 3-{4-[2-(2-formylpyrrol-1-yl)ethoxy]phenyl}-2-ethoxypropanoic acid and its pharmaceutically acceptable salts;
(+) 3-{4-[2-(2-formylpyrrol-1-yl)ethoxy]phenyl}-2-ethoxypropanoic acid and its pharmaceutically acceptable salts;
(−) 3-{4-[2-(2-formylpyrrol-1-yl)ethoxy]phenyl}-2-ethoxypropanoic acid and its pharmaceutically acceptable salts;
(±) 3-{4-[2-(2-acetylpyrrol-1-yl)ethoxy]phenyl}-2-ethoxypropanoic acid and its pharmaceutically acceptable salts;
(+) 3-{4-[2-(2-acetylpyrrol-1-yl)ethoxy]phenyl}-2-ethoxypropanoic acid and its pharmaceutically acceptable salts;
(−) 3-{4-[2-(2-acetylpyrrol-1-yl)ethoxy]phenyl}-2-ethoxypropanoic acid and its pharmaceutically acceptable salts;
(±) 3-{4-[2-(2-ethyl-5-methylpyrrol-1-yl)ethoxy]phenyl}-2-ethoxypropanoic acid and its pharmaceuticaly acceptable salts;
(+) 3-{4-[2-(2-ethyl-5-methylpyrrol-1-yl)ethoxy]phenyl}-2-ethoxypropanoic acid and its pharmaceutically acceptable salts;
(−) 3-{4-[2-(2-ethyl-5-methylpyrrol-1-yl)ethoxy]phenyl}-2-ethoxypropanoic acid and its pharmaceutically acceptable salts;
(±) 3-{4-[2-(5-methyl-2-propylpyrrol-1-yl)ethoxy]phenyl}-2-ethoxypropanoic acid and its pharmaceutically acceptable salts;
(+) 3-{4-[2-(5-methyl-2-propylpyrrol-1-yl)ethoxy]phenyl}-2-ethoxypropanoic acid and its pharmaceutically acceptable salts;
(−) 3-{4-[2-(5-methyl-2-propylpyrrol-1-yl)ethoxy]phenyl}-2-ethoxypropanoic acid and its pharmaceutically acceptable salts;
(±) 3-{4-[2-(5-methyl-2-n-butylpyrrol-1-yl)ethoxy]phenyl}-2-ethoxypropanoic acid and its pharmaceutically acceptable salts;
(+) 3-{4-[2-(5-methyl-2-n-butylpyrrol-1-yl)ethoxy]phenyl}-2-ethoxypropanoic acid and its pharmaceutically acceptable salts;
(−) 3-{4-[2-(5-methyl-2-n-butylpyrrol-1-yl)ethoxy]phenyl}-2-ethoxypropanoic acid and its pharmaceutically acceptable salts;
(±) 3-{4-[2-(5-methyl-2-phenylpyrrol-1-yl)ethoxy]phenyl}-2-ethoxypropanoic acid and its pharmaceutically acceptable salts;
(+) 3-{4-[2-(5-methyl-2-phenylpyrrol-1-yl)ethoxy]phenyl}-2-ethoxypropanoic acid and its pharmaceutically acceptable salts;
(−) 3-{4-[2-(5-methyl-2-phenylpyrrol-1-yl)ethoxy]phenyl}-2-ethoxypropanoic acid and its pharmaceutically acceptable salts;
(±) 3-{4-[2-(5-methyl-2-phenylpyrrol-1-yl)ethoxy]phenyl}-2-ethoxypropanoic acid and its pharmaceutically acceptable salts;
(+) 3-{4-[2-(5-methyl-2-phenylpyrrol-1-yl)ethoxy]phenyl}-2-methoxypropanoic acid and its pharmaceutically acceptable salts;
(−) 3-{4-[2-(5-methyl-2-phenylpyrrol-1-yl)ethoxy]phenyl}-2-methoxypropanoic acid and its pharmaceutically acceptable salts;
(±) 3-{4-[2-(5-methyl-2-(4-methylphenyl)pyrrol-1-yl)ethoxy]phenyl)-2-propoxypropanoic acid and its pharmaceutically acceptable salts;
(+) 3-{4-[2-(5-methyl-2-(4-methylphenyl)pyrrol-1-yl)ethoxy]phenyl}-2-propoxypropanoic acid and its pharmaceutically acceptable salts;
(−) 3-{4-[2-(5-methyl-2-(4-methylphenyl)pyrrol-1-yl)ethoxy]phenyl}-2-propoxypropanoic acid and its pharmaceutically acceptable salts;
(±) 3-{4-[2-(5-methyl-3-phenylpyrrol-1-yl)ethoxy]phenyl}-2-ethoxypropanoic acid and its pharmaceutically acceptable salts;
(+) 3-{4-[2-(5-methyl-3-phenylpyrrol-1-yl)ethoxy]phenyl}-2-ethoxypropanoic acid and its pharmaceutically acceptable salts;
(−) 3-{4-[2-(5-methyl-3-phenylpyrrol-1-yl)ethoxy]phenyl}-2-ethoxypropanoic acid and its pharmaceutically acceptable salts;
(±) 3-{4-[2-(5-methyl-2-(4-methylphenyl)pyrrol-1-yl)ethoxy]phenyl}-2-ethoxypropanoic acid and its pharmaceutically acceptable salts;
(+) 3-{4-[2-(5-methyl-2-(4-methylphenyl)pyrrol-1-yl)ethoxy]phenyl}-2-ethoxypropanoic acid and its pharmaceutically acceptable salts;
(−) 3-{4-[2-(5-methyl-2-(4-methylphenyl)pyrrol-1-yl)ethoxy]phenyl}-2-ethoxypropanoic acid and its pharmaceutically acceptable salts;
(±) 3-{4-[2-(5-methyl-2-(3-methylphenyl)pyrrol-1-yl)ethoxy]phenyl}-2-ethoxypropanoic acid and its pharmaceutically acceptable salts;
(+) 3-{4-[2-(5-methyl-2-(3-methylphenyl)pyrrol-1-yl)ethoxy]phenyl}-2-ethoxypropanoic acid and its pharmaceutically acceptable salts;
(−) 3-{4-[2-(5-methyl-2-(3-methylphenyl)pyrrol-1-yl)ethoxy]phenyl}-2-ethoxypropanoic acid and its pharmaceutically acceptable salts;
(±) 3-{4-[2-(5-methyl-2-(2-methylphenyl)pyrrol-1-yl)ethoxy]phenyl}-2-ethoxypropanoic acid and its pharmaceutically acceptable salts;
(+) 3-{4-[2-(5-methyl-2-(2-methylphenyl)pyrrol-1-yl)ethoxy]phenyl}-2-ethoxypropanoic acid and its pharmaceutically acceptable salts;

(−) 3-{4-[2-(5-methyl-2-(2-methylphenyl)pyrrol-1-yl) ethoxy]phenyl}-2-ethoxypropanoic acid and its pharmaceutically acceptable salts;

(±) 3-{4-[2-5-methyl-2(4-methoxyphenyl)pyrrol-1-yl) ethoxy]phenyl}-2-ethoxypropanoic acid and its pharmaceutically acceptable salts;

(+) 3-{4-[2-(5-methyl-2-(4-methoxyphenyl)pyrrol-1-yl) ethoxy]phenyl}-2-ethoxypropanoic acid and its pharmaceutically acceptable salts;

(−) 3-{4-[2-(5-methyl-2-(4-methoxyphenyl)pyrrol-1-yl) ethoxy]phenyl}-2-ethoxypropanoic acid and its pharmaceutically acceptable salts;

(±) 3-{4-[2-5-methyl-2-(4-bromophenyl)pyrrol-1-yl) ethoxy]phenyl}-2-ethoxypropanoic acid and its pharmaceutically acceptable salts;

(+) 3-{4-[2-(5-methyl-2-(4-bromophenyl)pyrrol-1-yl) ethoxy]phenyl}-2-ethoxypropanoic acid and its pharmaceutically acceptable salts;

(−) 3-{4-[2-(5-methyl-2-(4-bromophenyl)pyrrol-1-yl) ethoxy]phenyl}-2-ethoxypropanoic acid and its pharmaceutically acceptable salts;

(±) 3-{4-[2-(5-methyl-2-(4-fluorophenyl)pyrrol-1-yl) ethoxy]phenyl}-2-ethoxypropanoic acid and its pharmaceutically acceptable salts;

(+) 3-{4-[2-(5-methyl-2-(4-fluorophenyl)pyrrol-1-yl) ethoxy]phenyl}-2-ethoxypropanoic acid and its pharmaceutically acceptable salts;

(−) 3-{4-[2-(5-methyl-2-(4-fluorophenyl)pyrrol-1-yl) ethoxy]phenyl}-2-ethoxypropanoic acid and its pharmaceutically acceptable salts;

(±) 3-{4-[2-(5-methyl-2-(4-chlorophenyl)pyrrol-1-yl) ethoxy]phenyl}-2-ethoxypropanoic acid and its pharmaceutically acceptable salts;

(+) 3-{4-[2-(5-methyl-2-(4-chlorophenyl)pyrrol-1-yl) ethoxy]phenyl}-2-ethoxypropanoic acid and its pharmaceutically acceptable salts;

(−) 3-{4-[2-(5-methyl-2-(4-chlorophenyl)pyrrol-1-yl) ethoxy]phenyl}-2-ethoxypropanoic acid and its pharmaceutically acceptable salts;

(±) 3-{4-[2-(4-methyl-2-phenylpyrrol-1-yl)ethoxy]phenyl}-2-ethoxypropanoic acid and its pharmaceutically acceptable salts;

(+) 3-{4-[2-(4-methyl-2-phenylpyrrol-1-yl)ethoxy]phenyl}-2-ethoxypropanoic acid and its pharmaceutically acceptable salts;

(−) 3-{4-[2-(4-methyl-2-phenylpyrrol-1-yl)ethoxy]phenyl}-2-ethoxypropanoic acid and its pharmaceutically acceptable salts;

(±) 3-{4-[2-(5-methyl-2,3-diphenylpyrrol-1-yl)ethoxy] phenyl}-2-ethoxypropanoic acid and its pharmaceutically acceptable salts;

(+) 3-{4-[2-(5-methyl-2,3-diphenylpyrrol-1-yl)ethoxy] phenyl}-2-ethoxypropanoic acid and its pharmaceutically acceptable salts;

(−) 3-{4-[2-(5-methyl-2,3-diphenylpyrrol-1-yl)ethoxy] phenyl}-2-ethoxypropanoic acid and its pharmaceutically acceptable salts;

(±) 3-{4-[2-(2-isopropyl-5-methylpyrrol-1-yl)ethoxy] phenyl}-2-ethoxypropanoic and its pharmaceutically acceptable salts;

(+) 3-{4-[2-(2-isopropyl-5-methylpyrrol-1-yl)ethoxy] phenyl}-2-ethoxypropanoic and its pharmaceutically acceptable salts;

(−) 3-{4-[2-(2-isopropyl-5-methylpyrrol-1-yl)ethoxy] phenyl}-2-ethoxypropanoic and its pharmaceutically acceptable salts;

(±) 3-{4-[2-(2,5-diisopropylpyrrol-1-yl)ethoxy]phenyl}-2-ethoxypropanoic acid and its pharmaceutically acceptable salts;

(+) 3-{4-[2-(2,5-diisopropylpyrrol-1-yl)ethoxy]phenyl}-2-ethoxypropanoic acid and its pharmaceutically acceptable salts;

(−) 3-{4-[2-(2,5-diisopropylpyrrol-1-yl)ethoxy]phenyl}-2-ethoxypropanoic acid and its pharmaceutically acceptable salts;

(±) 3-{4-[2-(5-isopropyl-2-phenylpyrrol-1-yl)ethoxy] phenyl}-2-ethoxypropanoic acid and its pharmaceutically acceptable salts;

(+) 3-{4-[2-(5-isopropyl-2-phenylpyrrol-1-yl)ethoxy] phenyl}-2-ethoxypropanoic acid and its pharmaceutically acceptable salts;

(−) 3-[4-[2-(5-isopropyl-2-phenylpyrrol-1-yl)ethoxy] phenyl}-2-ethoxypropanoic acid and its pharmaceutically acceptable salts;

(±) 3-{4-[2-(2,5-diisopropyl-3-phenylpyrrol-1-yl)ethoxy] phenyl}-2-ethoxypropanoic acid and its pharmaceutically acceptable salts;

(+) 3-{4-[2-(2,5-diisopropyl-3-phenylpyrrol-1-yl)ethoxy] phenyl}-2-ethoxypropanoic acid and its pharmaceutically acceptable salts;

(−) 3-{4-[2-(2,5-diisopropyl-3-phenylpyrrol-1-yl)ethoxy] phenyl}-2-ethoxypropanoic acid and its pharmaceutically acceptable salts;

(±) 3-(4-{2-[5-isopropyl-2-(4-methoxyphenyl)pyrrol-1-yl] ethoxy}phenyl)-2-ethoxypropanoic acid and its pharmaceutically acceptable salts;

(+) 3-(4-{2-[5-isopropyl-2-(4-methoxyphenyl)pyrrol-1-yl] ethoxy}phenyl)-2-ethoxypropanoic acid and its pharmaceutically acceptable salts;

(−) 3-(4-{2-[5-isopropyl-2-(4-methoxyphenyl)pyrrol-1-yl] ethoxy}phenyl)-2-ethoxypropanoic acid and its pharmaceutically acceptable salts;

(±) 3-(4-{2-[2-(4-fluorophenyl)-5-isopropylpyrrol-1-yl] ethoxy}phenyl)-2-ethoxypropanoic acid and its pharmaceutically acceptable salts;

(+) 3-(4-{2-[2-(4-fluorophenyl)-5-isopropylpyrrol-1-yl] ethoxy}phenyl)-2-ethoxypropanoic acid and its pharmaceutically acceptable salts;

(−) 3-(4-{2-[2-(4-fluorophenyl)-5-isopropylpyrrol-1-yl] ethoxy}phenyl)-2-ethoxypropanoic acid and its pharmaceutically acceptable salts;

(±) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(+) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(−) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(±) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(+) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(−) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(±) 3-(4-{2-[2-(4-fluorophenyl)-5-isopropyl-3-phenyl-4-phenylcarbamoylpyrrol-1-yl]ethoxy}phenyl)-2-ethoxypropanoic acid its pharmaceutically acceptable salts;

(+) 3-(4-{2-[2-(4-fluorophenyl)-5-isopropyl-3-phenyl-4-phenylcarbamoylpyrrol-1-yl]ethoxy}phenyl)-2-ethoxypropanoic acid and its pharmaceutically acceptable salts;

(−) 3-(4-{2-[2-(4-fluorophenyl)-5-isopropyl-3-phenyl-4-phenylcarbamoylpyrrol-1-yl]ethoxy}phenyl)-2-ethoxypropanoic acid and its pharmaceutically acceptable salts;

(±) 3-(4-{3-[2-(4-fluorophenyl)-5-isopropyl-3-phenyl-4-phenylcarbamoylpyrrol-1-yl]propoxy}phenyl)-2-ethoxypropanoic acid and its pharmaceutically acceptable salts;

(+)3-(4-{3-[2-(4-fluorophenyl)-5-isopropyl-3-phenyl-4-phenylcarbamoylpyrrol-1-yl]propoxy}phenyl)-2-ethoxypropanoic acid and its pharmaceutically acceptable salts;

(−)3-(4-{3-[2-(4-fluorophenyl)-5-isopropyl-3-phenyl-4-phenylcarbamoylpyrrol-1-yl]propoxy}phenyl)-2-ethoxypropanoic acid and its pharmaceutically acceptable salts;

(±) 3-(4-(2-[2-(4-fluorophenyl)-5-phenylpyrrol-1-yl]ethoxy)phenyl)-2-ethoxypropanoic acid and its pharmaceutically acceptable salts;

(+) 3-(4-{2-[2-(4-fluorophenyl)-5-phenylpyrrol-1-yl]ethoxy}phenyl)-2-ethoxypropanoic acid and its pharmaceutically acceptable salts;

(−) 3-(4-{2-[2-(4-fluorophenyl)-5-phenylpyrrol-1-yl]ethoxy}phenyl)-2-ethoxypropanoic acid and its pharmaceutically acceptable salts;

(±) 3-[4-[2-(3-carboxy-5-phenyl-2-(4-fluorophenyl)pyrrol-1-yl)ethoxy]phenyl]-2-ethoxypropanoic acid and its pharmaceutically acceptable salts;

(+) 3-[4-[2-(3-carboxy-5-phenyl-2-(4-fluorophenyl)pyrrol-1-yl)ethoxy]phenyl]-2-ethoxypropanoic acid and its pharmaceutically acceptable salts;

(−) 3-[4-[2-(3-carboxy-5-phenyl-2-(4-fluorophenyl)pyrrol-1-yl)ethoxy]phenyl]-2-ethoxypropanoic acid and its pharmaceutically acceptable salts;

(±) 3-{4-[2-(2-methylthiopyrrol-1-yl)ethoxy]phenyl}-2-ethoxypropanoic acid and its pharmaceutically acceptable salts;

(+) 3-{4-[2-(2-methylthiopyrrol-1-yl)ethoxy]phenyl}-2-ethoxypropanoic acid and its pharmaceutically acceptable salts;

(−) 3-{4-[2-(2-methylthiopyrrol-1-yl)ethoxy]phenyl}-2-ethoxypropanoic acid and its pharmaceutically acceptable salts;

(E/Z) 3-{4-[2-(5-methyl-2-phenylpyrrol-1-yl)ethoxy]phenyl}-2-ethoxyprop-2-enoic acid and its pharmaceutically acceptable salts;

(E) 3-{4-[2-(5-methyl-2-phenylpyrrol-1-yl)ethoxy]phenyl}-2-ethoxyprop-2-enoic acid and its pharmaceutically acceptable salts; and (Z) 3-{4-[2-(5-methyl-2-phenylpyrrol-1-yl)ethoxy]phenyl}-2-ethoxyprop-2-enoic acid and its pharmaceutically acceptable salts.

The present invention also provides methods for the preparation of novel compounds described in the general formula (I), their tautomeric forms, their derivatives, their analogs, their stereoisomers, their polymorphs, their pharmaceutically acceptable salts and their pharmaceutically acceptable solvates, wherein $R^1$, $R^2$, $R^3$, $R^4$, $R^5$, $R^6$, $R^7$, $R^8$, W, X, Y, Z, Ar and n are as defined earlier. These methods are described below, comprising:

Route 1:

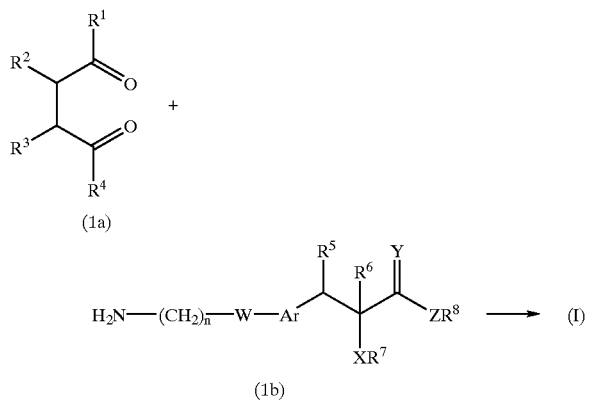

The reaction of a compound of general formula (1a), wherein all symbols are as defined earlier with a compound of formula (1b) which may be optically active or racemic, wherein all symbols are as defined earlier to yield a compound of general formula (I) may be carried out using Paal-Knorr cyclization (Paal C. Ber., 1885, 18, 367; Knorr, L., Ber., 1885, 18, 299). The reaction may be carried out neat or in the presence of a solvent or a mixture thereof such as tetrahydrofuran, hexane, toluene, methanol, ethanol, heptane, petroleum ether, xylene, benzene, ethyl acetate, tert-butyl acetate, 1,2-dichloroethane, iso-propanol, dioxane, cyclohexane, acetonitrile and the like. The reaction temperature may range from 0° C. to the reflux temperature of the solvent(s) used. The water produced may be removed by using a Dean Stark water separator or by water scavengers such as molecular sieves. The reaction may be carried out in the absence or presence of an inert atmosphere such as $N_2$, He or Ar. The reaction may be carried out under acidic condition provided by acids like acetic acid, propanoic acid, butyric acid, isobutyric acid, pivalic acid, p-toluenesulfonic acid, camphorsulfonic acid, benzenesulfonic acid, trifluoroacetic acid, chloroacetic acid, chloropropanoic acid, phenylacetic acid, phenylpropanoic acid, malonic acid, succinic acid, benzoic acid, halogenated benzoic acid, toluic acid and the like. Mineral acids such as HCl or HBr may also be used. The reaction time may range from 5 minutes to 72 hours, preferably from 1 to 48 hours.

Route 2:

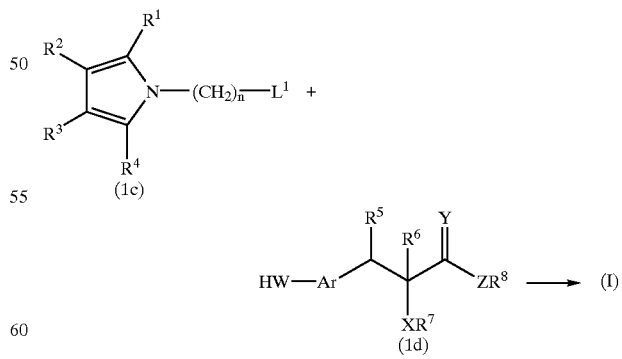

The reaction of compound of formula (1c), where all symbols are as defined earlier and $L^1$ represents a leaving group such as halogen atom, p-toluenesulfonate, methanesulfonate, trifluoromethanesulfonate and the like with a compound of formula (1d) which may be optically active or racemic, where W is either O or S and all other symbols are as defined earlier, to produce a compound of general formula (I). This reaction may be carried out in the presence of solvents, such as acetone, tetrahydrofuran, dimethylsulfoxide, dioxane, acetonitrile, dimethyl formamide, DME, benzene, toluene, pet. ether, heptane, hexane, 2-butanone, xylene, alcohols such as methanol, ethanol, propanol, butanol, iso-butanol, tert-butanol, pentanol and the like or a mixture thereof. Base such as alkali metal carbonate such as $K_2CO_3$, $Na_2CO_3$, $CsCO_3$, and the like; or alkali metal hydroxide such as NaOH, KOH and the like, may be used during this reaction. Alkali metal hydrides such as NaH, KH can be used whenever solvent employed does not contain protic or containing carbonyl group. The reaction may be carried out at a temperature in the range 0° C. to reflux temperature of the solvent(s) used and the reaction time may range from 1 to 48 hours.

Route 3:

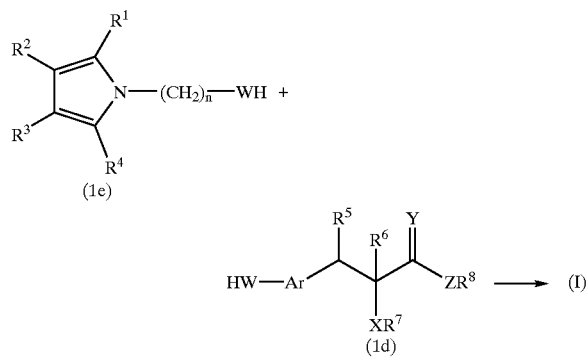

The reaction of compound of general formula (1e) where all symbols are as defined earlier and W represents oxygen atom, with a compound of general formula (1d) which may be optically active or racemic, where W is O or S and all other symbols are as defined earlier may be carried out using coupling agents such as DCC, EDC, triaryl phosphine/ dialkyl azadicarboxylate such as $PPh_3/DEAD$ or $PPh_3/DIAD$ and the like. Inert atmosphere may be maintained using $N_2$, Ar or He. Solvents such as tetrahydrofuran, dioxane, DME, toluene, dichloromethane, chloroform, carbon tetrachloride, acetonitrile and the like may be used. Compounds such as DMAP, HOBT may be used in the range of 0.05 to 2 equivalents. The reaction temperature in the range of 0° C. to reflux temperature of the solvent may be used, preferably, 20° C. to 80° C. The duration of the reaction may range from 0.5 to 24 h, preferably 0.5 to 12 hours.

Route 4:

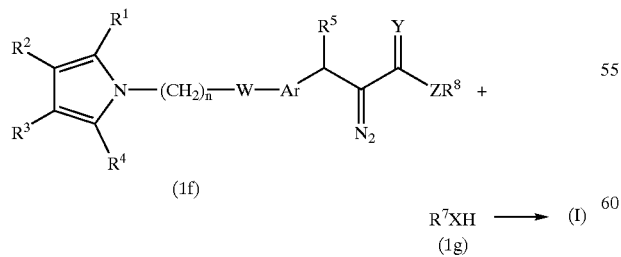

The reaction of a compound of formula (1f) where all symbols are as defined earlier with an alcohol of formula (1g) where $R^7$ is as defined earlier, to produce a compound of formula (I) where all symbols are as defined earlier, may be carried out in the presence of rhodium salts such as rhodium (II) acetate. Solvents such as benzene, toluene, ether, THF, dioxane and the like may be used. $R^7XH$ may also be used as solvent to enhance the rate of the reaction. Inert atmosphere may be maintained using $N_2$, Ar or He. The reaction time may range from 0.25 to 48 hours, preferably 0.25 h to 8 h.

Route 5:

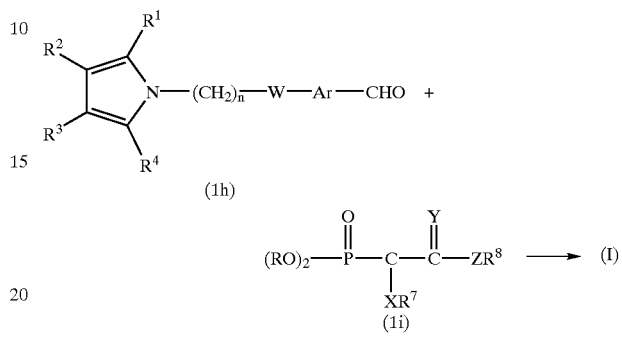

The reaction of a compound of general formula (1h) wherein all the symbols are as defined earlier, with a compound of formula (1i), where all the symbols are as defined earlier and R represents $(C_1-C_8)$ alkyl to afford a compound of formula (I) where $R^5$ and $R^6$ represent a bond and all other symbols are as defined earlier, may be carried out under Wittig Homer reaction conditions in the presence of a base such as alkali metal hydrides, like NaH or KH, alkali metal alkoxides such as NaOMe, NaOEt, $K^+$ t-BuO$^-$ or mixture thereof, organolithiums like $CH_3Li$, BuLi, sec-BuLi, LDA and the like. Aprotic solvents such as THF, dioxane, DMF, DMSO, DME and the like or mixture thereof may be employed. HMPA favours the progression of the reaction but not essential. The reaction may be carried out at a temperature ranging from −80° C. to 100° C., preferably from 0° C. to 30° C. The reaction proceeds more effectively under anhydrous and inert conditions.

The compound of formula. (I) where $R^5$ and $R^6$ represent a bond may be reduced to a compound of general formula (I) where $R^5$ and $R^6$ each represent hydrogen atom by reacting with hydrogen gas in the presence of a catalyst such as 5–10% Pd/C, Rh/C, Pt/C Raney Ni and the like, 5–100% w/w of the catalyst may be employed or the mixture thereof. The pressure of hydrogen gas may be one atmosphere to 80 psi. Suitable solvents are alcohols such as ethanol, methanol and the like, ethyl acetate, THF, dioxane, acetic acid and the like. Temperature may be in the range of 20° C. to 80° C., may be used for this reduction process. Metal-solvent such as magnesium in alcohol or sodium amalgam in alcohol may also be used, for this reduction process.

According to a feature of the present invention, there is provided an intermediate of formula (1h),

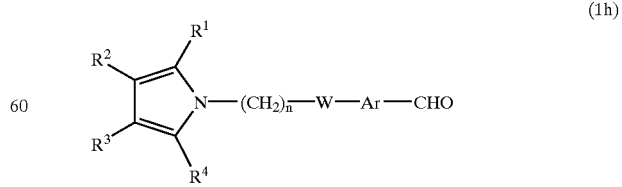

wherein one or more groups $R^1$, $R^2$, $R^3$, $R^4$ may be same or different and represent hydrogen, halogen, perhaloalkyl, hydroxy, thio, amino, nitro, cyano, formyl, amidino, guanidino, substituted or unsubstituted groups selected from linear or branched ($C_1$–$C_{12}$)alkyl, linear or branched ($C_2$–$C_{12}$)alkenyl, ($C_3$–$C_7$)cycloalkyl, ($C_3$–$C_7$)cycloalkenyl, bicycloalkyl, bicycloalkenyl, ($C_1$–$C_{12}$)alkoxy, cyclo($C_3$–$C_7$) alkoxy, aryl, aryloxy, aralkyl, aralkoxy, heterocyclyl, heteroaryl, heterocyclyl($C_1$–$C_{12}$)alkyl, heteroaralkyl, heteroaryloxy, heteroaralkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, arylthio, alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and its derivatives, sulfonic acid and its derivatives, phosphonic acid and its derivatives; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, alkyl or aryl; Ar represents a substituted or unsubstituted divalent single or fused aromatic, heteroaromatic or heterocyclic group.

According to another feature of the present invention, there is provided a process for the preparation of intermediate of the general formula (1h) as defined earlier which comprises reacting a compound of general formula (1c),

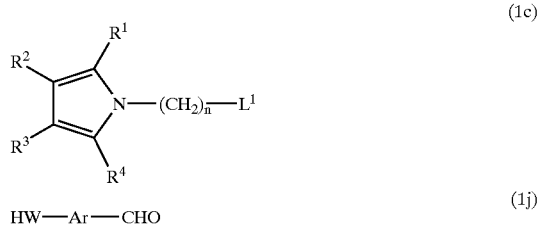

wherein, $R^1$—$R^4$, n are as defined earlier and $L^1$ is a halogen atom such as chlorine, bromine or iodine or a leaving group such as methanesulfonate, trifluoromethanesulfonate, p-toluenesulfonate and the like with the compound of the formula (1j), where Ar and W are as defined earlier.

The reaction of the compound of formula (1c) with the compound of formula (1j) to produce a compound of formula (1h) may be carried out in the presence of solvents such as acetone, THF, DMSO, dioxane, 2-butanone, acetonitrile, DMF, DME, benzene, toluene, xylene, alcohols such as methanol, ethanol, propanol, butanol, iso-butanol, tert-butanol, pentanol and the like or a mixture thereof. Bases such as alkali metal carbonates such as $K_2CO_3$, $Na_2CO_3$, $CsCO_3$ and the like may be used; alkali metal hydroxides like NaOH, KOH, and the like; or mixtures thereof may be used. Alkali metal hydrides such as NaH, KH and the like, may be used incases when the solvent used not protic and does not contain carbonyl group. The reaction temperature may range from 20° C. to reflux temperature of the solvent(s) used and the reaction time may range from 1 to 48 hours. The inert atmosphere may be maintained by using inert gases such as $N_2$, Ar or He.

Alternatively, the intermediate of the general formula (1h), can also be prepared by the reaction of compound of general formula (1e),

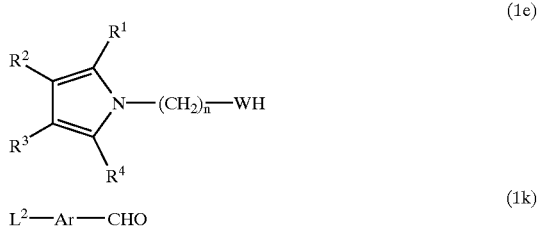

wherein $R^1$–$R^4$, n and W are as defined earlier and with a compound of the formula (1k), where Ar is as defined earlier and $L^2$ is a halogen atom such as fluorine, chlorine, bromine or iodine. The reaction of the compound of formula (1e) with the compound of formula (1k) to produce a compound of formula (1h) may be carried out in the presence of solvents such as THF, DMF, DMSO, DME and the like. Mixture of solvents may be used. The inert atmosphere may be maintained by using inert gases such as $N_2$, Ar or He. The reaction may be effected in the presence of a base such as $K_2CO_3$, $Na_2CO_3$, NaH or mixtures thereof. The reaction temperature may range from 20° C. to 150° C., preferably at a temperature in the range from 30° C. to 100° C. The duration of reaction may range from 1 to 24 hours, preferably from 2 to 6 hours.

The reaction of compound of general formula (1e) wherein W represents O and all other symbols are as defined earlier with the compound of formula (1j) may be carried out using suitable coupling agents such as dicyclohexyl urea, triarylphosphine/dialylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar or He. The reaction may be effected in the presence of DMAP, HOBT and they must be used in the range of 0.05 to 2 equivalents, preferably 0.25 to 1 equivalents. The reaction temperature may range from 0° C. to 100° C., preferably at a temperature in the range from 20° C. to 80° C. the duration of reaction of the reaction may range from 0.5 to 24 hours, preferably from 6 to 12 hours.

In another embodiment of this invention, there is provided a process for the preparation of a , compound of the general formula (1c), which comprises reacting the compound of general formula (1a) wherein $R^1$–$R^4$ are as defined earlier,

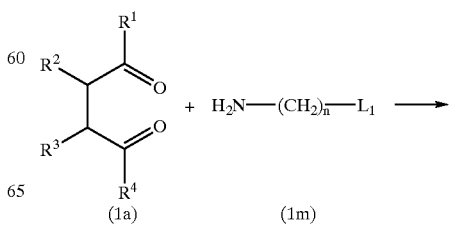

-continued

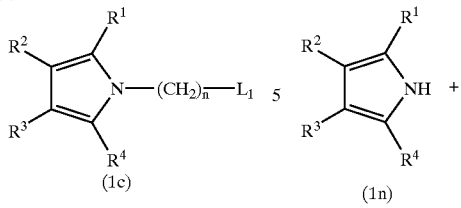

with either substituted amino compound (1m), where all symbols are is as defined earlier, to yield the intermediate of the general formula (1c).

In yet another embodiment of this invention, there is provided a process for the preparation of a compound of the general formula (1e), which comprises reacting the compound of general formula (1a) wherein $R^1$–$R^4$ are as defined earlier,

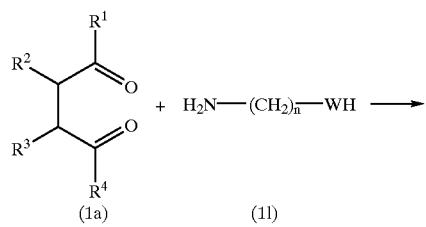

with either substituted amino compound (1l), where all symbols are is as defined earlier, to yield the intermediate of the general formula (1e).

The reactions of a compound of general formula (1a) with a compound of general formula (1l) or a compound of general formula (1m) may be carried out neat or in presence of solvents or a mixture thereof such as tetrahydrofuran, hexane, toluene, methanol, ethanol, heptane, petroleum ether, xylene, benzene, ethyl acetate, tert-butyl acetate, 1,2-dichloroethane, iso-propanol, tert-butanol, dioxane, cyclohexane, acetonitrile and the like. The reaction temperature may range from 0° C. to the reflux temperature of the solvent(s) used. The water produced may be removed by using a Dean Stark water separator or by water scavengers such as molecular sieves. The reaction may be carried out in the presence of an inert atmosphere such as $N_2$, He or Ar. The reaction may be carried out in the presence of an acid, such as acetic acid, propanoic acid, butyric acid, isobutyric acid, pivalic acid, p-toluenesulfonic acid, camphorsulfonic acid, benzenesulfonic acid, trifluoroacetic acid, chloroacetic acid, chloropropanoic acid, phenylacetic acid, phenylpropanoic acid, malonic acid, succinic acid, benzoic acid, halogenated benzoic acid, toluic acid and the like.

Yet another embodiment of this invention, there is provided an alternate process for the preparation of a compound of the general formula (1c), which comprises reacting the compound of general formula (1n) wherein $R^1$–$R^4$ are as defined earlier,

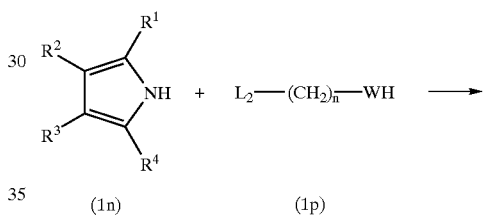

with the compound of formula (1o) where $L_1$ and $L_2$ may be same or different and represent leaving groups such as halogen atom as Cl, Br, or I, methanesulfonate, p-toluenesulfonate and the like; and n as defined earlier.

In yet another embodiment of this invention, there is provided an alternate process for the preparation of a compound of the general formula (1e), which comprises reacting the compound of general formula (1n) where $R^1$–$R^4$ are as defined earlier, with the compound of formula (1p) where $L_2$ represent leaving groups such as halogen atom as Cl, Br, or I, methanesulfonate, p-toluenesulfonate and the like; and n as defined earlier.

The reaction of compound of general formula (1n), with either (1o) or (1p) may be carried out in solvents such as alcohol like methanol, ethanol, iso-propanol and the like; THF, dioxane, DMSO, DMF, acetonitrile, heptane, benzene, toluene, xylene and the like. The reaction may be carried out in presence of bases such as NaH, KH, $Na_2CO_3$, $K_2CO_3$, NaOH, KOH, $LiNH_2$, $NaNH_2$ and the like. Phase transfer catalyst such as tetrabutyl ammonium halide, tetrabutyl ammonium hydroxide (TBAH) and the like may be used. The reaction temperature may range from 0° C. to the reflux temperature of the solvent employed. The reaction may be carried out in the presence of an inert atmosphere such as $N_2$, He or Ar.

In another embodiment of this invention, there is provided a process for the preparation of a compound of the general formula (1e), wherein $R^1$–$R^4$ and n are as defined earlier and W represents O, which comprises reducing the corresponding acid

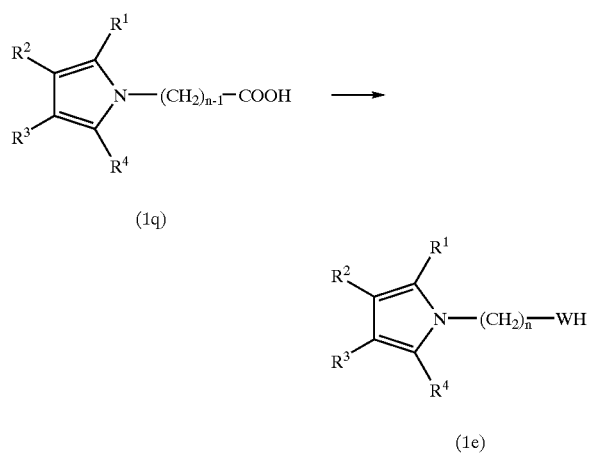

(1q)

(1e)

The reduction of compound of general formula (1q) may be carried out in presence of solvents or a mixture thereof such as tetrahydrofuran, dioxane, ether and the like. The reaction temperature may range from 0° C. to the reflux temperature of the solvent(s) used. The reaction may be carried out in the presence of an inert atmosphere such as $N_2$, He or Ar. Suitable reducing agent such as sodium borohydride/iodine, diborane and its derivative, $LiAl_4$ and the like may be used.

The compound of general formula (1q) may be prepared by the reaction of compound of general formula (1n) with a compound of $L_1(CH_2)_{n-1}COOR$, where $L_1$ and R are as defined earlier, followed by hydrolysis of the ester group to acid using methods commonly used.

Another feature of the present invention, is to provide an intermediate of formula (1f) wherein $R^1$, $R^2$, $R^3$, $R^4$, $R^5$, $R^8$, W, Z, n and Ar are as defined earlier.

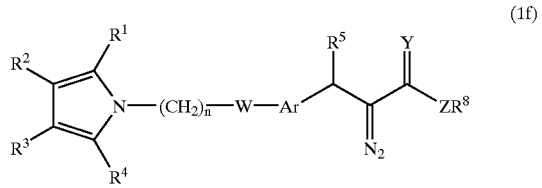

(1f)

wherein one or more groups $R^1$, $R^2$, $R^3$, $R^4$ may be same or different and represent hydrogen, halogen, perhaloalkyl, hydroxy, thio, amino, nitro, cyano, formyl, amidino, guanidino, substituted or unsubstituted groups selected from linear or branched $(C_1$–$C_{12})$alkyl, linear or branched $(C_2$–$C_{12})$alkenyl, $(C_3$–$C_7)$cycloalkyl, $(C_3$–$C_7)$cycloalkenyl, bicycloalkyl, bicycloalkenyl, $(C_1$–$C_{12})$alkoxy, cyclo$(C_3$–$C_7)$ alkoxy, aryl, aryloxy, aralkyl, ar$(C_1$–$C_{12})$alkoxy, heterocyclyl, heteroaryl, heterocyclyl$(C_3$–$C_7)$alkyl, heteroar $(C_1$–$C_{12})$alkyl, heteroaryloxy, heteroar$(C_1$–$C_{12})$alkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, aminoalkyl, monoalkylaminoalkyl, dialkylaminoalkyl, alkoxyalkyl, aryloxyalkyl, aralkoxyalkyl, $(C_1$–$C_{12})$alkylthio, thio $(C_1$–$C_{12})$alkyl, arylthio, $(C_1$–$C_{12})$alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and its derivatives, sulfonic acid and its derivatives, phosphonic acid and its derivatives; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, $(C_1$–$C_{12})$alkyl or aryl; Ar represents a substituted or unsubstituted divalent single or fused aromatic, heteroaromatic or heterocyclic group; $R^5$ represent hydrogen or a hydroxy, $(C_1$–$C_{12})$alkyl, $(C_1$–$C_{12})$ alkoxy, halogen, acyl, substituted or unsubstituted aralkyl group; Y represents O or S; Z represents oxygen, sulfur or $NR^{10}$, where $R^{10}$ represents hydrogen or substituted or unsubstituted groups selected from $(C_1$–$C_{12})$alkyl, aryl, ar$(C_1$–$C_{12})$alkyl, hydroxy$(C_1$–$C_{12})$alkyl, amino$(C_1$–$C_{12})$ alkyl, heteroaryl, heteroar$(C_1$–$C_{12})$alkyl groups; $R^8$ represents hydrogen, substituted or unsubstituted groups selected from $(C_1$–$C_{12})$alkyl, aryl, ar$(C_1$–$C_{12})$alkyl, heteroaryl, heteroar$(C_1$–$C_{12})$alkyl, heterocyclyl, heterocyclylalkyl, hydroxyalkyl, alkoxyalkyl, alkylaminoalkyl groups; $R^{10}$ and $R^8$ together may form a 5 or 6 membered substituted or unsubstituted cyclic ring structure containing carbon atoms or containing one or more heteroatoms selected from O, N and S, and a process for its preparation and its use in the preparation of β-aryl-α-substituted alkanoic acid derivatives.

The compound of formula (1f) where all the symbols are as defined earlier may be prepared by reacting a compound of formula (1r)

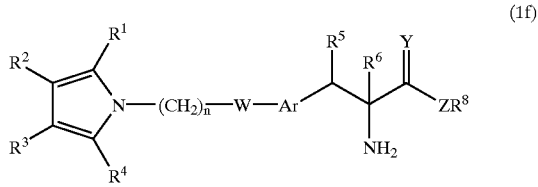

(1r)

where $R^6$ is hydrogen atom and all other symbols are as defined earlier, with an appropriate diazotizing agent.

The diazotization reaction may be under conventional conditions. A suitable diazotizing agent is an alkyl nitrile such as iso-amyl nitrile, amyl nitrite and the like. The reaction may be carried out in presence of solvents such as THF, dioxane, DMSO, DMF, acetonitrile, heptane, benzene, toluene, xylene and the like or the combination thereof. The reaction temperature may carried out in an inert atmosphere which may be maintained by using inert gases such as $N_2$, He or Ar. Temperature is in the range of –50° C. to 60° C. the duration of the reaction may range from 1 to 24 hr, preferably 1 to 12 hr.

The compound of formula (1r) where all the symbols are as defined earlier may also be prepared by reaction between (1c) where all symbols are as defined earlier and a compound of formula (1s),

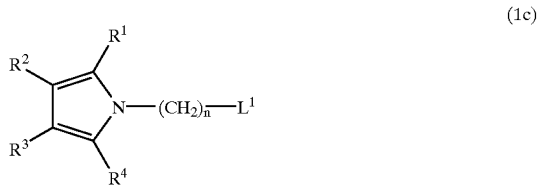

(1c)

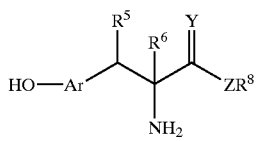
(1s)

where $R^6$ is hydrogen atom and all other symbols are as defined earlier.

The reaction of compound of general formula (1c), with (1s) may be carried out in solvents such as alcohol like methanol, ethanol, iso-propanol and the like; THIF, dioxane, DMSO, DMF, acetonitrile, heptane, benzene, toluene, xylene and the like. The reaction may be carried out in presence of bases such as NaOH, KOH, $K_2CO_3$, $Na_2CO_3$, $LiNH_2$ $NaNH_2NaH$, KH, $CsCO_3$ and the like. Acetone may be used as a solvent when $K_2CO_3$ or $Na_2CO_3$ is used as a base. The reaction temperature may range from 10° C. to the reflux temperature of the solvent employed. The duration of the reaction may be from 1 to 24 hrs, preferably from 3 to 12 hrs. The reaction may be carried out in the presence of an inert atmosphere such as $N_2$, He or Ar.

The compounds of the present invention may have asymmetric centers and occur either as racemates or racemic mixtures as well as individual diastereomers of any of the possible isomers, including optical isomers, being included in the present invention The stereoisomers of the compounds of the present invention may be prepared by one or more ways presented below:

i. One or more of the reagents may be used in their single isomeric form. For example, compound (1b) or (1d) may be pure stereoisomers.
ii. Optically pure catalysts or chiral ligands along with metal catalysts may be employed in the reduction process. The metal catalyst may be Rhodium, Ruthenium, Indium and the like. The chiral ligands may preferably be chiral phosphines. (Principles of Asymmetric synthesis J E Baldwin Ed. Tetrahedron series, Volume 14, Page no. 311–316)
iii. Mixture of stereoisomers may be resolved by conventional methods such as microbial resolution, resolving the diastereomeric salts formed with chiral acids or chiral bases. Chiral acids may be tartaric acid, mandelic acid, lactic acid, camphorsulfonic acid, amino acids and the like. Chiral bases may be cinchona alkaloids, (+) or (−) brucine, α-methyl benzylamine, (+) or (−) phenyl glycinol, ephedrine, amino sugars such as glucosamines or a basic amino acid such as lysine, arginine and the like.
iv. Resolution of the mixture of stereoisomers may also be effected by chemical methods by derivatization of the compound with a chiral compound such as chiral amines, chiral acids, chiral amino alcohols, amino acids into a 1:1 mixture of diastereomers and the diastereomers may be separated by conventional methods of fractional crystallization, chromatography and the like followed by cleaving the derivative (Jaques et al. "Enantiomers, Racemates and Resolution", Wiley Interscience, 1981; R. A. Sheldon, in "Chirotechnology", Marcel Dekker, Inc. NY, Basel, 1993, 173–204 and references therein; A. N. Collins, G. N. Sheldrack and J Crosby, in "Chirality in Industry II", John Wiley & Sons, Inc, 1997, 81–98 and references therein; E. L. Eliel and S. H. Wilen, in "Stereochemistry of Organic Compound", John Wiley & Sons, Inc, 1999, 297–464 and references therein.)

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal in such protecting groups are those conventional methods appropriate to the molecule being protected. T. W. Greene and P. G. M. Wuts "Protective groups in Organic Synthesis", John Wiley & Sons, Inc, 1999, $3^{rd}$ Ed., 201–245 along with references therein.

It will be appreciated that the above-mentioned preparation of the compounds of Formula (I), or a pharmaceutically acceptable salt thereof, and/or pharmaceutically acceptable solvate thereof is a stereoselective procedure and that the compound of formula (I) is a single stereoisomer. Favorably, a compound of formula (I) is present in admixture with less than 50% w/w of its racemic isomer, suitably 80–100% and preferably 90–100% pure, such as 90–95%, most preferably 95–100%, for example 95%, 96%, 97%, 98%, 99% and 99.99% optically pure.

Preferably the compounds of Formula (I), or a pharmaceutically acceptable salt thereof, and/or pharmaceutically acceptable solvate thereof is in optically pure form.

The absolute stereochemistry of the compounds may be determined using conventional methods, such as X-ray crystallography.

The pharmaceutically acceptable salts forming a part of this invention may be prepared by treating the compound of formula (I) with 1–6 equivalents of a base such as sodium hydride, sodium methoxide, sodium ethoxide, sodium hydroxide, potassium tert-butoxide, calcium hydroxide, calcium acetate, calcium chloride, magnesium hydroxide, magnesium chloride, magnesium alkoxide and the like. Solvents such as water, acetone, ether, THF, methanol, ethanol, t-butanol, 2-butanone, dioxane, propanol, butanol, isopropanol, diisopropyl ether, tert-butyl ether or mixtures thereof may be used. Organic bases such as lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfiric acid, nitric acid and the like in solvents such as water, alcohols, ethers, ethyl acetate, dioxane, THF, acetonitrile, DMF or a lower alkyl ketone such as acetone, or mixtures thereof.

Different polymorphs may by prepared by crystallization of compound of formula (I) under different conditions such as different solvents or solvent mixtures in varying proportions for recrystallization, various ways of crystallization such as slow cooling, fast cooling or a very fast cooling or a gradual cooling during crystallization. Different polymorphs may also be obtained by heating the compound, melting the compound and solidification by gradual or fast cooling, heating or melting under vacuum or under inert atmosphere, and cooling under either vacuum or inert atmosphere. The various polymorphs may be identified by differential scanning calorimeter, powder X-ray diffraction, IR spectroscopy or solid probe $^{13}C$ NMR spectroscopy.

Another aspect of the present invention comprises a pharmaceutical composition, containing at least one of the compounds of the general formula (I), their derivatives, their analogs, their tautomeric forms, their stereoisomers, their polymorphs, their pharmaceutically acceptable salts, their pharmaceutically acceptable solvates thereof as an active ingredient, together with pharmaceutically employed carriers diluents and the like.

Pharmaceutical compositions containing a compound of the present invention may be prepared by conventional techniques, e.g. as described in Remington: the Science and Practice of Pharmacy, 19$^{th}$ Ed., 1995. The compositions may be in the conventional forms, such as capsules, tablets, powders, solutions, suspensions, syrups, aerosols or topical applications. They may contain suitable solid or liquid carriers or in suitable sterile media to form injectable solutions or suspensions. The compositions may contain 0.5 to 20%, preferably 0.5 to 10% by weight of the active compound, the remaining being pharmaceutically acceptable carriers, excipients, diluents, solvents and the like.

Typical compositions containing a compound of formula (I) or a pharmaceutically acceptable acid addition salt thereof, associated with a pharmaceutically acceptable excipients which may be a carrier or a diluent or be diluted by a carrier, or enclosed within a carrier which can be in the form of a capsule, sachet, paper or other container. When the carrier serves as a diluent, it may be a solid, semi-solid, or liquid material, which acts as a vehicle, excipients or medium for the active compound. The active compound can be absorbed on a granular solid container for example in a sachet. Some of suitable carriers are water, salt solutions, alcohols, polyethylene glycols, polyhydroxyethoxylated castor oil, peanut oil, olive oil, gelatin, lactose, terra alba, sucrose, cyclodextrin, amylose, magnesium sterate, talc, gelatin, agar, pectin, acacia, stearic acid or lower alkyl ethers of cellulose, silicic acid, fatty acids, fatty acid amines, fatty acids monoglycerides and diglycerides, pentaerythritol fatty acids esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preservatives, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, buffers and/or coloring substances and the like, which do not deleteriously react with the active compounds.

The route of administration may be any route, which effectively transports the active drug to the appropriate or desired site of action effectively, such as oral, nasal, transdermal, pulmonary or parental e.g. rectal, depot, subcutaneous, intravenous, intraurethral, intramuscular, intranasal, ophthalmic solution or an ointment, preferably through oral route.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula (I) dissolved or suspended in a liquid carrier, in particular an aqueous carrier, for aerosol application. The carrier may contain additives such as solubilizing agent, e.g. propylene glycol, surfactants, absorption enhancers such as lecithin (phosphatidylcholine) or cyclodextrin, or preservatives such as parabens.

For parental application, particularly suitable are injectable solutions or suspensions, preferably aqueous solutions with the active compound dissolved in polyhydroxylated castor oil.

Tablet, dragees or capsules having talc and/or a carbohydrate carrier or binder or the like are particularly suitable for oral application. Preferably, carriers for tablets, dragees or capsules include lactose corn starch and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5.0 mg |
| Colloidal silicon dioxide (Aerosil) | 1.5 mg |
| Cellulose, misrocrytalline (Avicel) | 70.0 mg |
| Modified cellulose gum (Ac-Di-Sol) | 7.5 mg |
| Magnesium sterate | ad. |
| Coating: | |
| HPMC approx | 9.0 mg |
| *Mywacett 9-40 T approx. | 0.9 mg |

*Acylated monoglyceride used as plasticizer for film coating.

The compounds of general formula (I) or the compositions thereof are useful for the treatment and/or prophylaxis of disease caused by metabolic disorders such as hyperlipidemia, insulin resistance, Leptin resistance, hyperglycemia, obesity, or inflammation.

These compounds are useful for the treatment of hypercholesteremia, familial hypercholesteremia, hypertriglyceridemia, type 2 diabetes, dyslipidemia, disorders related to syndrome X such as hypertension, obesity, insulin resistance, coronary heart disease, atherosclerosis, xanthoma, stroke, peripheral vascular diseases and related disorders, diabetic complications, certain renal diseases such as glomerulonephritis, glomerulosclerosis, nephrotic syndrome, hypertensive nephrosclerosis, retinopathy, nephropathy, psoriasis, polycystic ovarian syndrome, osteoporosis, inflammatory bowel diseases, myotonic dystrophy, arteriosclerosis, Xanthoma, pancreatitis and for the treatment of cancer.

The compounds of the invention may be administered to a mammal, especially, a human in need of such treatment, prevention, elimination, alleviation or amelioration of diseases mentioned above.

The compounds of the present invention are effective over a wide dosage range, however, the exact dosage, mode of administration and form of composition depends upon the subject to be treated and is determined by the physician or veterinarian responsible for treating the subject. Generally, dosages from about 0.025 to about 200 mg preferably from about 0.1 to about 100 mg, per day may be used. Generally, the unit dosage form comprises about 0.01 to 100 mg of the compound of formula (I), as an active ingredient together with a pharmaceutically acceptable carrier. Usually suitable dosage forms for nasal, oral, transdermal or pulmonary administration comprises from about 0.001 mg to about 100 mg, preferably from 0.01 mg to about 50 mg of the active ingredient mixed with a pharmaceutically acceptable carrier or diluent.

In another aspect of the present invention, method of treatment and/or prevention of the diseases mentioned above are provided.

In a further aspect of the present invention, use of one or more compounds of the general formula (I) or pharmaceutically acceptable salts, for the preparation of a medicament thereof for the treatment and/or prevention of diseases mentioned in this document is provided.

In still further aspect of the present invention use of the compounds of the present invention alone or in combination with statins, glitazones, biguamides, angiotensin II inhibitors, aspirin, insulin secretagogue, β-sitosterol inhibitor, sulfonylureas, insulin, fibric acid derivatives, nicotinic acid, cholestyramine, cholestipol or probucol, α-glycosidase inhibitors or antioxidants, which may be administered together or within such a period as to act synergistically together.

The invention is explained in detail by the examples given below, which are provided by way of illustration only and therefore should not be consumed to limit the scope of the invention.

Preparation 1

Preparation of 1-(2-hydroxyethyl)-2,5-dimethyl-1H-pyrrole (Compound No. 1)

(Compound No. 1)

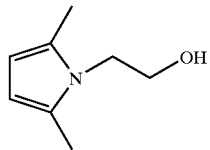

A mixture of hexan-2,5-dione (5 g), ethanol amine (26.7 g) and pivalic acid (23.26 g) in a solvent mixture containing n-heptane: tetrahydrofuran: toluene (4:1:1, 50 mL) was refluxed with stirring at 110–120° C. Water formed during the reaction was removed azeotropically during 3 to 4 hrs. The reaction mixture was cooled and the solvent was removed. The residue obtained was dissolved in dichloromethane (30 mL), washed with saturated sodium bicarbonate solution (30 mL), water (30 mL), and then with brine (30 mL), dried ($Na_2SO_4$) and the solvent was evaporated. The crude compound obtained as an oily mass, was purified by column chromatography (silica gel 100–200), using ethyl acetate:hexane (2:8) as an eluent to obtain the title compound.

In the like manner to that described in Preparation 1, the following compounds of general formula (1e) were prepared from the appropriately substituted diketones as mentioned in Table 1. The latter can be synthesized by using various routes found in literature.

TABLE 1

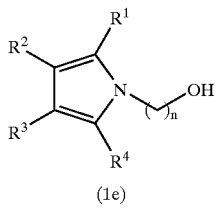

(1e)

| Comp. No. | Substituents on the pyrrole ring in (1e) | | | | | Mol. Wt. (mp ° C.) | Yield (% w/w) | $^1$H NMR (300 MHz, δ, $CDCl_3$) |
|---|---|---|---|---|---|---|---|---|
| | $R^1$ | $R^2$ | $R^3$ | $R^4$ | n = | | | |
| 1. | $CH_3$ | H | H | $CH_3$ | 2 | 139 | 65 | 2.21 (6H, s); 3.70–3.72 (2H, m); 3.89 (2H, t, J=5.8 Hz); 5.76 (2H, s). |
| 2. | $CH_3$ | H | H | $CH_2CH_3$ | 2 | 153 | 53 | 1.26(3H, t, J=7.4 Hz); 2.22 (3H, s); 2.56 (2H, q, J=7.4 Hz); 3.71 (2H, t, J=5.86 Hz); 3.88 (2H, t, J=5.89 Hz); 5.79–5.81 (2H, m). |
| 3. | $CH_3$ | H | H | $(CH_2)_2CH_3$ | 2 | 167 | 36 | 1.02(3H, t, J=7 Hz); 1.65 (2H, m); 2.25 (3H, s); 2.5 (2H, t, J=7.7 Hz); 4.1 (2H, t, J=5.9 Hz); 4.35 (2H, t, J=5.9 Hz); 5.8–5.82 (2H, m). |
| 4. | $CH_3$ | H | H | $(CH_2)_3CH_3$ | 2 | 181 | 58 | 0.94(3H, t, J=7.2 Hz); 1.36–1.4 (2H, m); 1.58–1.67 (2H, m); 2.22 (3H, s); 2.53 (2H, t, J=7.7 Hz); 3.7 (2H, t, J=5.8 Hz); 3.89 (2H, t, J=5.8 Hz); 5.7–5.8 (2H, m). |

TABLE 1-continued

Structure (1e): Pyrrole ring with substituents R¹, R², R³, R⁴ and N-(CH₂)ₙ-OH group.

| Comp. No. | Substituents on the pyrrole ring in (1e) | | | | n = | Mol. Wt. (mp °C.) | Yield (% w/w) | ¹H NMR (300 MHz, δ, CDCl₃) |
|---|---|---|---|---|---|---|---|---|
| | R¹ | R² | R³ | R⁴ | | | | |
| 5. | CH₃ | H | H | phenyl | 2 | 201 | 62 | 2.33 (3H, s); 3.5–3.6 (2H, t, J=5.9 Hz); 4.05–4.09 (2H, t, J=6.0 Hz); 5.95 (1H, d, J=3.3 Hz); 6.09 (1H, d, J=3.3 Hz); 7.25–7.29 (1H, m); 7.30–7.38 (4H, m). |
| 6. | CH₃ | H | H | 4-methylphenyl (H₃C-) | 2 | 215 | 55 | 2.32 (3H, s); 2.37 (3H, s); 3.59 (2H, t, J=6.9 Hz); 4.10 (2H, t, J=6.9 Hz), 5.94 (1H, d, J=3.36 Hz), 6.0 (1H, d, J=3.36 Hz), 7.2 (2H, d, J=8.5 Hz); 7.25 (2H, d, J=8.5 Hz) |
| 7. | CH₃ | H | H | 3-methylphenyl (-CH₃) | 2 | 215 | 60 | 2.32 (3H, s); 2.36 (3H, s); 3.57 (2H, t, J=6 Hz); 4.08 (2H, t, J=6.06 Hz); 5.94 (1H, d, J=2.28 Hz); 6.1 (1H, d, J=3.39 Hz); 7.09–7.3 (4H, m). |
| 8. | CH₃ | H | H | 2-methylphenyl (-CH₃) | 2 | 215 | 60 | 2.32 (3H, s); 2.36 (3H, s); 3.58 (2H, t, J=6 Hz); 4.07 (2H, t, J=6.06 Hz); 5.94 (1H, d, J=2.28 Hz); 6.07 (1H, d, J=3.39 Hz); 7.09–7.15 (2H, m); 7.24–7.29 (2H, m). |
| 9. | CH₃ | H | H | 4-methoxyphenyl (H₃CO-) | 2 | 231 | 45 | 2.3 (1H, s); 3.53 (2H, t, J=6.9 Hz); 3.84 (3H, s); 4.0 (2H, t, J=6.9 Hz); 5.9 (1H, d, J=3.36 Hz); 6.0 (1H, d, J=3.36 Hz); 6.95 (2H, d, J=6.78 Hz); 7.2 (2H, d, J=6.78 Hz). |
| 10. | CH₃ | H | H | 4-bromophenyl (Br-) | 2 | 280 | 55 | 2.32 (3H, s); 3.61–3.63 (2H, m) 4.05 (3H, t, J=6.2 Hz); 5.95 (1H, dd); 6.1 (1H, d, J=3.4 Hz), 7.25–7.3 (2H, m); 7.47–7.52 (2H, m). |
| 11. | CH₃ | H | H | 4-fluorophenyl (F-) | 2 | 219 | 32 | 2.3 (3H, s); 3.6 (2H, t, J=6.0 Hz); 4.05 (2H, t, J=6.0 Hz); 5.9 (1H, d, J=2.8); 6.0 (1H, d, J=3.3 Hz); 7.04–7.1 (2H, m); 7.26–7.37 (2H, m). |

TABLE 1-continued (structure 1e): pyrrole ring with R¹, R², R³, R⁴ substituents and N-(CH₂)ₙ-OH group

| Comp. No. | R¹ | R² | R³ | R⁴ | n = | Mol. Wt. (mp °C.) | Yield (% w/w) | ¹H NMR (300 MHz, δ, CDCl₃) |
|---|---|---|---|---|---|---|---|---|
| 12. | CH₃ | H | H | 4-Cl-C₆H₄ | 2 | 235.5 | 61 | 2.3 (3H, s); 3.6 (2H, t, J=5.9 Hz); 4.12 (2H, t, J=5.9 Hz); 5.97 (1H, d, J=3.2 Hz); 6.10 (1H, d, J=3.2 Hz); 7.09–7.37 (4H, m). |
| 13. | CH₃ | H | C₆H₅ | C₆H₅ | 2 | 277 | 90 | 2.37 (3H, s); 3.5 (2H, t, J=6 Hz); 3.95 (2H, t, J=6.0 Hz); 6.2 (1H, d, J=2.8); 7.1–7.4 (10H, m). |
| 14. | i-Pr | H | H | CH₃ | 2 | 167 | 68 | 1.2 (6H, d, J=8 Hz); 2.2 (3H, s); 2.94 (1H, septet); 3.77 (2H, t, J=6.9 Hz); 3.97 (2H, t, J=6.9 Hz) |
| 15. | i-Pr | H | H | i-Pr | 2 | 195 | 93 | 1.21–1.24(12H, d, J=6.7 Hz); 2.91–2.98 (2H, m); 3.77 (1H, t, J=6.2 Hz); 4.01 (2H, t, J=6.2 Hz); 5.8 (2H, s). |
| 16. | i-Pr | H | H | C₆H₅ | 2 | 229 | 86 | 1.29 (6H, d, J=6.78 Hz); 3.0–3.05 (1H, m); 3.51 (2H, t, J=6.21 Hz); 4.12 (2H, t, J=6.25 Hz); 6.0 (1H, d, J=3.54 Hz); 6.125 (1H, d, J=3.54 Hz); 7.27–7.31 (3H, m) 7.37 (2H, m) |
| 17. | i-Pr | C₆H₅ | H | i-Pr | 2 | 271 | 42 | 1.25 (12H, d, J=6.5 Hz); 2.97 (1H, sep, J=6.7 Hz); 3.24 (1H, sep, J=6.7 Hz); 3.85 (2H, m); 4.1 (2H, t, J=7 Hz); 5.87 (1H, s); 7.19–7.32 (5H, m) |
| 18. | i-Pr | H | H | 4-CH₃O-C₆H₄ | 2 | 259 | 84 | 1.27 (6H, d, J=6.5 Hz); 2.99–3.04 (1H, m); 3.53 (2H, t, J=6.15 Hz); 3.82 (3H, s); 4.09 (2H, J=6.2 Hz); 5.96 (1H, d, J=3.5 Hz); 6.67 (1H, d, J=3.48 Hz); 6.91 (2H, d, J=8.9 Hz); 7.29 (2H, d, J=8.6 Hz) |
| 19. | i-Pr | H | H | 4-F-C₆H₄ | 2 | 247 | 22 | 1.27 (6H, d, J=6.0 Hz); 2.97–3.06 (1H, m); 3.53 (2H, t, J=6.0 Hz); 4.08 (2H, t, J=6.0 Hz); 5.99 (1H, d, J=3.60 Hz); 6.10 (1H, d, J=3.3 Hz); 7.05–7.1 (2H, t, J=8.8 Hz); 7.34–7.37 (2H, m) |

TABLE 1-continued

Structure (1e): pyrrole ring with substituents R¹, R², R³, R⁴ and N-(CH₂)ₙ-OH

| Comp. No. | R¹ | R² | R³ | R⁴ | n = | Mol. Wt. (mp °C.) | Yield (% w/w) | ¹H NMR (300 MHz, δ, CDCl₃) |
|---|---|---|---|---|---|---|---|---|
| 20. | i-Pr | H | phenyl | 4-F-phenyl | 2 | 323.2 (109° C.) | 55 | 1.34 (6H, d, J=7 Hz); 3.09 (1H, sep, J=7 Hz); 3.57 (2H, t, J=4.5 Hz); 4.02 (2H, t, J=4.5 Hz); 7.03–7.30 (9H, m) |
| 21. | i-Pr | phenyl-NHCO | H | 4-F-phenyl | 2 | 366 | 45 | 1.43–1.45 (6H, d, J=7.2 Hz); 3.3–3.4 (1H, m); 4.09–4.1 (2H, m); 3.80–3.85 (2H, m); 6.85 (1H, s); 7.0–7.5 (9H, m). |
| 22. | i-Pr | phenyl-NHCO | phenyl | 4-F-phenyl | 2 | 442 (175–178° C.) | 52 | 1.47 (6H, d, J=7.2 Hz); 3.5–3.6 (1H, m); 3.59 (2H, t, J=6.2 Hz); 3.99 (2H, t, J=6.6 Hz); 6.79 (1H, s); 6.91–7.0 (3H, m); 7.08–7.19 (10H, m). |
| 23. | i-Pr | phenyl-NHCO | phenyl | 4-F-phenyl | 3 | 456 (58–62° C.) | 50 | — |
| 24. | phenyl | —H | H | 4-F-phenyl | 2 | 281 | 79 | 1.55 (1H, s), 3.3 (2H, dd, J=6.0 Hz); 4.2 (2H, t, J=6.0 Hz); 6.25 (2H, dd, J=3.6 Hz); 7.1 (2H, t, J=7.0 Hz); 7.4 (1H, m, J=9.0 Hz); 7.42–7.47 (6H, m) |
| 25. | phenyl | —COOEt | H | 4-F-phenyl | 2 | 353 | 55 | 1.10 (3H, t, J=7.0 Hz); 1.60 (1H, s); 3.35 (2H, t, J=6.0 Hz); 4.00 (2H, J=6.0 Hz); 4.10 (2H, t, J=Hz); 6.69 (1H, s); 7.10 (2H, J=9.9 Hz); 7.39–7.46 (7H, m) |

Preparation 2

Alternatively, compound no. 22 as described in the table 1, can be prepared by using the corresponding aldehyde in better yields. The process is given below:

A mixture containing suitably substituted aldehyde (2 g) and sodium borohydride (0.167 g) was dissolved in absolute alcohol (20 mL). It was stirred at 0° C.–5° C. for about 2 hr. A solid product was obtained, which was diluted with ice-cold water (40 mL), stirred for 15 min, filtered and washed with DM water (2×10 mL). The compound was dried in a vacuum desiccator over phosphorous pentoxide (2 g, 100%).

Preparation 3

1-(2-hydroxyethyl)-2-ethyl-1H-pyrrole (Compound No. 26)

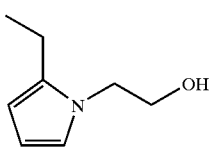

A mixture containing 2-bromoethyl-2-acetyl-1H-pyrrole (8.2 g), ethylene glycol (45 mL), 85% potassium hydroxide pellets (8.91 g) and 80% hydrazine hydrate (6.76 mL) was stirred at 200° C. for about 1.5 hr along with simultaneous distillation of volatile materials. The product obtained was extracted with ethyl acetate (2×100 mL). The ethyl acetate layer was washed with water (100 mL), dried over sodium sulfate, filtered and evaporated. The crude product obtained was purified by column chromatography (silica gel 100–200), using ethyl acetate:pet. ether (8:2) as an eluent to obtain 2.2 g of the title compound.

A mixture of 2-formylpyrrole (1 g), potassium hydroxide (2.3 g) and dry DMSO (20 mL) was stirred under nitrogen atmosphere. 1,2-dibromoethane (7.9 g) was added dropwise at 20–25° C. and stirred till the reaction is complete. Water (50 mL) was added and the reaction mixture was extracted with diethyl ether (3×50 mL). The combined organic layer was washed with water (30 mL), followed by brine (30 mL) and was dried over $Na_2SO_4$. The solvent was evaporated and the compound obtained was purified by column chromatography (silica gel 100-200) using ethyl acetate:hexane (2:8) as an eluent to obtain the title compound.

TABLE 2

| Comp. No. | Substituents on the pyrrole ring in (1e) | | | | | Mol. Wt. (mp° C.) | Yield (% w/w) | $^1$H NMR (300 MHz, δ, $CDCl_3$) |
|---|---|---|---|---|---|---|---|---|
| | $R^1$ | $R^2$ | $R^3$ | $R^4$ | N = | | | |
| 26. | $C_2H_5$ | H | H | H | 2 | 139 | 42 | 1.26 (3H, t, J=6.0 Hz); 2.59 (2H, q, $J_1$=7.62 Hz, $J_2$=7.44 Hz); 3.84 (2H, t, J=5.4 Hz); 3.98 (2H, t, J=5.35 Hz); 5.92–5.93 (1H, m); 6.11 (1H, t, J=3.12 Hz); 6.65 (1H, t, J=2.22 Hz). |

Preparation 4

1-(2-Bromoethyl)-1H-pyrrole-2-carbaldehyde (Compound No. 27)

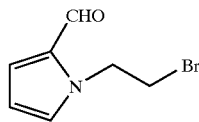

(Compound No. 27)

In like manner to that described in Preparation 4, following compounds of the formula (1c) (Given in Table 3) were prepared from the appropriately substituted pyrrole derivatives. The latter can be synthesized by using various routes found in literature.

TABLE 3

(1c)

| Comp. No. | Substituents on the pyrrole ring in (1c) | | | | | Mol. Wt. (mp ° C.) | Yield (% w/w) | $^1$H NMR (300 MHz, δ, $CDCl_3$) |
|---|---|---|---|---|---|---|---|---|
| | $R^1$ | $R^2$ | $R^3$ | $R^4$ | n = | | | |
| 27. | CHO | H | H | H | 2 | 202 | 47 | 3.65 (2H, t, J=6 Hz); 4.65 (2H, t, J=6 Hz); 6.33 (1H, m); 6.95–7.05 (2H, m); 9.5 (1H, m). |
| 28. | $COCH_3$ | H | H | H | 2 | 216 | 32 | 2.44 (3H, s); 3.67 (2H, t, J=6 Hz); 4.65 (2H, t, J=6 Hz); 6.16–6.18 (1H, m); 6.94 (1H, t, J=6 Hz); 7.01–7.03 (1H, m). |

Preparation 5

Preparation of 1-(2-hydroxyethyl)-1H-pyrrole (Compound No. 29)

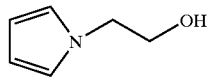
(Compound No. 29)

To a mixture of potassium hydroxide (16.7 g) and dry DMSO (150 mL), pyrrole (5 g) was added dropwise at 20–25° C., with stirring under nitrogen atmosphere. Stirring was continued for 1 hr at 20–25° C. Ethyl bromoacetate (24.5 g) was added dropwise at 20–25° C. and stirring was continued for 2 hr. In the reaction mixture (150 mL) DM water was added and pH was made acidic (pH=3) with 20% HCl (50 mL). The reaction mixture was extracted with diethyl ether (2×100 mL). The combined organic extract was washed with DM water (100 mL), saturated brine (100 mL) and dried over $Na_2SO_4$. The solvent was evaporated to obtain pyrrol-1-yl-acetic acid.

To a suspension of sodium borohydride (3.6 g) in tetrahydrofuran (70 mL), pyrrol-1-yl-acetic acid (6 g) dissolved in THF (70 mL) was added dropwise at 20° C.–25° C. within 10–15 min under nitrogen atmosphere. When the evolution of hydrogen gas ceases, the reaction mixture was cooled to 5–10° C. and iodine (5.9 g) dissolved in THF was added dropwise at 5° C.–10° C. and was stirred further for 2 hrs at 20° C.–25° C. The reaction mixture poured in mixture of ice-cold KOH solution (10 mL) and DM water (50 mL). The solution was with ethyl acetate (2×50 mL). The organic extract was washed with water (30 mL), brine (30 mL) and dried over $Na_2SO_4$. The solvent was evaporated under reduced pressure, to obtain the title compound.

In like manner to that described in Preparation 5, following compounds of the formula (1e) (Given in Table 4) were prepared from the appropriately substituted pyrrole. The latter can be synthesized by using various routes found in literature.

TABLE 4

(1e)

| Comp. No. | Substituents on the pyrrole ring in (1c) | | | | | Mol. Wt. (mp ° C.) | Yield (% w/w) | $^1$H NMR (300 MHz, δ, $CDCl_3$) |
|---|---|---|---|---|---|---|---|---|
| | $R^1$ | $R^2$ | $R^3$ | $R^4$ | n = | | | |
| 29. | H | H | H | H | 2 | 111 | 98 | — |
| 30. | $CH_3$ | H | $CH_3$ | H | 2 | 139 | 40.4 | 2.02 (3H, s); 2.19 (3H, s); 3.7–3.9 (4H, m); 5.73 (1H, s); 6.38 (1H, s). |
| 31. | Ph-CH₃ (phenyl) | H | $CH_3$ | H | 2 | 201 | 13 | 2.05 (3H, s); 3.75 (2H, t, J=6 Hz); 4.03 (2H, t, J=5.5 Hz); 6.07 (1H, s); 6.62 (1H, s); 7.27–7.42 (5H, m). |
| 32. | $CH_3$ | H | phenyl | H | 2 | 201 | 57 | 2.24 (3H, s); 3.82–4.01 (4H, m); 6.19 (1H, s); 6.9 (1H, s); 7.1–7.4 (5H, m). |
| 33. | $SCH_3$ | H | H | H | 2 | 157 | 90 | 2.2 (3H, s); 3.85 (2H, t, J=6.0 Hz); 4.1 (2H, t, J=5.5 Hz); 6.14 (1H, dd); 6.38 (1H, dd); 6.85 (1H, dd) |

Preparation 6

Preparation of Methyl 2-(2,5-dimethyl-1H-pyrrol-1-yl)ethane sulfonate (Compound No. 35)

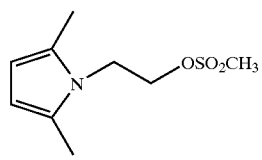

To a solution of compound 1 (3.0 g in 20 mL dichloromethane) obtained in preparation 1, triethylamine (11 mL) was added followed by addition of methanesulfonyl chloride (5 g) at 0° C. The reaction mixture was stirred at 0° C. for 1 h under nitrogen atmosphere. The mixture was warmed to temperature of about 20 to 25° C. and was stirred at that temperature for about 2 h (TLC). After the completion of the reaction, water (30 mL) was added and the organic layer was separated. The mixture was washed with saturated sodium bicarbonate solution (20 mL), water (20 mL) and then with brine (20 mL) and dried over $Na_2SO_4$. The organic layer was concentrated under reduced pressure. The crude substance was used in the next step without purification.

In like manner to that described in Preparation 6 following compounds of the formula (1c) (given in Table 5) were prepared from the appropriately substituted pyrrole derivatives (1e) described earlier.

TABLE 5

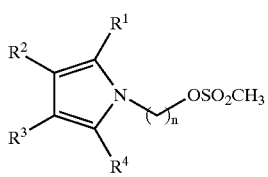

(1c)

| Comp. No. | \multicolumn{4}{c|}{Substituents on the pyrrole ring in (1c)} | n = | Mol. Wt. (mp ° C.) | Yield (% w/w) | $^1$H NMR (300 MHz, δ, $CDCl_3$) |
|---|---|---|---|---|---|---|---|---|
| | $R^1$ | $R^2$ | $R^3$ | $R^4$ | | | | |
| 34. | H | H | H | H | 2 | 189 | 26 | 2.7(3H, s); 4.43 (2H, t, J=5.2 Hz); 6.17 (2H, t, J=2.1 Hz); 6.7 (2H, t, J=2.1 Hz); |
| 35. | $CH_3$ | H | H | $CH_3$ | 2 | 217 | 64 | 2.23 (6H, s); 2.68 (3H, s); 4.08 (2H, t, J=5.8 Hz); 4.34 (2H, t, J=5.8 Hz); 5.78 (2H, s) |
| 36. | $CH_3$ | H | $CH_3$ | H | 2 | 217 | 98 | — |
| 37. | $C_2H_5$ | H | H | H | 2 | 217 | 90 | 1.29 (3H, t, J=2.64 Hz); 2.58 (2H, q, J=7.32 Hz); 2.71 (3H, s); 4.15 (2H, t, J=5.52 Hz); 4.41 (2H, t, J=5.5 Hz); 5.92 (1H, m); 6.11 (1H, t, J=3.16 Hz); 6.63 (1H, t, J=2.26 Hz). |
| 38. | $CH_3$ | H | H | $CH_2CH_3$ | 2 | 231 | 56 | 1.26 (3H, t, J=7.4 Hz); 2.25 (3H, m) 2.57 (2H, q, J=7.42 Hz); 2.69 (3H, s); 4.12 (2H, t, J=5.9 Hz); 4.34 (2H, t, J=5.9 Hz); 5.8–5.83 (2H, m). |
| 39. | $CH_3$ | H | H | $(CH_2)_2CH_3$ | 2 | 246 | 45 | 1.02 (3H, t, J=7 Hz); 1.65 (2H, m); 2.25 (3H, s); 2.5 (2H, t, J=7.7 Hz); 2.69 (3H, s); 4.1 (2H, t, J=5.9 Hz); 4.35 (2H, t, J=5.9 Hz); 5.8–5.83 (2H, m). |
| 40. | $CH_3$ | H | H | $(CH_2)_3CH_3$ | 2 | 259 | 72 | 0.95 (3H, t, J=7.2 Hz); 1.44–1.46 (2H, m); 1.58–1.62 (2H, m); 2.25 (3H, s); 2.5 (2H, t, J=5.9 Hz); 2.7 (3H, s); 4.1 (2H, t, J=5.9 Hz); 4.39 (2H, t, J=5.9 Hz); 5.8 (2H, s). |
| 41. | $CH_3$ | H | H | C₆H₄CH₃ (p-tolyl) | 2 | 279 | 98 | 2.34 (3H, s); 2.83 (3H, s); 4.11 (2H, t, J=5.7 Hz); 4.27 (2H, t, J=5.7 Hz); 5.96 (1H, J=3.4 Hz); 6.10 (1H, d, J=3.4 Hz); 7.27–7.43 (5H, m). |

TABLE 5-continued

Structure (1c): pyrrole with R¹, R², R³, R⁴ substituents and N-(CH₂)ₙ-OSO₂CH₃

| Comp. No. | R¹ | R² | R³ | R⁴ | n = | Mol. Wt. (mp °C.) | Yield (% w/w) | ¹H NMR (300 MHz, δ, CDCl₃) |
|---|---|---|---|---|---|---|---|---|
| 42. | CH₃ | H | H | phenyl | 2 | 279 | 86 | 2.28 (3H, s); 2.73 (3H, m); 4.16 (2H, d, J=5.4 Hz); 4.4 (2H, d, J=5.4 Hz); 6.2 (1H, s); 6.9 (1H, s); 7.17 (1H, d, J=6.75 Hz); 7.3 (2H, d, J=7.0 Hz); 7.46 (2H, d, J=7.0 Hz). |
| 43. | CH₃ | H | H | 4-methylphenyl (H₃C-C₆H₄-) | 2 | 293 | 68 | 2.33 (3H, s); 2.38 (3H, s); 2.65 (3H, s); 4.12 (2H, t, J=6.3 Hz); 4.25 (2H, t, J=6.3 Hz); 5.95 (1H, d, J=3.4 Hz); 6.10 (1H, d, J=3.4 Hz); 7.19–7.25 (4H, m). |
| 44. | CH₃ | H | H | 3-methylphenyl | 2 | 293 | 95 | 2.33 (3H, s); 2.38 (3H, s); 2.66 (3H, s); 4.12 (2H, t, J=5.8 Hz); 4.27 (2H, t, J=5.7 Hz); 5.95 (1H, d, J=3.37 Hz); 6.09 (1H, d, J=3.42 Hz); 7.12–7.16 (2H, m); 7.25–7.31 (2H, m). |
| 45. | CH₃ | H | H | 2-methylphenyl | 2 | 293 | 55 | 2.34 (3H, s); 2.38 (3H, s); 2.67 (3H, s); 4.13 (2H, t, J=5.8 Hz); 4.27 (2H, t, J=5.7 Hz); 5.96 (1H, d, J=3.36 Hz); 6.1 (1H, d, J=3.39 Hz); 7.13–7.29 (4H, m) |
| 46. | CH₃ | H | H | 4-methoxyphenyl (H₃CO-C₆H₄-) | 2 | 309 | 62 | 2.3 (3H, s); 2.67 (3H, s), 3.8 (3H, s); 4.12 (2H, t, J=5.45 Hz), 4.24 (2H, t, J=5.45 Hz), 5.9 (1H, d, J=3.39 Hz), 6.0 (1H, d, J=3.39 Hz), 6.95 (2H, d, J=6.78 Hz); 7.26 (2H, d, J=6.78 Hz). |
| 47. | CH₃ | H | H | 4-bromophenyl | 2 | 358 | 70 | 2.33 (3H, s); 2.7 (3H, s); 4.13–4.15 (2H, m); 4.2–4.25 (2H, m); 5.97 (1H, d, J=3.4 Hz); 6.12 (1H, d, J=3.4 Hz); 7.21–7.26 (2H, m); 7.52–7.55 (2H, m). |
| 48. | CH₃ | H | H | 4-fluorophenyl | 2 | 297 | 90 | 2.3 (3H, s); 2.7 (3H, s); 3.6 (2H, t, J=6.0 Hz); 4.1 (2H, d, J=5.6 Hz); 4.22 (2H, d, J=5.4 Hz); 5.9 (1H, d, J=3.4 Hz); 6.0 (1H, d, J=3.4 Hz); 7.04–7.1 (2H, m); 7.2–7.3 (2H, m). |

TABLE 5-continued

![Structure 1c: pyrrole with R1, R2, R3, R4 substituents and N-(CH2)n-OSO2CH3]

(1c)

| Comp. No. | \multicolumn{4}{c}{Substituents on the pyrrole ring in (1c)} | n = | Mol. Wt. (mp ° C.) | Yield (% w/w) | $^1$H NMR (300 MHz, δ, CDCl$_3$) |
|---|---|---|---|---|---|---|---|---|
| | R$^1$ | R$^2$ | R$^3$ | R$^4$ | | | | |
| 49. | CH$_3$ | H | H | 4-Cl-C$_6$H$_4$ | 2 | 313.5 | 82 | 2.3 (3H, s); 2.69 (3H, s); 4.15 (2H, d, J=6.3 Hz); 4.25 (2H, d, J=6.3 Hz); 5.96–5.97 (1H, dd); 6.1 (1H, d, J=3.4 Hz); 7.27–7.4 (4H, m). |
| 50. | C$_6$H$_5$ | H | CH$_3$ | H | 2 | 279 | 90 | 2.13 (3H, s); 2.73 (3H, m); 4.2–4.28 (4H, m); 6.05 (1H, s); 6.59 (1H, s); 7.29–7.43 (5H, m). |
| 51. | CH$_3$ | H | C$_6$H$_5$ | C$_6$H$_5$ | 2 | 355 | 90 | 2.73 (3H, s); 4.09–4.14 (4H, m); 6.2 (1H, s); 7.0–7.4 (10H, m). |
| 52. | i-Pr | H | H | CH$_3$ | 2 | 245 | 97.1 | 1.28 (6h, d, J=7.7 Hz); 2.25 (3H, s); 2.83–2.92 (1H, m); 4.14 (2H, t, J=6.9 Hz); 4.34 (2H, t, J=6.9 Hz); 5.83 (2H, s). |
| 53. | i-Pr | H | H | i-Pr | 2 | 272 | 37 | 1.23–1.25(12H, d, J=6.7 Hz); 2.76 (3H, s); 2.82–2.99 (2H, m); 4.18 (2H, m); 4.33 (2H, m); 5.86 (2H, s) |
| 54. | i-Pr | H | H | C$_6$H$_5$ | 2 | 307 | 100 | 1.30 (6H, t, J=6.78 Hz), 2.65 (3H, m); 2.96–3.00 (1H, m); 4.04 (2H, t, J=6 Hz); 4.32 (2H, t, J=6 Hz); 6.0 (1H, d, J=3.54 Hz); 6.12 (1H, d, J=3.54 Hz); 7.32–7.43 (5H, m). |
| 55. | i-Pr | C$_6$H$_5$ | H | i-Pr | 2 | 349 | 97 | — |
| 56. | i-Pr | H | H | 4-CH$_3$O-C$_6$H$_4$ | 2 | 337 | 99 | — |

TABLE 5-continued structure (1c): pyrrole ring with R¹, R², R³, R⁴ substituents and N-(CH₂)ₙ-OSO₂CH₃ group

| Comp. No. | R¹ | R² | R³ | R⁴ | n = | Mol. Wt. (mp °C.) | Yield (% w/w) | ¹H NMR (300 MHz, δ, CDCl₃) |
|---|---|---|---|---|---|---|---|---|
| 57. | i-Pr | H | H | 4-F-C₆H₄ | 2 | 325 | 72 | 1.29 (6H, d, J=6.0 Hz); 2.69 (3H, s); 2.92–2.99 (1H, m); 4.05 (2H, t, J=6.0 Hz) 4.27 (2H, t, J=6.0 Hz); 6.00 (1H, d, J=3.4 Hz); 6.1 (1H, d, J=3.4 Hz); 7.07–7.1 (2H, t, J=6.0 Hz); 7.30–7.35 (2H, m) |
| 58. | i-Pr | H | C₆H₅ | 4-F-C₆H₄ | 2 | 369 | 61 | 1.35 (6H, d, J=7 Hz); 2.76 (3H, s); 3.0–3.05 (1H, m); 4.05 (2H, t, J=6.2 Hz); 4.15 (2H, t, J=6 Hz); 6.22 (1H, s); 7.07–7.30 (9H, m) |
| 59. | i-Pr | C₆H₅-NHCO | H | 4-F-C₆H₄ | 2 | 444 | 15 | 1.5–1.52 (6H, d, J=7.1 Hz); 2.84 (3H, s); 3.44–3.52 (1H, m); 4.12–4.15 (2H, t, J=6.4 Hz); 4.3–4.34 (2H, t, J=6.4 Hz); 6.32 (1H, s); 7.12–7.18 (3H, t, J=8.5 Hz); 7.3–7.4 (4H, m); 7.56–7.59 (2H, d, J=7.6 Hz). |
| 60. | i-Pr | C₆H₅-NHCO | C₆H₅ | 4-F-C₆H₄ | 2 | 520 (160–162) | 85 | — |
| 61. | i-Pr | C₆H₅-NHCO | C₆H₅ | 4-F-C₆H₄ | 3 | 534 | 100 | — |
| 62. | C₆H₅ | H | H | 4-F-C₆H₄ | 2 | 359 | 98 | — |
| 63. | C₆H₅ | –COOEt | H | 4-F-C₆H₄ | 2 | 431 | 98.3 | — |
| 64. | SCH₃ | H | H | H | 2 | 235 | 95 | 2.29 (3H, s); 2.77 (3H, s); 4.35–4.48 (4H, m); 6.17 (1H, dd); 6.4 (1H, dd); 6.85 (1H, dd). |

Preparation 7

4-[2-(5-Methyl-2-phenylpyrrol-1-yl)ethoxy] benzaldehyde (Compound No. 65)

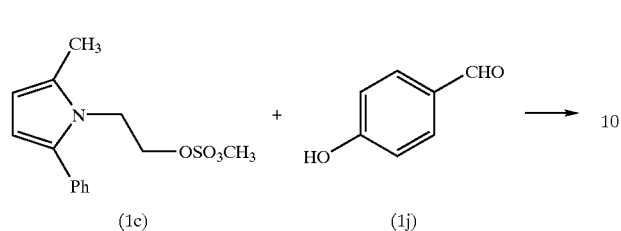

(1c)    (1j)

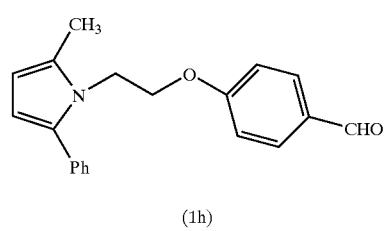

(1h)

To a suspension of potassium carbonate (16.43 g) in dimethyl formamide (50 mL), 4-hydroxy benzaldehyde (4.37 g) was added and warmed to 90° C. to 95° C. To the solution, methyl 1-[5-methyl-2-phenyl-1H-pyrrol-1yl] ethane sulfonate (10 g) (compound no. 41) dissolved in dimethyl formamide (50 mL) was added within 30 min and the reaction was continued for further 4 hours. The reaction mixture was diluted with water (100 mL) and was extracted with ethyl acetate (3×100 mL), washed with water (3×100 mL), brine (200 mL), and was dried over sodium sulfate. The solvent was evaporated under reduced pressure, to yield the title compound.

Preparation 8

(S)-Ethyl 3-{4-[2-(2,5-dimethylpyrrol-1-yl)ethoxy] phenyl}-2-ethoxypropanoate (Example 2)

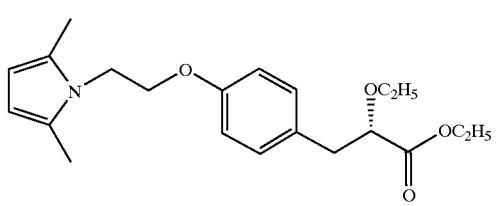

(I)

A mixture (S)-ethyl 3-(4-hydroxyphenyl)-2-ethoxypropanoate (1.12 g), and potassium carbonate (2.37 g) in dimethyl formamide (20 mL) was stirred at 70° C.–80° C. for 10 min. The respective mesylate (Compound. No. 35) (2.3 g) dissolved in dimethyl formamide (10 mL) was added and stirred at 70° C. to 80° C. for 24 h and was allowed to stand overnight at 70° C.–80° C. (ca.16 h). The reaction mixture was diluted with water (40 mL). The product was extracted with ethyl acetate (2×50 mL), washed with water (2×40 mL), brine (50 mL) and was dried over sodium sulfate. Ethyl acetate was evaporated under reduced pressure to obtain an oily product. The crude (3 g) product was chromatographed over silica gel using ethyl acetate:petroleum ether (60-80) (1:9) as an eluent to afford the pure titled compound (2.6 g, 57%).

Preparation 9

(S)-Ethyl 3-{4-[2-(2-formylpyrrol-1-yl)ethoxy] phenyl}-2-ethoxypropanoate (Example 5)

A mixture of (S)-ethyl 3-(4-hydroxyphenyl)-2-ethoxypropionate (1.12 g) and dry potassium carbonate (2.37 g) in dimethyl formamide (20 mL) was stirred at 80° C. for 30 min. 1-(2-bromoethyl)2-carbaldehyde pyrrole (1.0 g, Compound. No. 27) was added at 40° C. and stirring was continued at 80° C. for 24 h. The reaction mixture was cooled to 20° C.–25° C. and 20 mL water was added. The

TABLE 6

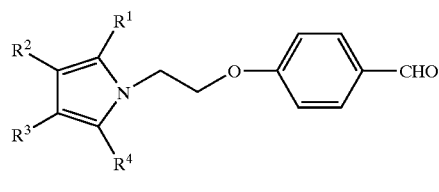

(1h)

| Comp. No. | Substituents on the pyrrole ring in (1c) | | | | Mol. Wt. (mp ° C.) | Yield (% w/w) | ¹H NMR (300 MHz, δ, CDCl₃) |
|---|---|---|---|---|---|---|---|
| | R¹ | R² | R³ | R⁴ | | | |
| 65. | CH₃ | H | H | Phenyl | 306 | 99 | 2.39 (3H, s); 4.0 (2H,t, J=6.3 Hz); 4.35 (2H, t, J=6.3 Hz); 5.98 (1H, d, J=3.4 Hz); 6.12 (1H, t, J=3.4 Hz); 6.74 (2H, d, J=8.7); 7.38–7.42 (5H, m); 7.73–7.75 (2H, d, J=8.8 Hz); 9.85 (1H, s). | reaction mixture was extracted with ethyl acetate (2×25 mL), washed with water (2×20 mL), brine (25 mL) and was dried over sodium sulfate. The organic layer was evaporated under reduced pressure to obtain an oily product. The crude oily product was chromatographed over silica gel (100–200 mesh) using ethyl acetate:petroleum ether (1:9) as an eluent to afford the title compound as a yellow oil (0.4 g, 22%).

Preparation 10

(S)-Ethyl 3-{4-[2-(5-methyl-2-(2-methylphenyl)pyrrol-1-yl)ethoxy]phenyl}-2-ethoxypropanoate (Example 2)

A mixture of (S)-ethyl 3-(4-hydroxyphenyl)-2-ethoxypropionate (1.09 g), and dry potassium carbonate (2.37 g) in toluene (15 mL) was heated to reflux for 45 min with continuous removal of water using a Dean-Stark water separation. The mixture was cooled to 50° C. and mesylate compound No. 8 (1.2 g) was added. The reaction mixture was continued to reflux for 24 hrs. Later it was cooled to 20-C-25° C. and toluene was distilled at reduced pressure. To the residue, DM water (20 mL) was added and the crude product was extracted with ethyl acetate (2×25 mL), washed with water (2×20 mL), brine (25 mL) and was dried over sodium sulfate. The solvent was evaporated under reduced pressure to obtain an oily product. The crude oily product was chromatographed over silica gel using ethyl acetate:petroleum ether (60-80) (1:9) as an eluent to afford the title product as a yellow oil (63%).

In like manner to that described in preparation 8-10, the following compounds of the formula (I) (given in Table 7) were prepared from appropriately substituted pyrrole derivatives described in either Table 5 or obtained from other methods described herein.

TABLE 7

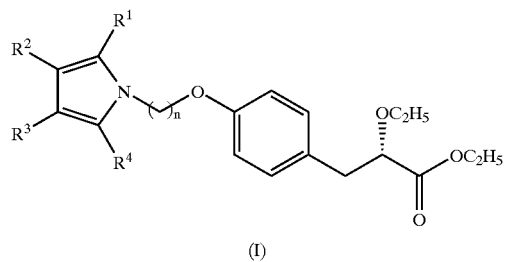

(I)

| Comp. No. | $R^1$ | $R^2$ | $R^3$ | $R^4$ | n = | Mol. Wt. (mp ° C.) | Yield (% w/w) | $^1$H NMR (300 MHz, δ, CDCl$_3$) |
|---|---|---|---|---|---|---|---|---|
| 1 | H | H | H | H | 2 | 331 | 37 | 1.15 (3H, t, J=6.9 Hz); 1.22 (3H, t, J=6.9 Hz); 2.94 (2H, dd); 3.33–3.38 (1H, m); 3.54–3.65 (1H, m); 3.95 (1H, dd); 4,12–4.26 (6H, m); 6.16 (2H, t, J=2.1 Hz); 6.7 (2H, t, J=2.1 Hz); 6.8 (2H, d, J=8.5 Hz); 7.15 (2H, d, J=8.5 Hz) |
| 2. | CH$_3$ | H | H | CH$_3$ | 2 | 359 | 57 | 1.15 (3H, t, J=6.9 Hz), 1.25 (3H, t, J=6.9 Hz), 2.27 (6H, s); 2.91–2.94 (2H, m); 3.32–3.60 (2H, m); 3.97–4.2 (7H, m); 5.78 (2H, s); 6.78(2H, d, J=8.5 Hz); 7.15 (2H, d, J=8.5 Hz). |
| 3. | CH$_3$ | H | CH$_3$ | H | 2 | 359 | 18 | 1.15 (3H, t, J=7 Hz); 1.26 (3H, t, J=7 Hz); 2.04 (3H, s); 2.23 (3H, s); 2.91–2.94 (2H, m); 3.3–3.39 (1H, m); 3.5–3.62 (1H, m); 3.92 (1H, dd, J=6.0 Hz); 4.12–4.2 (6H, m); 5.7 (1H, s); 6.4 (1H, s); 6.77 (2H, d, J=8.6 Hz); 7.15 (2H, d, J=8.6 Hz). |
| 4. | C$_2$H$_5$ | H | H | H | 2 | 359 | 18 | 1.15 (3H, t, J=7.02 Hz); 1.22 (3H, t, J=5.74 Hz); 1.26 (3H, t, J=6.03 Hz); 2.62 (2H, q); 2.93 (2H, d, J=5.7 Hz); 3.94 (2H, t, J=?? Hz); 4.12–4.20 (5H, m); |

TABLE 7-continued

Structure (I): Pyrrole ring with substituents R¹ (position 2), R² (position 3), R³ (position 4), R⁴ (position 5), N-linked via $(CH_2)_n$ to O-phenyl-$CH_2$-CH($OC_2H_5$)-C(=O)-$OC_2H_5$.

| Comp. No. | R¹ | R² | R³ | R⁴ | n = | Mol. Wt. (mp °C.) | Yield (% w/w) | ¹H NMR (300 MHz, δ, CDCl₃) |
|---|---|---|---|---|---|---|---|---|
| 5. | CHO | H | H | H | 2 | 359 | 22 | 5.91 (1H, m); 6.10 (1H, t, J=3.12 Hz); 6.69–6.75 (1H, m); 6.76 (2H, d, J=6.7 Hz); 7.13 (2H, d, J=8.61 Hz). 1.1 (3H, t, J=6.9 Hz); 1.26 (3H, t, 6.9 Hz); 2.94–4.08 (5H, m); 4.22 (2H, t, J=4.9 Hz); 4.7 (2H, 4.9 Hz); 6.23 (1H, dd); 6.7 (2H, dd, J=8.5 Hz); 6.97 (1H, dd); 7,1 (1H, dd); 9.5 (1H, s). |
| 6. | COCH₃ | H | H | H | 2 | 137 | 10 | 1.15 (3H, t, J=3.48 Hz); 1.2 (3H, J=5.1 Hz); 2.44 (3H, s); 2.93 (2H, dd, J=5.55 Hz); 3.0–3.35 (2H, m); 3.94 (2H, J=3.58 Hz), 4.16 (2H, q, J₁ = 1.44 Hz, J₂ = 1.41 Hz); 4.21 (1H, t, J=5.04 Hz); 4.69 (2H, t, J=4.99 Hz); 6.14–6.15 (1H, m); 6.75 (2H, d, J=8.37 Hz); 6.99–7.01 (2H, m) 7.11 (2H, d, J=8.64 Hz). |
| 7. | CH₃ | H | H | CH₂CH₃ | 2 | 373 | 45 | 1.15 (3H, t, J=7 Hz); 1.22 (3H, t, J=7 Hz); 1.27 (3H, t, J=7 Hz); 2.28 (3H, m); 2.63 (2H, q, J=7.4 Hz); 2.9–2.96 (2H, m); 3.3–3.6 (2H, m); 3.92–4.19 (7H, m), 5.8–5.83 (2H, m); 6.75 (2H, d, J=6.78 Hz); 7.14 (2H, d, J=6.78 Hz). |
| 8. | CH₃ | H | H | (CH₂)₂CH₃ | 2 | 389 | 41 | 1.02(3H, t, J=6.9 Hz); 1.15 (3H, t, J=6.9 Hz); 1.23 (3H, t, J=7.14 Hz), 1.65–1.7 (2H, m); 2.28 (3H, s); 2.5 (2H, t, J=7.75 Hz); 2.9–2.92 (2H, m); 3.25–3.5 (2H, m); 3.94 (1H, t, J=3.66 Hz); 4.0–4.2 (6H, m) 5.8–5.83 (2H, m); 6.75 (2H, d, J=8.5 Hz); 7.15 (2H, d, J=8.5 Hz). |
| 9. | CH₃ | H | H | (CH₂)₃CH₃ | 2 | 401 | 46 | 0.95 (3H, t, J=7.2 Hz); 1.15 (3H, t, J=7 Hz); 1.23 (3H, t, J=7 Hz); 1.4–1.47 (2H, m); 1.6–1.7 (2H, m); 2.28 (3H, s); 2.5 (2H, t, J=7.71 Hz); |

TABLE 7-continued

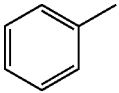

(I)

| Comp. No. | Substituents on the pyrrole ring in (I) | | | | n = | Mol. Wt. (mp °C.) | Yield (% w/w) | $^1$H NMR (300 MHz, δ, CDCl$_3$) |
|---|---|---|---|---|---|---|---|---|
| | R$^1$ | R$^2$ | R$^3$ | R$^4$ | | | | |
| | | | | | | | | 2.9–2.97 (2H, m); 3.3–3.39 (1H, m); 3.55–3.63 (1H, m); 4.04–4.22 (6H, m); 5.8–5.83 (2H, m); 6.7 (2H, d, J=8.5 Hz); 7.15 (2H, d, J=8.5 Hz). |
| 10. | CH$_3$ | H | H | 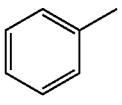 | 2 | 421 | 85 | 1.15 (3H, t, J=6.9 Hz); 1.22 (3H, t, J=7.1 Hz); 2.37 (3H, s); 2.9–2.92 (2H, dd); 3.32–3.35 (1H, m); 3.5–3.58 (1H, m); 3.9–3.92 (3H, m); 4.12–4.19 (2H, q); 4.28 (2H, t, J=6.5 Hz); 5.96–5.97 (1H, d, J =3.1 Hz); 6.1–6.11 (1H, d, J=3.11 Hz); 6.6 (2H, d, J = 8.5 Hz); 7.06–7.09 (2H, d, J=8.5 Hz); 7.3–7.4 (5H, m). |
| 11. | CH$_3$ | H | 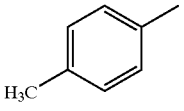 | H | 2 | 421 | 63 | 1.15 (3H, t, J=6.9 Hz); 1.22 (3H, t, J=7.1 Hz); 2.37 (6H, s); 2.9–2.92 (2H, m), 3.3–3.4 (1H, m); 3.53–3.62 (1H, m); 3.9 (3H, t, J=6.6 Hz); 4.1–4.22 (6H, m); 6.2 (1H, s); 6.8 (2H, d, J=8.5 Hz); 6.98 (1H, s); 7.15 (2H, d, J=8.5 Hz); 7.23–7.33 (3H, m) 7.4 (2H, t, J=7.1 Hz). |
| 12. | CH$_3$ | H | H | 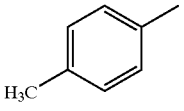 | 2 | 435 | 34 | 1.16 (3H, t, J=6.9 Hz); 1.22 (3H, t, J=6.9 Hz); 2.37 (3H, s); 2.39 (3H, s); 2.9–2.92 (2H, m); 3.3–3.37 (1H, m); 3.56–3.62 (1H, m); 3.91–4.2 (5H, m); 4.27 (2H, m); 5.95 (1H, d, J=3.36 Hz); 6.10 (1H, d, J=3.36 Hz); 6.6 (2H, d, J=8.5 Hz); 7.0 (2H, d, J=6.78 Hz); 7.19 (2H, d, J=8.5 Hz); 7.28 (2H, d, J=6.78 Hz). |

TABLE 7-continued

| Comp. No. | Substituents on the pyrrole ring in (I) | | | | n = | Mol. Wt. (mp °C.) | Yield (% w/w) | $^1$H NMR (300 MHz, δ, CDCl$_3$) |
|---|---|---|---|---|---|---|---|---|
| | R$^1$ | R$^2$ | R$^3$ | R$^4$ | | | | |
| 13. | CH$_3$ | H | H | 3,5-dimethylphenyl | 2 | 435 | 37 | 1.15 (3H, t, J=6.9 Hz), 1.22 (3H, t, J=7.13 Hz), 2.37 (6H, s); 2.91 (2H, d, J=5.94 Hz); 3.89–3.95 (5H, m); 4.15 (2H, q, J$_1$ = 7.11 Hz, J$_2$ = 7.11 Hz); 4.28 (2H, t, J=6.63 Hz); 5.95 (1H, d, J=3.39 Hz); 6.07 (1H, d, J=3.39 Hz); 6.59 (2H, d, J=7.62 Hz); 7.07 (2H, d, J=8.64 Hz); 7.15–7.28 (4H, m) |
| 14. | CH$_3$ | H | H | 2,3-dimethylphenyl | 2 | 435 | 53 | 1.15 (3H, t, J=6.9 Hz); 1.22 (3H, t, J=7.13 Hz); 2.37 (6H, s); 2.9–2.92 (2H, m); 3.3–3.58 (2H, m); 3.89–3.95 (3H, m); 4.15 (2H, t, J=6 Hz); 4.28 (2H, t, J=6 Hz); 5.95 (1H, d, J=3.2 Hz); 6.0 (1H, d, J=3.2 Hz); 6.6 (2H, d, J=7.62 Hz); 7.0 (2H, d, J=8.64 Hz); 7.12–7.28 (4H, m). |
| 15. | CH$_3$ | H | H | 4-methoxy-3-methylphenyl | 2 | 451 | 41 | 1.1 (3H, t, J=7 Hz); 1.22 (3H, t, J=7 Hz); 2.36 (3H, s); 2.9–2.92 (2H, dd); 3.3–3.32 (1H, m); 3.52–3.62 (1H, m); 3.84 (3H, m); 3.9–3.94 (3H, m); 4.14 (2H, t, J=6.68 Hz); 4.22(2H, t, J=6.68 Hz); 5.9 (1H, d, J=3.36 Hz); 6.0 (1H, d, J=3.36 Hz); 6.64 (2H, d, J=8.58 Hz); 6.95 (2H, d, J=6.78 Hz); 7.10 (2H, d, J=8.5 Hz); 7.31 (2H, d, J=6.78 Hz). |
| 16. | CH$_3$ | H | H | 4-bromo-3-methylphenyl | 2 | 500 | 40 | 1.16 (3H, t, J=7 Hz); 1.2 (3H, t, J=7 Hz); 2.37 (3H, s); 2.95 (2H, dd); 3.29–3.38 (1H, m); 3.55–3.63 (1H, m); 3.9–3.95 (3H, m); 4.17 (2H, t, J=6.3 Hz); 4.28 (2H, t, J=6.3 Hz); 5.9 (1H, d, J=3.42 Hz); 6.1 (1H, d, J=3.42 Hz); 6.6 (2H, d, J=8.5 Hz); 7.21 (2H, d, J=8.5 Hz); 7.29 (2H, d, J=8.5 Hz); 7.5 (2H, d, J=8.5 Hz). |

TABLE 7-continued
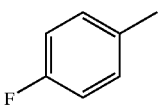
(I)
| Comp. No. | Substituents on the pyrrole ring in (I) | | | | n = | Mol. Wt. (mp ° C.) | Yield (% w/w) | ¹H NMR (300 MHz, δ, CDCl₃) |
|---|---|---|---|---|---|---|---|---|
| | R¹ | R² | R³ | R⁴ | | | | |
| 17. | CH₃ | H | H | 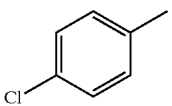 | 2 | 439 | 30 | 1.15 (3H, t, J=6.99 Hz); 1.23 (3H, t, J=6.99 Hz); 1.58 (3H, s); 2.9–2.93 (2H, dd); 3.55–3.65 (1H, m); 3.85–4.0 (3H, m); 4.1–4.2 (2H, m); 4.24 (2H, t, J=6.4 Hz) 5.9 (1H, d, J=3.3); 6.0 (1H, d, J=3.4 Hz); 6.6 (2H, t, J=8.6 Hz) 7.0–7.1 (4H, m); 7.26–7.38 (2H, m). |
| 18. | CH₃ | H | H | 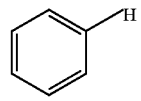 | 2 | 455.5 | 62 | 1.15 (3H, t, J=7 Hz); 1.23 (3H, t, J=7 Hz); 2.36 (3H, s); 2.9–2.95 (2H, dd); 3.33–3.4 (1H, m); 3.53–3.62 (1H, m); 3.9–4.13 (3H, m); 4.18 (2H, t, J=6.3 Hz); 4.26 (2H, t, J=6.3 Hz); 5.97 (1H, d, J=3.27 Hz); 6.1 (1H, d, J=3.4 Hz); 6.6 (2H, d, J=8.4 Hz); 7.1 (2H, d, J=8.4 Hz); 7.25–7.38 (2H, m). |
| 19. | 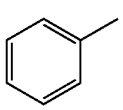 | H | CH₃ | H | 2 | 421 | 13 | 1.15 (3H, t, J=6.9 Hz); 1.23 (3H, t, J=7.2 Hz); 2.13 (3H, s); 2.92 (2H, d); 3.33 (1H, m); 3.59 (1H, m); 3.94 (3H, m); 4.07–4.26 (4H, m); 6.05 (1H, s); 6.67–6.72 (3H, m); 7.12 (2H, m); 7.3–7.43 (5H, m). |
| 20. | CH₃ | H | 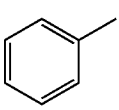 | | 2 | 497 | 32 | 1.153 (3H, t, J=7.0 Hz); 1.24 (3H, t, J=7 Hz); 2.4 (3H, s); 2.9–2.92 (2H, m); 3.33–3.36 (1H, m); 3.53–3.63 (1H, m); 3.85–3.95 (3H, m); 4.1–4.2 (4H, m); 6.2 (1H, s); 6.5–7.4 (14H, m). |

TABLE 7-continued

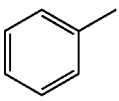

(I)

| Comp. No. | Substituents on the pyrrole ring in (I) | | | | n = | Mol. Wt. (mp ° C.) | Yield (% w/w) | $^1$H NMR (300 MHz, δ, CDCl$_3$) |
|---|---|---|---|---|---|---|---|---|
| | R$^1$ | R$^2$ | R$^3$ | R$^4$ | | | | |
| 21. | i-Pr | H | H | CH$_3$ | 2 | 387 | 32.4 | 1.15 (314, t, J=6.9 Hz); 1.2 (3H, t, J=6.9 Hz); 1.25 (6H, d, J=6.7 Hz); 2.27 (3H, s); 2.9–3.0 (3H, m); 3.3–3.63 (2H, m); 3.96 (1H, dd, ); 4.06 (2H, t, J=6.9 Hz); 4.14–4.24 (4H, m); 5.83 (2H, s); 6.73 (2H, d, J=8.5 Hz); 7.15 (2H, d, J=8.5 Hz). |
| 22. | i-Pr | H | H | i-Pr | 2 | 415 | 36 | 1.15 (3H, t, J=6.9 Hz); 1.23 (3H, t, J=?? Hz); 1.24–1.26 (12H, , J=6.7 Hz); 2.9 (4H, m); 3.35 1(H); 3.6 (1H, m); 3.95 (1H, dd, J=?? Hz); 4.05 (2H, t); 4.1–4.2 (2H, q, J$_1$ = 6.8 Hz, J$_2$ = 7.1 Hz); 4.23 (2H, t, J=6.6 Hz); 5.87 (2H, s); 6.75–6.76 (2H, d, J=8.6 H); 7.12–7.15 (2H, d, J=8.6 Hz) |
| 23. | i-Pr | H | H | (p-tolyl) | 2 | 449 | 31 | 1.14 (3H, t, J=6.99 Hz), 1.21 (3H, t, J=5.55 Hz); 1.31 (6H, d, J=6.15 Hz); 2.90 (2H, d, J=6.15 Hz); 3.32–3.57 (2H, m); 3.84 (2H, t, J=6.75 Hz); 3.91 (1H, t, J=3.55 Hz); 4.12–4.19 (2H, q, J$_1$ = 7.14 Hz, J$_2$ = 7.14 Hz); 4.33 (2H, t, J=6.8 Hz); 6.00 (1H, d, J=3.51 Hz); 6.12 (1H, d, J=3.51 Hz); 6.53 (2H, d, J=8.64 Hz); 6.93 (2H, d, J=8.7 Hz) 7.05 (2H, d, J=8.61 Hz); 7.31 7.40 (5H, m). |

TABLE 7-continued

Structure (I): pyrrole with substituents R¹ (position 2), R² (3), R³ (4), R⁴ (5); N-(CH₂)ₙ-O-C₆H₄-CH₂-CH(OC₂H₅)-C(=O)-OC₂H₅

| Comp. No. | R¹ | R² | R³ | R⁴ | n = | Mol. Wt. (mp ° C.) | Yield (% w/w) | ¹H NMR (300 MHz, δ, CDCl₃) |
|---|---|---|---|---|---|---|---|---|
| 24. | i-Pr | phenyl (C₆H₅) | H | i-Pr | 2 | 491 | 35 | 1.15 (3H, t, J=6.9 Hz); 1.22 (3H, t, J=7.1 Hz); 1.31 (6H, d, J=6 Hz); 2.90 (2H, dd); 3.33–3.35 (1H, m); 3.84 (2H, t, J=6.6 Hz); 3.33–3.58 (2H, m); 3.91–3.95 (1H, dd); 4.12–4.19(2H, q, J=7.0 Hz); 4.29 (2H, t, J=6.6 Hz); 6.55 (2H, d, J=8.6 Hz); 6.10 (1H, d, J=3.5 Hz); 5.98 (1H, d, J=3.4 Hz); 7.0–7.1 (4H, m); 7.3–7.38 (2H, m) |
| 25. | i-Pr | H | H | 4-methoxyphenyl (H₃CO-C₆H₄-) | 2 | 479 | 33 | 1.1 (3H, t, J=7 Hz); 1.2 (3H, t, J=7 Hz); 1.31 (6H, d, J=6 Hz); 3.0–3.1 (1H, m); 2.90 (2H, dd); 3.33 (2H. m); 3.8 (3H, s); 3.85 (2H, t,); 3.92 (1H, t); 4.12–4.16 (2H, q, J=7.14 Hz); 4.28 (2H, t, J=6.8 Hz); 5.98 (1H, d, J=3.4 Hz); 6.07 (1H, d, J=3.5 Hz); 6.56 (2H, d, J=8.6 Hz); 6.93 (2H, d, J=8.7 Hz); 7.32 (2H, d, J=8.5 Hz); 7.05 (2H, d, J=8.5 Hz); |
| 26. | i-Pr | H | H | 4-fluorophenyl (F-C₆H₄-) | 2 | 467 | 51 | 1.15 (3H, t, J=6.9 Hz); 1.22 (3H, t, J=7.1 Hz); 1.31 (6H, d, J=6 Hz); 2.90 (2H, dd); 3.33–3.35 (1H, m); 3.84 (2H, t, J=6.6 Hz); 3.33–3.58 (2H, m); 3.91–3.95 (1H, dd); 4.12–4.19(2H, q, J=7.0 Hz); 4.29 (2H, t, J=6.6 Hz); 6.55 (2H, d, J=8.6 Hz); 6.10 (1H, d, J=3.5 Hz); 5.98 (1H, d, J=3.4 Hz); 7.0–7.1 (4H, m); 7.3–7.38 (2H, m) |

TABLE 7-continued (I) — pyrrole ring with substituents $R^1, R^2, R^3, R^4$ and N-linked $(CH_2)_n$-O-C$_6$H$_4$-CH$_2$-CH(OC$_2$H$_5$)-C(=O)-OC$_2$H$_5$

| Comp. No. | Substituents on the pyrrole ring in (I) | | | | n = | Mol. Wt. (mp °C.) | Yield (%) w/w | $^1$H NMR (300 MHz, δ, CDCl$_3$) |
|---|---|---|---|---|---|---|---|---|
| | R$^1$ | R$^2$ | R$^3$ | R$^4$ | | | | |
| 27. | i-Pr | H | phenyl | 4-F-phenyl | 2 | 543 | 48 | 1.1 (3H, t, J=6.99 Hz); 1.2 (3H, t, J=7.1 Hz); 1.36 (6H, d, J=7 Hz); 2.9 (2H, d, J=6.29 Hz); 3.0–3.1 (1H, m); 3.3–3.58 (2H, m); 3.8 (2H, t, J=6.8 Hz); 3.9 (2H, t, J=7 Hz); 4.1–4.2 (4H, m); 6.2 (1H, s); 6.5–7.3 (13H, m). |
| 28. | i-Pr | Ph-NHCO | H | 4-F-phenyl | 2 | 586 | 20 | 1.15 (3H, t, J=6.9 Hz); 1.23 (3H, t, J=7.1 Hz); 1.51–1.53 (6H, d, J=7.1 Hz); 2.92 (2H, dd, J =?? Hz); 3.33–3.4 (1H, m); 3.5–3.6 (2H, Complex); 3.9–4.0 (3H, m); 4.1–4.2 (2H, q, J=?? Hz); 4.3–4.4 (2H, t, J=6.3 Hz); 6.31 (1H, s); 6.58–6.61 (2H, d, J=8.5 Hz); 7.0–7.2 (4H, m); 7.3–7.4 (4H, m); 7.5 (1H, s); 7.6 (2H, d, J=7.6 Hz) |
| 29. | i-Pr | Ph-NHCO | phenyl | 4-F-phenyl | 2 | 662 | 44 | 1.08 (3H, t, J=7.0 Hz); 1.16 (3H, t, J=7.0 Hz); 1.49 (6H d, J=7 Hz); 2.85 (2H, dd) 3.26 (1H, m); 3.5 (2H, m) 3.87 (2H, t); 3.9 (1H, t); 4.09 (2H, q); 4.19 (2H, t); 6.53 (2H, d, J=8.5 Hz) 6.79 (1H, s); 6.90–7.18 (16H, m) |
| 30. | i-Pr | Ph-NHCO | phenyl | 4-F-phenyl | 3 | 676 | 89 | 1.14 (2H, t, J=6.9 Hz) 1.22 (3H, t, J=7 Hz); 1.53 (6H, d, J=7 Hz); 1.97 (2H, m); 2.91 (2H, dd) 3.32 (1H, m); 3.56 (2H, m); 3.76 (2H, t); 3.93 (1H, t); 4.07 (2H, t); 4.15 (2H, q, J=7 Hz); 6.62–6.65 (2H, d); 6.84 (1H, s); 6.9–6.98 (3H, m); 7.03–7.05 (2H, d); 7.09–7.18 (10H, m). |

TABLE 7-continued (I)

| Comp. No. | Substituents on the pyrrole ring in (I) | | | | n = | Mol. Wt. (mp ° C.) | Yield (%) w/w | $^1$H NMR (300 MHz, δ, CDCl$_3$) |
|---|---|---|---|---|---|---|---|---|
| | R$^1$ | R$^2$ | R$^3$ | R$^4$ | | | | |
| 31. | phenyl-CH | H | H | 4-F-phenyl | 2 | 501 | 15 | 1.12 (3H, t, J=7.0 Hz); 1.21 (3H, t, J=7.0 Hz); 2.88 (2H, d, J=6.0 Hz); 3.3 (1H, m); 3.6 (1H, m); 3.61 (2H, t); 3.9 (1H, m); 4.1 (2H, t, J=7.9 Hz); 4.37 (2H, t, J=6.0 Hz); 6.26 (2H, dd, J=3.3 Hz); 6.9 (2H, d, J=9.0 Hz); 7.1 (2H, m); 7.41–7.49 (9H, m). |
| 32. | phenyl | —COOEt | H | 4-F-phenyl | 2 | 573 | 13.5 | 1.1–1.25 (9H, m); 2.8 (2H, d, J=6.3 Hz); 3.3 (1H, m); 3.6 (1H, m), 3.61 (2H, m); 3.9 (1H, t); 4.1–4.21 (6H, m); 6.3 (1H, s); 6.9 (2H, d, J=9.0 Hz); 7.1 (2H, m); 7.42–7.47 (9H, m) |
| 33. | SCH$_3$ | H | H | H | 2 | 377 | 20 | 1.14(3H, t, J=7.0 Hz); 1.24 (3H, t, J=7.0 Hz); 2.29 (3H, s); 2.90–2.94 (2H, m); 3.30–3.40 (1H, m); 3.54–3.62 (1H, m); 3.95(1H, t, J=3.6 Hz); 4.13–4.22 (4H, m); 4.40 (2H, t, J=5.6 Hz); 6.15 (2H, d, J=3.2 Hz); 6.37 (1H, dd); 6.80 (2H, d, J=8.5 Hz); 6.94 (1H, m); 7.15 (2H, d, J=8.5 Hz). |

Preparation 11

(S)-Methyl 3-{4-[2-(2,5-dimethylpyrrol-1-yl)ethoxy]phenyl}-2-methoxypropanoate (Example 34)

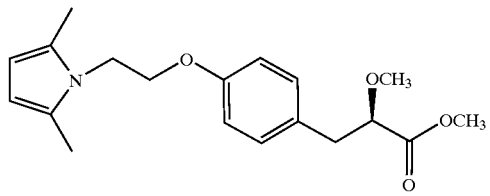

(I)

Using a similar procedure to that described in preparation 8, (S)-methyl 3-(4-hydroxyphenyl)-2-methoxypropanoate (3.3 g), and mesylate (Compound. No. 41, 4.38 g), gave the titled compound (1.2 g, 20%).

In the like manner to that described in above example, the corresponding propoxy derivative (Example no. 35) was prepared using (S)-Propyl 3-(4-hydroxyphenyl)-2-propoxy propionate and mesylate (given in the Table 8).

TABLE 8

Structure (I): Pyrrole with R¹, R², R³, R⁴ substituents, N-linked to ethoxy-phenyl-CH₂-CH(OR)-C(=O)-OR

| Ex No. | Substituents on the pyrrole ring in (I) R¹ | R² | R³ | R⁴ | R = | Mol. Wt. (mp ° C.) | Yield (% w/w) | ¹H NMR (300 MHz, δ, CDCl₃) |
|---|---|---|---|---|---|---|---|---|
| 34. | CH₃ | H | H | Phenyl | CH₃ | 393 | 20 | 2.37 (3H, s); 3.33 (3H, m); 3.71 (3H, m); 3.92 (3H, t, J=6.96 Hz); 4.29 (3H, t, J=6.6 Hz); 5.97 (1H, d, J=3.36 Hz); 6.11 (1H, d, J=3.39 Hz); 6.6 (2H, d, J=8.67 Hz); 7.05 (2H, d, J=8.64 Hz); 7.30–7.40 (5H, m). |
| 35. | CH₃ | H | H | Phenyl | C₃H₇ | 449 | 20 | 0.83 (3H, t, J=7.4 Hz); 0.89 (3H, t, J=7.4 Hz); 1.53–1.63 (4H, m); 2.37 (3H, s); 2.91 (2H, d, J=5.54 Hz); 3.20–3.48 (2H, m); 3.92 (6H, t, J=6.59 Hz); 4.06 (2H, J=6.67 Hz); 4.28 (2H, t, J=7.4 Hz); 5.97 (1H, d, J=3.39 Hz); 6.11 (1H, d,J=3.4 Hz); 6.59 (2H, d, J=8.64 Hz); 7.07 (2H, d, J=8.63 Hz); 7.25–7.4 (5H, m). |

Preparation No. 12

Ethyl (E/Z) 2-ethoxy-3-[4-[2-(5-methyl-2-phenylpyrrol-1-yl)ethoxy]phenyl]prop-2-enoate (Example 36)

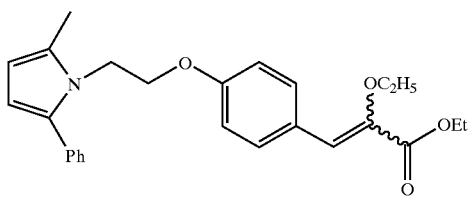

To a solution of triethyl 2-ethoxyphosphonoacetate (12.5 g) in dry THF (60 mL) was added slowly to a well-stirred ice-cold suspension of NaH (1.8 g, 60% dispersion in oil) in dry THF (60 mL) under N₂ atmosphere. The reaction mixture was stirred at 0° C. for 30 min. and 4-[2-(5-methyl-2-phenylpyrrol-1-yl)ethoxy]benzaldehyde (compound no. 65) (10.8 g) in dry THF (80 mL) was added. The mixture was allowed to warm up to 20° C. to 25° C. and stirred for 3.5 hrs. The solvent was evaporated and the residue was diluted with water (150 mL) further the product was extracted with ethyl acetate (2×150 mL). The combined extract was washed with water (150 mL), brine (50 mL), and was dried over sodium sulfate. The solvent was evaporated under reduced pressure to afford crude product. The crude product was chromatographed over silica gel using pet. ether: ether (9:1) as an eluent to afford E and Z isomers, which were isolated by removing the of solvents.

TABLE 9

| Ex. No. | Substituents on the pyrrole ring R¹ | R² | R³ | R⁴ | Mol. Wt. (mp° C.) | Yield (% w/w) | ¹H NMR (300 MHz, δ, CDCl₃) |
|---|---|---|---|---|---|---|---|
| 36. | CH₃ | H | H | Phenyl | 419 | 40 | E/Z-isomer |
| 37. | CH₃ | H | H | Phenyl | 419 | 15 | E-isomer |

TABLE 9-continued

| Ex. No. | Substituents on the pyrrole ring | | | | Mol. Wt. (mp° C.) | Yield (% w/w) | $^1$H NMR (300 MHz, δ, CDCl$_3$) |
|---|---|---|---|---|---|---|---|
| | R$^1$ | R$^2$ | R$^3$ | R$^4$ | | | |
| | | | | | | | 1.13 (3H, t, J=7.14 Hz); 1.4 (3H, t, J=6.9 Hz); 2.3 (3H, s); 3.86–3.95 (4H, m); 4.13 (2H, q, J=7.1 Hz); 4.27–4.31 (2H, t, J=6.6 Hz); 5.96 (1H, d, J=3.3 Hz); 6.03 (1H, s); 6.11 (1H, d, J=3.3 Hz); 6.5–6.6 (2H, d, J=8.7 Hz); 7.03–7.06 (2H, d, J=8.5 Hz); 7.32–7.34 (1H, m); 7.35–7.41 (4H, m). |
| 38. | CH$_3$ | H | H | Phenyl | 419 | 15 | Z-isomer 1.33–1.38 (6H, t, J=7.0 Hz); 2.38 (3H, s); 3.92–3.99 (4H, m); 4.24–4.33 (4H, m); 5.98 (1H, d, J=3.3 Hz); 6.11 (1H, d, J=3.3 Hz); 6.63–6.6 (1H, d, J=8.9 Hz); 6.92 (1H, s); 7.33 (1H, m); 7.36–7.41 (4H, m); 7.64–7.67 (2H, d, J=8.8 Hz). |

Preparation 13

(R/S) Ethyl 2-ethoxy-3-[4-[2-[2-methyl-5-phenyl-1H-pyrrol-1-yl]ethoxy]phenyl] propanoate

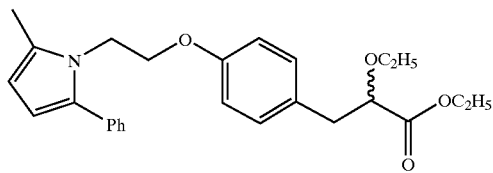

Mixture of E/Z compounds (Example no. 36 and 37) obtained in preparation 12 (7.1 g, 0.016 mole) and magnesium turnings (7.3 g, 0.3 mole) in dry methanol (70 mL) was stirred at 25° C. for 3.5 hrs. H$_2$O (150 mL) was added and pH of the reaction mixture was adjusted to 2-3 with 35% hydrochloric acid. The product was extracted in ethyl acetate (2×100 mL) combined extract was washed with H$_2$O (2×100 mL) brine (100 mL) and dried over Na$_2$SO$_4$ The extract was concentrated under reduced pressure. The crude product was chromatographed over silica gel using pet. ether:ether (9:1) as an eluent. The product obtained was racemic mixture.

Alternatively, the E and Z compound mixture is hydrogenated in the presence of 10% Pd/C catalyst at 60 psi pressure to obtain the title compound.

TABLE 10

| Ex. No. | Substituents on the pyrrole ring | | | | Mol. Wt. (mp° C.) | Yield (% w/w) | $^1$H NMR (300 MHz, δ, CDCl$_3$) |
|---|---|---|---|---|---|---|---|
| | R$^1$ | R$^2$ | R$^3$ | R$^4$ | | | |
| 39. | CH$_3$ | H | H | Phenyl | 407 | 50 | 1.15 (6H, t, J=7.0 Hz); 2.37 (3H, s); 2.90–2.92 (2H, dd); 3.32–3.35 (1H, m); 3.55–3.57 (1H, m); 3.69 (3H, s); 3.90–3.97 (3H, m); 4.29 (2H, t, J=6.9 Hz); 5.9 (1H, d, J=3.4 Hz); 6.1 (1H, d, J=3.4 Hz); 6.59 (2H, d, J=8.6 Hz); 7.05 (2H, d, J=8.5 Hz); 7.26–7.41 (5H, m). |

Preparation 14

(S)-3-{4-[2-(2,5-Dimethylpyrrol-1-yl)ethoxy]phenyl}-2-ethoxypropanoic acid (Example 40)

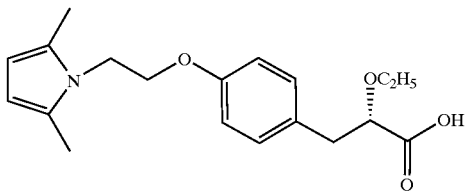

A mixture of substituted ester (prepared in example 2) (1.38 g), sodium hydroxide (3.0%, 15 mL) in methanol (20 mL) was stirred at 20° C. to 25° C. for 10 h. Methanol was evaporated under reduced pressure. The residue was diluted with water (20 mL) and was acidified with dilute hydrochloric acid. The product was extracted with ethyl acetate (3×20 mL) and washed with water (2×80 mL), brine (80 mL) and was dried over sodium sulfate to obtain an oily product (1.2 g, 94%). The crude product (3 g) was separated by column chromatography using silica gel using hexane:ethyl acetate (9:1) as an eluent to afford the pure title compound (0.75 g, 59%).

In like manner to that described in Preparation 14 above following compounds of the formula (I) (given in Table 11) were prepared from the appropriately substituted pyrrole derivatives described elsewhere:

TABLE 11

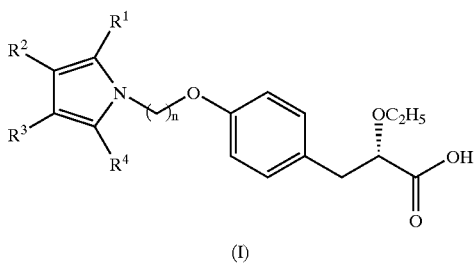

(I)

| Ex No. | \multicolumn{4}{c}{Substituents on the pyrrole ring in (I)} | | Mol. Wt. | Yield | $^1$H NMR |
|---|---|---|---|---|---|---|---|---|
| | $R^1$ | $R^2$ | $R^3$ | $R^4$ | N = | (mp ° C.) | (% w/w) | (300 MHz, δ, CDCl$_3$) |
| 40. | H | H | H | H | 2 | 303 | 79 | 1.16 (3H, t, J=6.9 Hz); 2.97(1H, dd); 3.0 (1h, dd); 3,36–3.6 (2H, m); 4.01 (1H, dd); 4.17–4.28 (4H, m) 6.16 (2H, t, J=2.1 Hz); 6.75–6.80 (4H,m); 6.7 (2H, t, 2.1 Hz); 6.8 (2H, d, J=8.5 Hz); 7.15 (2H, d, J=8.5 Hz). |
| 41. | CH$_3$ | H | H | CH$_3$ | 2 | 331.2 (102) | 59 | 1.18 (3H, t, J=7 Hz); 2.28 (6H, s); 2.93–3.08 (2H, m); 3.45–3.59 (2H, m); 4.03–4.18 (5H, m); 5.79 (1H, s); 6.78(2H, d, J=8.5 Hz); 7.15 (2H,d, J=8.5 Hz). |
| 42. | CH$_3$ | 14 | CH$_3$ | H | 2 | 331 | 88 | 0.96 (3H, t, J=6.76 Hz); 1.9 (3H, s); 2.13 (3H, s), 2.78 (2H, m); 3.3–3.6 (2H, m); 4.05 (5H, m); 5.53 (1H, s); 6.43 (1H, s 6.75 (2H, d, J=9.0 Hz); 7.07 (2H, d, J=9.0 Hz). |
| 43. | C$_2$H$_5$ | H | H | H | 2 | 331 | 10 | 1.16 (3H, t, J=6.9 Hz); 1.27 (3H, t, J=3.51 Hz); 2.62 (2H, q); 3.44–3.46 (2H, m); 4.03 (1H, dd, J$_1$ = 4.23 Hz, J$_2$ = 4.5 Hz); 4.13 (2H, t, J=5.2 Hz); 4.18 (2H, t, J=3.76 Hz); 5.91–5.92 (1H, m) 6.10 (1H, t, J=3.12 Hz); 6.70 (1H, d, J=2.01 Hz); |

TABLE 11-continued

Structure (I): Pyrrole with substituents R¹, R², R³, R⁴ connected via N–(CH₂)ₙ–O– to a para-substituted phenyl bearing a –CH₂–CH(OC₂H₅)–COOH group.

| Ex No. | Substituents on the pyrrole ring in (I) | | | | N = | Mol. Wt. (mp °C.) | Yield (% w/w) | ¹H NMR (300 MHz, δ, CDCl₃) |
|---|---|---|---|---|---|---|---|---|
| | R¹ | R² | R³ | R⁴ | | | | |
| 44. | CHO | H | H | H | 2 | 331 | 75 | 6.77 (2H, d, J=8.7 Hz); 7.135 (2H, d, J=8.64 Hz). 1.10 (2H, t, J=7 Hz); 2.8–3.8 (5H, m); 4.16 (2H, t, J=4.9 Hz); 4.65 (2H, t, J=4.9 Hz); 6.22 (1H, dd) 6.7 (2H, d, J=8.5 Hz); 7.1 (2H, d, J=8.5 Hz); 9.49 (1H, s). |
| 45. | COCH₃ | H | H | H | 2 | 345 | 10 | 0.87 (3H, t, J=6.87 Hz); 2.39 (3H, s); 2.66 (2H, dd, J=11.55 Hz); 2.95–3.06 (2H, m); 3.73 (1H, t, J=4.5 Hz); 4.09 (3H, t, J=4.74 Hz); 4.60 (2H, t, J=4.89 Hz); 6.08 (1H, dd, J₁ = 2.64 Hz, J₂ = 2.64 Hz); 6.58 (2H, d, J=8.37 Hz); 6.92–6.99 (2H, m); 7.00 (2H, d, J=8.34 Hz). |
| 46. | CH₃ | H | H | CH₂CH₃ | 2 | 345 | 54 | 1.16 (3H, t, J=7 Hz); 1.28 (3H, t, J=7Hz); 2.28 (3H, m); h 2.55 (2H, t, J=7.4 Hz); 3.06 (2H, dd); 3.4–3.62 (2H, m); 4.0–4.16 (5H, m); 5.8–5.84 (2H, m); 6.75 (2H, d, J=6.78 Hz); 7.14 (2H, d, J=6.78 Hz). |
| 47. | CH₃ | H | H | (CH₂)₂CH₃ | 2 | 423 | 66 | 1.02 (3H, t, J=6.9 Hz); 1.17 (3H, t, J=6.9 Hz); 1.7 (2H, sextet); 2.28 (3H, s); 2.55 (2H, t, J=7.7 Hz); 2.94 (1H, dd); 3.4 (1H, dd); 3.4–3.62 (2H, m); 4.0–4.2 (5H, m); 5.8–5.84 (2H, m); 6.75 (2H, d, J =8.5 Hz); 7.14 (2H, d, J=8.5 Hz). |
| 48. | CH₃ | H | H | (CH₂)₃CH₃ | 2 | 373 | 76 | 0.95 (3H, t, J=7.2 Hz); 1.17 (3H, t, J=7.0 Hz); 1.4–1.5 (2H, m); 1.6–1.7 (2H, m); 2.28 (3H, s); 2.57 (2H, t, J=7.7 Hz); 2.95 (1H, dd); 3.07 (1H, dd); 3.4–3.5 (1H, m); 3.53–3.62 (1H, m); 4.0–4.2 (5H, m); 5.8–5.83 (2H, m); 6.77 (2H, d, J=8.5 Hz); 7.15 (2H, d, J=8.5 Hz). |

TABLE 11-continued

Structure (I): Pyrrole ring with substituents R¹, R², R³, R⁴ on positions, N-linked via -(CH₂)ₙ-O- to a para-substituted phenyl group bearing -CH₂-CH(OC₂H₅)-COOH

| Ex No. | R¹ | R² | R³ | R⁴ | N = | Mol. Wt. (mp °C.) | Yield (% w/w) | ¹H NMR (300 MHz, δ, CDCl₃) |
|---|---|---|---|---|---|---|---|---|
| 49. | $CH_3$ | H | H | phenyl | 2 | 393 | 96 | 1.16 (3H, t, J=6.9 Hz); 2.37 (3H, s); 2.92–3.02 (2H, dd, J₁ = 7 Hz, J₂ = 4.2 Hz); 3.41–3.58 (2H, m); 3.92 (2H, t); 3.98–4.01 (1H, m); 4.1–4.3 (2H, t, J=6.5 Hz); 5.96 (1H, d, J=3.3 Hz); 6.1 (1H, d, J=3.3 Hz); 6.6 (2H, d, J=8.5 Hz); 7.06–7.09 (2H, d, J=8.5 Hz); 7.2–7.4 (5H, m). |
| 50. | $CH_3$ | H | phenyl | H | 2 | 393 | 96 | 1.16 (3H, t, J=6.9 Hz); 2.37 (3H, s); 2.92–3.02 (2H, dd, J₁ = 7 Hz, J₂ = 4.2 Hz); 3.41–3.58 (2H, m); 3.92 (2H, t); 3.98–4.01 (1H, m); 4.1–4.3 (2H, t, J=6.5 Hz); 5.96 (1H, d, J=3.3 Hz); 6.1 (1H, d, J=3.3 Hz); 6.6 (2H, d, J=8.5 Hz); 7.0 (2H, d, 8.5 Hz); 7.06–7.09 (2H, d, J=8.6 Hz); 7.2–7.4 (5H, m). |
| 51. | $CH_3$ | H | H | 4-methylphenyl | 2 | 407 | 75 | 1.02 (3H, t, J=6.9 Hz); 2.34 (3H, s); 2.36 (3H, s); 2.74 (1H, dd); 3.0 (1H, dd); 3.19–3.22 (1H, m); 3.4–3.45 (1H, m); 3.78–3.79 (1H, m); 3.8 (2H, t, J=6.4 Hz); 4.25 (2H, t, J=6.4 Hz), 5.96 (1H, d, J=3.36 Hz), 6.1 (1H, d, J=8.5 Hz); 6.6 (2H, d, J=8.5 Hz); 7.19 (2H, d, J=8.5 Hz); 7.28 (2H, d, J=8.5 Hz). |
| 52. | $CH_3$ | H | H | 3-methylphenyl | 2 | 407 | 100 | 1.25 (3H, t, J=7.15 Hz), 2.37 (3H, s); 3.0 (1H, m); 3.41–3.58 (2H, dd); 3.91 (2H, t, J=6.58 Hz); 4.00 (1H, dd, J=4.29 Hz); 6.07 (1H, d, J=3.42 Hz); 6.6 (2H, d, J=8.6 Hz); 7.07 (2H, d, J=8.58 Hz); 7.14–7.28 (4H, m). |

TABLE 11-continued

Structure (I): pyrrole ring substituted with R¹, R², R³, R⁴ on positions, N-linked via -(CH₂)ₙ-O- to a para-substituted phenyl bearing a -CH₂-CH(OC₂H₅)-COOH group (S-configuration).

| Ex No. | R¹ | R² | R³ | R⁴ | N = | Mol. Wt. (mp °C.) | Yield (% w/w) | ¹H NMR (300 MHz, δ, CDCl₃) |
|---|---|---|---|---|---|---|---|---|
| 53. | CH₃ | H | H | 2-methylphenyl (o-tolyl, CH₃) | 2 | 407 | 20 | — |
| 54. | CH₃ | H | H | 4-methoxyphenyl (H₃CO-C₆H₄-, with CH₃) | 2 | 423 | 62 | 1.077 (3H, t, J=7 Hz); 2.368 (3H, s); 2.93 (3H, s); 2.94 (1H, m); 3.35–3.5 (2H, m); 3.78 (1H, J=7.1 Hz); 3.8 (3H, m); 3.9 (2H, tJ=7 Hz); 4.25 (2H, t, J=7 Hz); 5.9 (1H, d, J=3.36 Hz); 6.0 (1H, d, J=3.36 Hz); 6.64 (2H, d, J=8.5 Hz); 7.1 (2H, d, J=8.5 Hz); 7.31 (2H, d, J=6.78 Hz). |
| 55. | CH₃ | H | H | 4-bromophenyl (Br-C₆H₄-, with CH₃) | 2 | 472 | 84 | 1.02 (3H, t, J=6.9 Hz); 2.353 (3H, s); 2.74 (1H, dd); 2.95 (1H, dd); 3.19–3.28 (1H, m); 3.4–3.45 (1H, m); 3.8 (1H, dd); 3.9 (2H, t, J=6.21 Hz); 4.26 (2H, t, J=6.2 Hz); 5.9 (1H, d, J=3 Hz); 6.1 (2H, d, J=3.4 Hz); 6.6 (2H, d, J=8.5 Hz); 7.1 (2H, d, J=8.5 Hz), 7.29 (2H, d, J=8.5 Hz) |
| 56. | CH₃ | H | H | 4-fluorophenyl (F-C₆H₄-, with CH₃) | 2 | 419 | 77 | 1.02 (3H, t, J=6.9 Hz), 2.3 (3H, s); 2.7–2.8 (1H, m); 2.96 (1H, m); 3.1–3.2 (1H, m); 3.4–3.5 (1H, m); 3.86–3.91 (2H, t, J=63 Hz), 4.2–4.24 (2H, t, J=6.3 Hz); 5.9 (1H, d, J=3.3 Hz), 6.05 (1H, d, J=3.3 Hz); 6.56–6.59 (2H, d, J=8.6 Hz); 7.05–7.09 (4H, m); 7.28–7.37 (2H, m). |
| 57. | CH₃ | H | H | 4-chlorophenyl (Cl-C₆H₄-, with CH₃) | 2 | 427.5 | 37 | — |

TABLE 11-continued

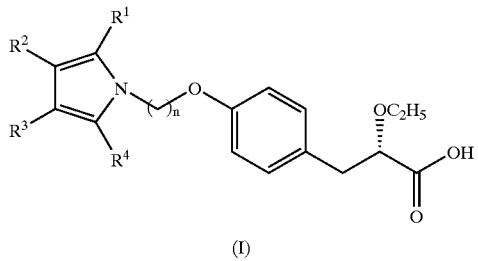

(I)

| Ex No. | Substituents on the pyrrole ring in (I) | | | | N = | Mol. Wt. (mp °C.) | Yield (% w/w) | $^1$H NMR (300 MHz, δ, CDCl$_3$) |
|---|---|---|---|---|---|---|---|---|
| | R$^1$ | R$^2$ | R$^3$ | R$^4$ | | | | |
| 58. | phenyl | H | CH$_3$ | H | 2 | 393 | 41 | — |
| 59. | CH$_3$ | H | phenyl | phenyl | 2 | 469 | 83 | 1.16 (3H, t, J=7 Hz); 2.41 (3H, s); 2.9 (1H, dd); 3.05 (1H, dd); 3.4–3.6 (2H, m); 3.9 (2H, t, J=6.5 Hz); 4.03 (1H, dd); 4.16 (2H, t, J=6.5 Hz); 6.2 (2H, s); 6.5–7.4 (14H, m). |
| 60. | i-Pr | H | H | CH$_3$ | 2 | 359 | 20 | 1.17 (3H, t, J=6.9 Hz); 1.26 (6H, d, J=6.7 Hz); 2.27 (3H, s); 2.9–3.0 (1H, m); 3.07 (1H, dd); 3.42–3.58 (2H, m); 4.02–4.08 (3H, m); 4.2 (2H, t, J=6.3 Hz); 5.83 (2H, s); 6.7 (2H, d, J=8 Hz); 7.15 (2H, d, J=8 Hz). |
| 61. | i-Pr | H | H | i-Pr | 2 | 387 | 50 | 1.19 (3H, t, J=6.8 Hz); 1.24–1.26(12H, d, J=6.7 Hz); 2.92–2.99 (4H, complex); 3.40 (1H, m); 3.6 (1H, m); 4.03 (3H, complex); 4.24 (2H, J Hz); 5.87 (2H, s); 6.75–6.76 (2H, d, J=?? Hz), 7.13–7.15 (6H, d, J=8.6 Hz) |
| 62. | i-Pr | H | H | phenyl | 2 | 443 | 87 | 0.94 (3H, t, J=7.29 Hz); 1.22 (6H, d, J=7.29 Hz); 2.49–2.51(2H, dd, J= 6.75 Hz); 3.03–3.08 (1H, m); 3.45–3.53 (1H, t, J=4.5 Hz); 3.82 (2H, t, J=5.91 Hz); 4.29 (2H, t, J = 5.92 Hz); 5.85 (1H, d, J=3.51 Hz); 5.95 (1H, d, J=3 Hz); 6.52 (2H, d, J=8.58 Hz); 7.01 (2H, d, J=8.52 7.29–7.40 (5H, m). |

TABLE 11-continued

Structure (I): Pyrrole ring with substituents R¹, R², R³, R⁴ on the ring, N-linked to -(CH₂)ₙ-O-C₆H₄-CH₂-CH(OC₂H₅)-C(=O)-OH

| Ex No. | R¹ | R² | R³ | R⁴ | N = | Mol. Wt. (mp °C.) | Yield (% w/w) | ¹H NMR (300 MHz, δ, CDCl₃) |
|---|---|---|---|---|---|---|---|---|
| 63. | i-Pr | phenyl | H | i-Pr | 2 | 463 | 48 | 1.12 (3H, t, J=6.9 Hz); 1.2–1.3 (12H, m); 2.96–3.76 (7H, m); 4.03–4.05 (2H, m); 4.30 (2H, t, J=6.9 Hz); 5.89 (1H, s); 6.80 (2H, d, J=8.5 Hz); 7.15 (2H, d, J=8.5 Hz); 7.2–7.33 (5H, m). |
| 64. | i-Pr | H | H | 4-methoxyphenyl (H₃CO-C₆H₄-) | 2 | 451 | 84 | 1.2 (3H, t, J=7 Hz); 1.29 (6H, d, J=6 Hz); 2.90 (2H, dd); 3.04–3.06 (1H, m); 3.33–3.59 (2H, m); 3.8 (3H, s); 4.0 (1H, t); 3.84 (2H, t, J=6 Hz); 4.28 (2H, t, J=6.7 Hz); 5.98 (1H, d, J=3.4 Hz); 6.56 (2H, d, J=8.6 Hz); 6.08 (1H, d, J=3.5 Hz); 6.93 (2H, d, J=8.7 Hz); 7.03 (2H, t, J=8.5 Hz); 7.32 (2H, d, J=8.5 Hz). |
| 65. | i-Pr | H | H | 4-fluorophenyl (F-C₆H₄-) | 2 | 439 | 36 | 1.17 (3H, t, J=6.9 Hz); 1.31 (6H, d, J=6.9 Hz); 2.93 (2H, dd); 3.03–3.1 (1H, m); 3.33–3.58 (2H, m); 3.84 (2H, t, J=6.5 Hz); 4.0 (1H, m); 4.29 (2H, t, J=6.6 Hz); 6.56 (2H, d, J=8.6 Hz); 6.10 (1H, d, J=3.5 Hz); 6.00 (1H, d, J=3.5 Hz); 7.0–7.1 (4H, m); 7.3–7.38 (2H, m). |
| 66. | i-Pr | H | phenyl | 4-fluorophenyl | 2 | 515 (127-128) | 53 | 1.19 (3H, t, J=6.9 Hz); 1.36 (6H, d, J=7 Hz); 2.95 (2H, dd, J=7.1 Hz); 3.0–3.1 (1H, m); 3.45–3.57 (2H, m); 3.83 (2H, t, J=6.5 Hz); 4.0–4.04 (1H, m); 4.2 (2H, t, J=6.7 Hz); 6.2 (1H, s); 6.5–7.28 (13H, m). |

TABLE 11-continued

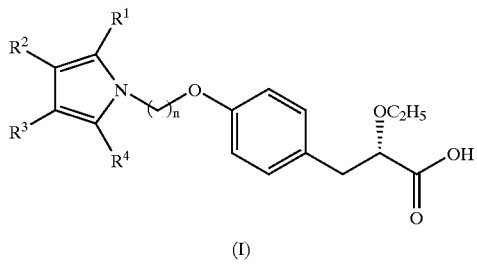

(I)

| Ex No. | Substituents on the pyrrole ring in (I) | | | | N = | Mol. Wt. (mp °C.) | Yield (% w/w) | ¹H NMR (300 MHz, δ, CDCl₃) |
|---|---|---|---|---|---|---|---|---|
| | R¹ | R² | R³ | R⁴ | | | | |
| 67. | i-Pr | Ph-NHCO | H | 4-F-C₆H₄ | 2 | 558 | 50 | 1.18 (3H, t, J=6.9 Hz); 1.51–1.53 (6H, d, J=7 Hz); 2.9–3.1(2H, dd, J=?? Hz); 3.5–3.6 (3H, Complex); 3.92 (2H, t, J=6.2 Hz); 4.05 (1H, dd, J=?? Hz); 4.3 (2H, t, J=6.2 Hz); 6.31(1H, s); 6.58–6.60 (2H, d, J=6.7 Hz); 7.1 (4H, m); 7.30–7.38 (4H, m) 7.5 (1H, s); 7.58–7.59 (2H, d) |
| 68. | i-Pr | Ph-NHCO | 4-Me-C₆H₄ | 4-F-C₆H₄ | 2 | 634 (112–114) | 61 | 0.91 (3H, t, J=6.7 Hz); 1.45(6H, d, J=6.8 Hz); 2.91 (2H, dd); 3.13 (1H, m); 3.32–3.49 (2H, m); 3.80 (3H, m) 4.15 (2H, J=6.5 Hz); 6.46 (2H, d); 6.78 (1H, s); 6.86–7.18 (16H, m). |
| 69. | i-Pr | Ph-NHCO | 4-Me-C₆H₄ | 4-F-C₆H₄ | 3 | 648 (114–116) | 24 | 1.1 (3H, t, J=7 Hz); 1.47 (6H, d, J=7 Hz); 1.91 (2H, m); 3.01 (2H, dd); 3.41 (1H, m); 3.98 (1H, t); 3.71 (2H, t, J=6Hz); 4.02 (2H, t, J=7.2 Hz); 6.59 (1H, t); 6.78 (1H, s); 6.9 (2H, m); 7.1 (10H, m). |
| 70. | Ph | —H | H | 4-F-C₆H₄ | 2 | 473 | 60.3 | 0.9 (3H, t); 2.6 (1H, t); 3.5 (2H, t); 3.6 (1H, m); 6.21 (2H, dd, J=3 Hz); 6.9 (2H, d); 7.0 (2H, t, J=9.0 Hz); 7.31–7.6 (9H, m). |
| 71. | Ph | —COOEt | H | 4-F-C₆H₄ | 2 | 545 | 83 | 0.9 (3H, t); 2.6 (1H, t); 2.9 (2H, d); 3.2 (1H, m); 3.5 (2H, t); 3.6 (1H, m); 6.7 (1H, s); 6.9 (2H, d); 7.1 (2H, t); 7.29–7.6 (9H, m). |

TABLE 11-continued

Structure (I): Pyrrole (with substituents R¹, R², R³, R⁴ on ring) — N-(CH₂)ₙ—O—C₆H₄—CH₂—CH(OC₂H₅)—C(=O)OH

| Ex. No. | Substituents on the pyrrole ring in (I) | | | | N = | Mol. Wt. (mp °C.) | Yield (% w/w) | ¹H NMR (300 MHz, δ, CDCl₃) |
|---|---|---|---|---|---|---|---|---|
| | R¹ | R² | R³ | R⁴ | | | | |
| 72. | SCH₃ | H | H | H | 2 | 349 | 93 | 1.18 (2H, t, J=7 Hz); 2.29 (3H, s); 2.9–3.1 (2H, m); 3.4–3.6 (2H, m); 4.0–4.04 (1H, m); 4.2 (2H, t, J=5.6 Hz); 4.42 (2H, t, J=5.6 Hz); 6.1 (1H, t, J=3.2 Hz); 6.38 (1H, dd); 6.8 (2H, d, J=8.5 Hz); 6.95 (1H, dd); 7.15 (2H, d, J=8.5 Hz). |

Preparation 15

(E/Z) 3-{4-[2-(5-methyl-2-phenylpyrrol-1-yl)ethoxy]phenyl}-2-ethoxypropane-2-oic acid In a like manner to the procedure given in Preparation 14, the esters described in examples 36, 37 and 38 can be converted to a corresponding acid.

TABLE 12

(Example 73)

Structure (1h): Pyrrole (with substituents R¹, R², R³, R⁴) — N-CH₂CH₂—O—C₆H₄—CH=C(OC₂H₅)—C(=O)OH

| Ex. No. | Substituents on the pyrrole ring in (1h) | | | | Mol. Wt. (mp °C.) | Yield (% w/w) | ¹H NMR (300 MHz, δ, CDCl₃) |
|---|---|---|---|---|---|---|---|
| | R¹ | R² | R³ | R⁴ | | | |
| 73. | CH₃ | H | H | Phenyl | 391 | 59 | (E/Z) |
| 74. | CH₃ | H | H | Phenyl | 391 | 25 | E-isomer 1.35(3H, t, J=6.8Hz); 2.36(3H, s); 3.8–3.9(4H, m); 4.28(2H, t, J=6.4Hz); 5.5(1H, s); 5.9(1H, d, J=3.3Hz); 6.0(1H, d, J=3.3Hz); 6.5(2H, d, J=8.7Hz); 7.1(2H, d, J=8.6Hz) 7.3–7.4(5H, m). |

TABLE 12-continued (Example 73)

| Ex. No. | Substituents on the pyrrole ring in (1h) | | | | Mol. Wt. (mp ° C.) | Yield (% w/w) | $^1$H NMR (300 MHz, δ, CDCl$_3$) |
|---|---|---|---|---|---|---|---|
| | R$^1$ | R$^2$ | R$^3$ | R$^4$ | | | |
| 75. | CH$_3$ | H | H | Phenyl | 391 | 25 | Z-isomer 1.37(3H, t, J=7.0Hz); 2.3(3H, s); 3.9–4.02(4H, m); 4.3(2H, t, J=26.4Hz); 5.9(1H, d, J=3.2Hz); 6.1(1H, d, J=3.2Hz); 6.6(1H, d, J=8.8Hz); 7.0(1H, s); 7.26–7.42(5H, m); 7.6(2H, d, J=8.8Hz). |

Preparation 16

(R/S) 3-{4-[2-(5-methyl-2-phenylpyrrol-1-yl)ethoxy]phenyl}-2-ethoxypropanoic acid (Example 76)

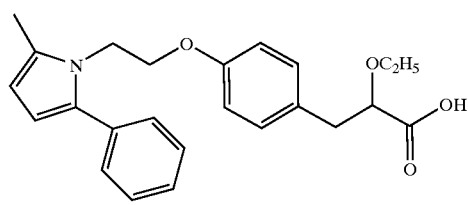

(I)

Using the procedure similar to that described in Preparation 14, the racemic ester (Example 39) was hydrolysed to its corresponding acid.

Preparation 17

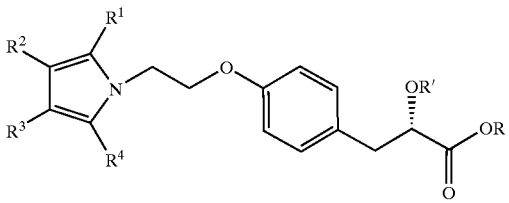

(I)

Using the procedure similar to that described in Preparation 14, the methoxy and propoxy ester (Example 34 and 35) was hydrolysed to its corresponding acid.

TABLE 13

| Ex. No. | Substituents on the pyrrole ring | | | | Mol. Wt. (mp° C.) | Yield (% w/w) | $^1$H NMR (300 MHz, δ, CDCl$_3$) |
|---|---|---|---|---|---|---|---|
| | R$^1$ | R$^2$ | R$^3$ | R$^4$ | | | |
| 76. | CH$_3$ | H | H | Phenyl | 393 | 50 | 1.15 (6H, t, J=7.0 Hz); 2.37 (3H, s); 2.90–2.92 (2H, dd); 3.32–3.35 (1H, m); 3.55–3.57 (1H, m); 3.69 (3H, s); 3.90–3.97 (3H, m); 4.29 (2H, t, J=6.9 Hz); 5.9 (1H, d, J=3.4 Hz); 6.1 (1H, d, J=3.4 Hz); 6.59 (2H, d, J=8.6 Hz); 7.05 (2H, d, J=8.5 Hz); 7.26–7.41 (5H, m). |

TABLE 14

| Ex. No. | Substituents on the pyrrole ring | | | | | Mol. Wt. (mp ° C.) | Yield (% w/w) | $^1$H NMR (300 MHz, δ CDCl$_3$) |
|---|---|---|---|---|---|---|---|---|
| | R$^1$ | R$^2$ | R$^3$ | R$^4$ | R' | | | |
| 77. | CH$_3$ | H | H | phenyl | CH$_3$ | 379 | 20 | — |
| 78. | CH$_3$ | H | H | phenyl | C$_3$H$_7$ | 408 | 22 | — |

Preparation 18

[2R, N(1S)]/[2S, N(1S)] 2-Ethoxy-N-(2-hydroxy-1-phenylethyl)-3-{4-[2-(5-methyl-2-phenylpyrrol-1-yl)ethoxy]phenyl}propanamide (Example no. 79)

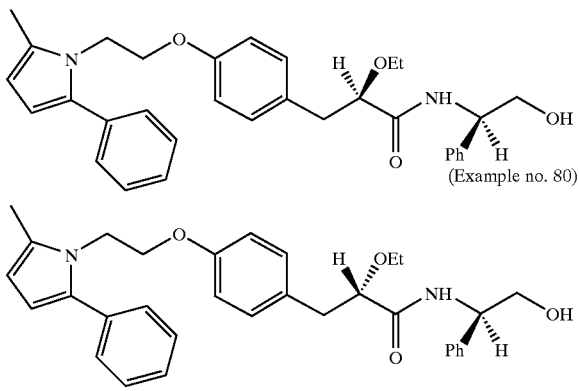

(Example no. 80)

To a well-stirred solution of (±) 2-ethoxy 3-{4-[2-(5-Methyl-2-(4-methylphenyl)pyrrol-1-yl)ethoxy]phenyl}-propanoic acid (1 g, 2 mmole) (prepared as in Example no. 76) in dry dichloromethane (10 mL), triethylamine (0.674 mL, 0.485 g, 4 mmole) was added at 0° C., followed by ethylchloroformate (0.311 g, 0.275 mL, 2 mmole) and stirred for 3.5 hr at same temperature. To this reaction, solution containing of (S)-phenyl glycinol (0.329 g, 2 mmole) in dichloromethane (5 mL) and triethylamine (0.674 mL, 0.485 g, 4 mmole) was added at 0° C. to 5° C. After stirring for 3 hrs at 0 to 10° C., the reaction was warmed to 20–25° C. and stirred for 16 hrs. The reaction mixture was diluted with dichloromethane (20 mL) and washed with H$_2$O (20 mL), brine (20 mL), dried over anhy. Na$_2$SO$_4$ and evaporated.

The residue was chromatographed over silica gel using a gradient of 10–50% of ethyl acetate: pet. ether as an eluent to afford firstly diastereomer assigned as [(2R)—N(1S)]-2-Ethoxy-3-{4-[2-(5-methyl-2-phenylpyrrol-1-yl)ethoxy]phenyl}-N-(2-hydroxy-1-phenylethyl)propanamide and [(2S)—N(1S)]-2-Ethoxy-3-{4-[2-(5-methyl-2-phenylpyrrol-1-yl)ethoxy]phenyl}-N-(2-hydroxy-1-phenylethyl) propanamide.

TABLE 15

| Ex. No. | Substituents on the pyrrole ring | | | | Mol. Wt. (mp° C.) | Yield (% w/w) | $^1$H NMR (300 MHz, δ, CDCl$_3$) |
|---|---|---|---|---|---|---|---|
| | R$^1$ | R$^2$ | R$^3$ | R$^4$ | | | |
| 79. | CH$_3$ | H | H | Phenyl | 407 | 50 | (2R) diastereomer 1.12 (3H, t, J=6.9 Hz); 2.30 (3H, s); 2.80–3.1 (2H, dd); 3.5 (2H, m); 3.91–3.95 (5H, m); 4.30 (2H, t, J=6.5 Hz); 5.00 (1H, m); 5.90 (1H, d, J=3.3 Hz); 6.10 (1H, d, J=3.3 Hz); 6.60 (2H, d, J=8.4 Hz); 6.9–7.1 (4H, m); 7.2–7.3 (3H, m); 7.32–7.4 (5H, m). |
| 80. | CH$_3$ | H | H | Phenyl | 407 | 50 | (2S) diastereomer 1.18 (3H, t, J=7.0 Hz); 2.39 (3H, s); 2.80–3.1 (2H, dd); 3.5–3.55 (2H, m); 3.84–3.97 (5H, m); 4.30 (2H, t, J=6.7 Hz); 5.00 (1H, m); 5.90 (1H, d, J=3.3 Hz); 6.10 (1H, d, J=3.3 Hz); 6.55 (2H, d, J=8.6 Hz); 6.9–7.1 (4H, d, J=8.5 Hz); 7.22–7.26 (3H, m) 7.41 (5H, m). |

Preparation 19

(R)-3-{4-[2-(5-methyl-2-phenylpyrrol-1-yl)ethoxy]phenyl}-2-ethoxypropanoic acid from the corresponding diastereomer (Example no. 81)

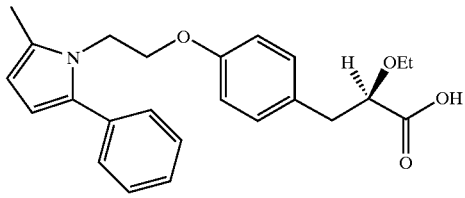

A solution of [(2R)—N(1S)]-2-Ethoxy-3-{4-[2-(5-methyl-2-phenylpyrrol-1-yl)ethoxy]phenyl}-N-(2-hydroxy-1-phenylethyl)propanamide (Example no. 79)(280 mg, 0.546 mmole) in a mixture of 1M. sulfuric acid (7 mL) and dioxane:$H_2O$:HCl (1:1,56 mL) was heated for at 100° C. for 24 hrs. The reaction mixture was cooled to 20° C. to 30° C. Product was extracted in ethyl acetate (2×30 mL). Combined extract was washed with $H_2O$ (3×30 mL), brine (30 mL) and dried over anhy. $Na_2SO_4$. Ethyl acetate was evaporated under reduced pressure to afford (252 mg) product.

Preparation 20

(S)-3-{4-[2-(5-methyl-2-phenylpyrrol-1-yl)ethoxy]phenyl}-2-ethoxypropanoic acid from the corresponding diastereomer

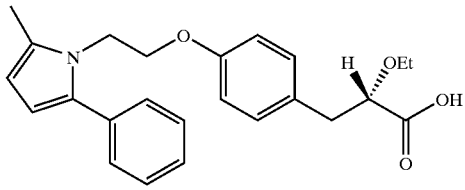

A solution of [(2S)—N(1S)]-2-Ethoxy-3-{4-[2-(5-methyl-2-phenylpyrrol-1-yl)ethoxy]phenyl}-N-(2-hydroxy-1-phenylethyl) propanamide (Example no. 80) was treated same as in preparation 19 to obtain the corresponding optically active acid. The is found identical to that obtained in (Example no. 48).

Preparation 21

3-{4-[2-(5-Methyl-2-phenylpyrrol-1-yl)ethoxy]phenyl}-2-ethoxypropanoic acid sodium salt (Example 100)

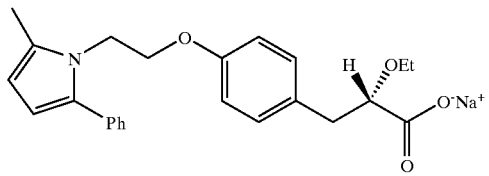

The acid prepared in example 49 (2.6 g) was dissolved in methanol (30 mL), sodium hydroxide (0.264 g) was added and stirred for 1 hour at 20° C. to 25° C. Afterwards, methanol was distilled at reduced pressure, to obtain an oily product. It was stirred with diisopropyl ether (50 mL) at 20–30° C. Solid sodium salt obtained was carefully filtered (2.3 g).

Preparation 22

3-{4-[2-(5-Methyl-2-phenylpyrrol-1-yl)ethoxy]phenyl}-2-ethoxy propanoic acid calcium salt (Example 101)

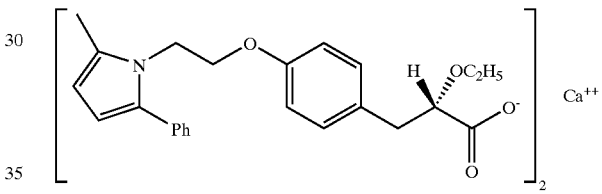

The sodium salt of example 95 (0.200 g), was dissolved in methanol (10 mL) and treated with calcium acetate (0.090 g) at 20° C.–25° C. Further, 50 mL of water was added when the calcium salt of the acid precipitates out. The precipitate was filtered, washed with water and then with di-isopropyl ether (2×20 mL) to afford the title compound.

Using the above procedure for Example 100 and Example 101 following salts are prepared using the appropriate acids/bases or according to the methods known in literature.

TABLE 16

(I)

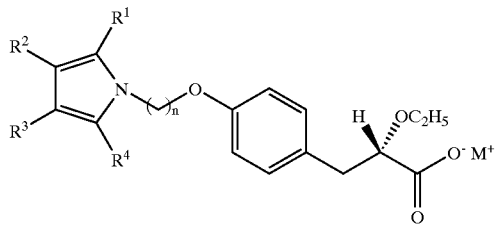

| Substituents on the pyrrole ring in (I) | | | | | M | |
|---|---|---|---|---|---|---|
| | | | | | $Na^+$ salts | $Ca^{++}$ salts |
| $R^1$ | $R^2$ | $R^3$ | $R^4$ | N | Example no. | Example no. |
| H | H | H | H | 2 | 82. | 83. |
| $CH_3$ | H | H | $CH_3$ | 2 | 84. | 85. |

TABLE 16-continued (I)

Structure: Pyrrole ring with substituents R¹, R², R³, R⁴ connected via N-(CH₂)n-O-phenyl-CH₂-CH(OC₂H₅)-C(=O)-O⁻ M⁺ (S-configuration)

| Substituents on the pyrrole ring in (I) | | | | | M | |
|---|---|---|---|---|---|---|
| | | | | | Na⁺ salts | Ca⁺⁺ salts |
| R¹ | R² | R³ | R⁴ | N | Example no. | Example no. |
| CH₃ | H | CH₃ | H | 2 | 86. | 87. |
| C₂H₅ | H | H | H | 2 | 88. | 89. |
| CHO | H | H | H | 2 | 90. | 91. |
| COCH₃ | H | H | H | 2 | 92. | 93. |
| CH₃ | H | H | CH₂CH₃ | 2 | 94. | 95. |
| CH₃ | H | H | (CH₂)₂CH₃ | 2 | 96. | 97. |
| CH₃ | H | H | (CH₂)₃CH₃ | 2 | 98. | 99. |
| CH₃ | H | H | phenyl | 2 | 100. | 101. |
| CH₃ | H | H | 4-methylphenyl | 2 | 102. | 103. |
| CH₃ | H | H | 3-methylphenyl | 2 | 104. | 105. |
| CH₃ | H | H | 4-methoxyphenyl | 2 | 106. | 107. |
| CH₃ | H | H | 4-bromophenyl | 2 | 108. | 109. |
| CH₃ | H | H | 4-fluorophenyl | 2 | 110. | 111. |
| CH₃ | H | phenyl | H | 2 | 112. | 113. |
| CH₃ | H | phenyl | phenyl | 2 | 114. | 115. |
| i-Pr | H | H | CH₃ | 2 | 116. | 117. |
| i-Pr | H | H | i-Pr | 2 | 118. | 119. |

TABLE 16-continued
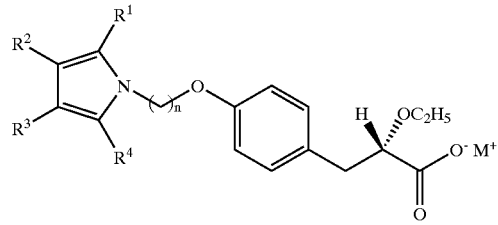
(I)
| Substituents on the pyrrole ring in (I) | | | | | M | |
|---|---|---|---|---|---|---|
| | | | | | Na+ salts | Ca++ salts |
| R¹ | R² | R³ | R⁴ | N | Example no. | Example no. |
| i-Pr | H | H | 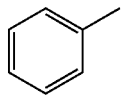 | 2 | 120. | 121. |
| i-Pr | 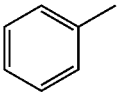 | H | i-Pr | 2 | 122. | 123. |
| i-Pr | H | H | 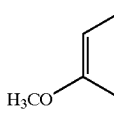 | 2 | 124. | 125. |
| i-Pr | H | H | 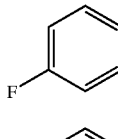 | 2 | 126. | 127. |
| i-Pr | H | 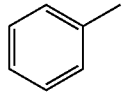 | 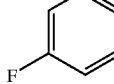 | 2 | 128. | 129. |
| i-Pr | 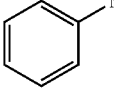 | H | 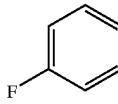 | 2 | 130. | 131. |
| i-Pr | 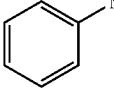 | 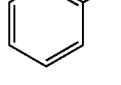 | 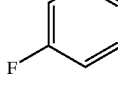 | 2 | 132. | 133. |
| i-Pr | 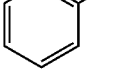 |  | 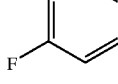 | 3 | 134. | 135. |
| 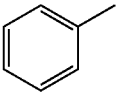 | —H | H | 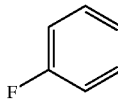 | 2 | 136. | 137. |
| 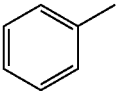 | —Coot | H | 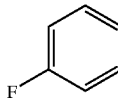 | 2 | 138. | 139. |
| SCH₃ | H | H | H | 2 | 140. | 141. |

TABLE 17

(I)

Structure: Pyrrole ring with R¹, R², R³, R⁴ substituents, connected via N-(CH₂)ₙ-O-phenyl-CH=C(OC₂H₅)-C(=O)-O⁻M⁺

| Substituents on the pyrrole ring in (I) | | | | | M | |
|---|---|---|---|---|---|---|
| | | | | | Na⁺ salts | Ca⁺⁺ salts |
| R¹ | R² | R³ | R⁴ | n | Example no. | Example no. |
| CH₃ | H | H | phenyl | 2 E-isomer | 142. | 143. |
| CH₃ | H | H | phenyl | 2 Z-isomer | 144. | 145. |

TABLE 18

(I)

Structure: Pyrrole ring with R¹, R², R³, R⁴ substituents, connected via N-(CH₂)ₙ-O-phenyl-CH₂-C*H(OR')-C(=O)-O⁻M⁺

| Ex. No. | Substituents on the pyrrole ring | | | | R' | M | Mol. Wt. (mp °C.) | Yield (% w/w) | ¹H NMR (300 MHz, δ CDCl₃) |
|---|---|---|---|---|---|---|---|---|---|
| | R¹ | R² | R³ | R⁴ | | | | | |
| 146. | CH₃ | H | H | 4-methylbenzyl (H₃C-C₆H₄-CH₂-) | CH₃ | Na | 401 | 100 | 2.37(3H, s); 2.93–3.03(2H, m); 3.37(3H, s); 3.90–3.96(3H, m); 4.28(2H, t, J=6.57Hz); 5.96(1H, d, J=3.33Hz); 6.10(1H, d, J=3.36Hz); 6.61(2H, d, J=8.58Hz); 7.08(2H, d, J=8.55Hz); 7.26–7.41(5H, m). |
| 147. | CH₃ | H | H | 4-methylbenzyl (H₃C-C₆H₄-CH₂-) | CH₃ | Ca | 796 | 44 | 0.83(3H, t, J=7.4Hz); 0.89(3H, t, J=7.4Hz); 1.53–1.63(4H, m); 2.37(3H, s); 2.91(2H, d, J=5.54Hz); 3.20–3.48(2H, m); 3.92(6H, t, J=6.59Hz); 4.06(2H, t, J=6.67Hz); 4.28(2H, t, J=6.61Hz); 5.97(1H, d, J=3.33Hz); 6.11(1H, d, J=3.40Hz); 6.59(2H, d, J=8.64Hz); 7.07(2H, d, J=8.63Hz); 7.25–7.40(5H, m). |

TABLE 18-continued (I)

Structure (I): pyrrole ring with substituents R¹, R², R³, R⁴ on positions, N-linked via (CH₂)ₙ-O to phenyl ring with -CH₂-CH(OR')-C(=O)-O⁻M⁺ group.

| Ex. No. | Substituents on the pyrrole ring | | | | R' | M | Mol. Wt. (mp ° C.) | Yield (% w/w) | ¹H NMR (300 MHz, δ CDCl₃) |
|---|---|---|---|---|---|---|---|---|---|
| | R¹ | R² | R³ | R⁴ | | | | | |
| 148. | CH₃ | H | H | 4-(H₃C-C₆H₄)- | C₃H₇ | Ca | 852 | 42 | 0.77(3H, t, J=7.41Hz); 1.47–1.49(4H, m); 2.34(3H, s); 2.60–2.63(2H, s) 3.07–3.38(2H, m); 3.90(2H, t, J=6.01Hz); 4.31(2H, t, J=6.61Hz) 5.87(1H, d, J=3.36Hz); 5.99(1H, d, J=3.39Hz); 6.58(2H, d, J=8.52Hz); 7.10(2H, d, J=8.52Hz); 7.29–7.40(5H, m). |

The compounds of the present invention lowered triglyceride, total cholesterol, LDL, VLDL and increased HDL and lowered serum glucose levels. This was demonstrated by in vivo animal experiments.

A) Demonstration of in vitro Efficacy of Compounds:
  i) Determination of hPPARα Activity:

A chimeric expression vectors constructs containing the translational sequences of PPAR □ and amino acid sequences of DNA binding domains were fused and inserted into PGL3 basic vector. The expression and sequence were verified through immunobloting and sequence analysis (ABI DNA analyzer). These chimeric vectors containing ligand binding as well as DNA binding domain and a reporter plasmid containing the luciferase gene driven by SV40 promoter were transfected into CV-1 cell using the transfectin (Gibco BRL, USA). A control reporter plasmid was also transfected to monitor the transfection efficiency. After 48 hrs of transfection, The test compound was added in various concentration and incubated overnight. The luciferase activity was analyzed as a function of compound binding/activation capacity of PPARA, by luciferase assay system (promega, USA).

ii) Determination of hPPARγ Activity:

A chimeric expression vectors constructs containing the translational sequences of PPARγ and amino acid sequences of DNA binding domains were fused and inserted into PGL3 basic vector. The expression and sequence were verified through immunobloting and sequence analysis (ABI DNA analyzer). These chimeric vectors containing ligand binding as well as DNA binding domain and a reporter plasmid containing the luciferase gene driven by SV40 promoter were transfected into CV-1 cell using the transfectin (Gibco BRL, USA). A control reporter plasmid was also transfected to monitor the transfection efficiency. After 48 hrs of transfection, The test compound was added in various concentration and incubated overnight. The luciferase activity was analyzed as a function of compound binding/activation capacity of PPARγ, by luciferase assay system (promega, USA).

B) Demonstration of in vivo Efficacy of Compounds:
  i) Plasma Triglyceride and Total Cholesterol Lowering Activity in Swiss Albino Mice and Guinea Pigs:

Male Swiss albino mice (SAM) and male Guinea pigs were bred in Zydus animal house. All these animals were maintained under 12 hour light and dark cycle at 25±1° C. Animals were given standard laboratory chow (NIN, Hyderabad, India) and water ad libitum. SAM of 20–30 g body weight range and Guinea pigs of 600–750 g body weight range were used (Atherosclerosis, 1988, 70:107–114).

The test compounds were administered orally to Swiss albino mice at 0.001 to 50 mg/kg/day dose for 6 days. Control mice were treated with vehicle (0.25% of Carboxymethylcellulose; dose 10 ml/kg).

The test compounds were administered orally to Guinea pigs at 0.1 to 30 mg/kg/day dose for 6 days. The compound was administered after suspending it 0.25% CMC or dissolving it in water, when compound is water-soluble. Control mice were treated with vehicle (0.25% of Carboxymethylcellulose; dose 10 ml/kg).

The blood samples were collected on $0^{th}$ day and in fed state 1 hour after drug administration on $6^{th}$ day of the treatment. The blood was collected in non heparinised capillary and the serum was analyzed for triglyceride and total cholesterol (Wieland, O. Methods of Enzymatic analysis. Bergermeyer, H., O., Ed., 1963. 211–214; Trinder, P. Ann. Cli. Biochem. 1969. 6: 24–27). Measurement of plasma triglyceride and total cholesterol was done using commercial kits (Zydus-Cadila, Pathline, Ahmedabad, India).

Formula for Calculation:

Percentage reduction in triglycerides/total cholesterol were calculated according to the formula:

$$\text{Percentage reduction}(\%) = [1 - \{(TT/T_0)/(TC/OC)\}]TT \times 100$$

OC=Zero day control group value
OT=Zero day treated group value

TC=Test day control group
TT=Test day treated group ii) Cholesterol Lowering Activity in Hypercholesterolemic Rat Models Male Sprague Dawley rats stock bred in Zydus animal house were maintained under 12 hour light and dark cycle at 25±1° C. Rats of 100–150 g body weight range were used for the experiment. Animals were made hypercholesterolemic by feeding 1% cholesterol and 0.5% sodium cholate mixed with standard laboratory chow (NIN, Hyderabad, India) and water ad libitum for 5 days. The animals were maintained on the same diet throughout the experiment [Petit D., Bonnefis M. T., Rey C and Infante R., Effects of ciprofibrate on liver lipids and lipoprotein synthesis in normal and hyperlipidemic rats, *Atherosclerosis*, 74, 215–225(1988)].

The test compounds were administered orally at a dose 0.03 to 50 mg/kg/day for 4 days, after suspending it in 0.25% CMC or dissolving it in water when compound is water-soluble. Control group was treated with vehicle alone (0.25% of Carboxymethylcellulose; dose 10 ml/kg).

The blood samples were collected in fed state on $0^{th}$ and 1 hour after drug administration on $6^{th}$ day of the treatment. The blood was collected from the retro-orbital sinus through non-heparinised capillary and the serum samples were analyzed for triglyceride and total cholesterol using commercial kits (Zydus-Cadila, Pathline, Ahmedabad, India). LDL and HDL by commercial kits (Point Scientific, USA). LDL and VLDL cholesterol were calculated from the data obtained for total cholesterol, HDL and triglyceride.

The reduction in VLDL cholesterol is calculated according to the formula.

VLDL cholesterol in mg/dl=Total cholesterol−HDL cholesterol−LDL cholesterol iii) Plasma Glucose Lowering Activity in db/db Mice Models Homozygous animal $C_{57}BL/KsJ$-db/db mice are obese, hyperglycemic, hyperinsulinemic and insulin resistant (J. Clin. Invest., 85, 962–967, 1990), whereas heterozygous are lean and normoglycemic. The homozygous animals very closely mimic the human type II diabetes when blood sugar levels are not sufficiently controlled. Since this type of model resembles human type II diabetes mellitus, the compounds of the invention were tested for their antidiabetic activity in this model.

The compounds of the present invention showed plasma glucose and triglycerides lowering activities. Male $C_{57}$ BL/KsJ-db/db mice of 8 to 14 weeks age, having body weight range of 40 to 60 grams, procured from the Jackson Laboratory, USA, were used in the experiment.

Test compounds were suspended on 0.25% carboxymethyl cellulose or dissolved in water when the compound is water soluble and administered to test group containing 6 animals at a dose of 0.001 mg to 50 mg/kg through oral gavage daily for 6 days. The control group received vehicle (dose 10 ml/kg). On the $6^h$ day, one hour after the drug dosing, blood was collected from retro-orbital sinus and the plasma was analyzed for glucose and triglycerides were measured using commercial kits (Zydus-Cadila, Pathline, Ahmedabad, India). The plasma glucose and triglyceride lowering activities of the test compound was calculated according of the formula:

$$\text{Plasma glucose lowering activity } (\%) = 1 - \left(\frac{DT/DC}{TC/ZC}\right) \times 100$$

ZC=Zero day control group value
TC=Test day control group
DC=Zero day treated group value
DT=Test day treated group iv) Plasma Triglyceride/Cholesterol/Body Weight Lowering Effect in Golden Syrian Hamsters:

Male Golden Syrian hamsters were fed with a standard diet mixed with 1% cholesterol and 0.5% sodium cholate for 5 days. On $6^{th}$ day test compounds in dose ranging from 1 mg to 10 mg/kg/day were administered as CMC suspension, and the same diet was maintained for the next 15 days. On the $15^{th}$ day the blood samples were collected in fed state, one hour after drug administration from retro-orbital sinus and the serum was analyzed for triglyceride and cholesterol using commercial kits (Zydus-Cadila, Pathline, Ahmedabad, India). The body weight was measured with respect to untreated group on hypercholesteremic diet. The compounds of the present invention reduced triglycerides, cholesterol and body weight in this animal model.

No adverse effects were observed for any of the mentioned compounds of invention. The compounds of the present invention showed good plasma lowering and lipid and cholesterol lowering activity in the experimental animals used. These compounds are useful for the testing/prophylaxis of diseases caused by hyperlipidemia, hypercholesterolemia, hyperinsulinemia, hyperglycemia such as NIDDM, cardiovascular diseases, stroke, hypertension, obesity since such diseases are interlinked to each other.

We claim:

1. A compound of formula (I):

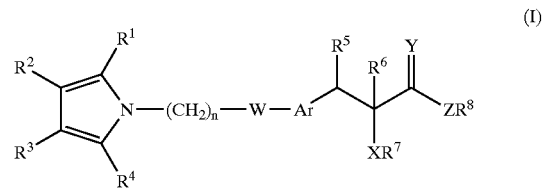

(I)

their tautomeric forms, their stereoisomers, their pharmaceutically acceptable salts, their pharmaceutically acceptable solvates, wherein one or more groups $R^1$, $R^2$, $R^3$, $R^4$ may be same or different and represent hydrogen, halogen, perhaloalkyl, hydroxy, thio, amino, nitro, cyano, formyl, amidino, guanidino, substituted or unsubstituted groups selected from linear or branched $(C_1-C_{12})$alkyl, linear or branched $(C_2-C_{12})$alkenyl, $(C_3-C_8)$cycloalkyl, $(C_3-C_8)$ cycloalkenyl, bicycloalkyl, bicycloalkenyl, $(C_1-C_{12})$alkoxy, cyclo$(C_3-C_8)$alkoxy, aryl, aryloxy, aralkyl, ar$(C_1-C_{12})$ alkoxy, heterocyclyl, heteroaryl, heterocyclyl$(C_1-C_{12})$alkyl, heteroar$(C_1-C_{12})$alkyl, heteroaryloxy, heteroar$(C_1-C_{12})$ alkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, aminoalkyl, monoalkylaminoalkyl, dialkylaminoalkyl, alkoxyalkyl, aryloxyalkyl, aralkoxyalkyl, $(C_1-C_{12})$alkylthio, thio $(C_1-C_{12})$alkyl, arylthio, $(C_1-C_{12})$alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and derivatives of carboxylic acids selected from $CONH_2$, alkylaminocarbonyl, dialkylaminocarbonyl, arylaminocarbonyl; aralkylaminocarbonyl; heteroarylaminocarbonyl and heteroaralkylamino carbonyl groups; heterocyclylaminocarbonyl groups; sulfonic acid and its derivatives selected from $SO_2NH_2$, $SO_2NHMe$, $SO_2NMe_2$, $SO_2NHCF_3$, $SO_2NHCO$ ($C_1$–$C_6$)alkyl, $SO_2NHCO$aryl groups, phosphonic acid and its derivatives selected from $P(O)(OH)_2$, $P(O)(O\ C_1$–$C_6$ alkyl)$_2$, $P(O)(O$ aryl)$_2$, $P(O)(OH)$ ($O\ C_1$–$C_6$ alkyl) groups; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, ($C_1$–$C_{12}$)alkyl or aryl; Ar represents a substituted or unsubstituted divalent single or fused aromatic, heteroaromatic or heterocyclic group; $R^5$ and $R^6$ represent both hydrogen or together represent a bond; $R^5$ and $R^6$ may also represent a hydroxy, ($C_1$–$C_{12}$)alkyl, ($C_1$–$C_{12}$)alkoxy, halogen, acyl, substituted or unsubstituted aralkyl group; X represents O or S; $R^7$ represents hydrogen, perfluoro ($C_1$–$C_{12}$)alkyl, substituted or unsubstituted groups selected from ($C_1$–$C_{12}$)alkyl, cyclo($C_1$–$C_{12}$)alkyl, aryl, ar($C_1$–$C_{12}$) alkyl, heteroaryl, heteroar($C_1$–$C_{12}$)alkyl, heterocyclyl, alkoxyalkyl, aryloxyalkyl, alkoxycarbonyl, aryloxycarbonyl. cycloalkyloxycarbonyl, alkylaminocarbonyl, arylaminocarbonyl, acyl groups; Y represents O or S; Z represents oxygen, sulfur or $NR^{10}$, where $R^{10}$ represents hydrogen or substituted or unsubstituted groups selected from ($C_1$–$C_{12}$)alkyl, aryl, ar($C_1$–$C_{12}$)alkyl, hydroxy ($C_1$–$C_{12}$)alkyl. ammo($C_1$–$C_{12}$)alkyl, heteroaryl, heteroar ($C_1$–$C_{12}$)alkyl groups; $R^8$ represents hydrogen, substituted or unsubstituted groups selected from ($C_1$–$C_{12}$)alkyl, aryl, ar($C_1$–$C_{12}$)alkyl, heteroaryl, heteroar($C_1$–$C_{12}$)alkyl, heterocyclyl, heterocyclylalkyl, hydroxyalkyl, alkoxyalkyl, alkylaminoalkyl groups; $R^{10}$ and $R^8$ together may form a 5 or 6 membered substituted or unsubstituted cyclic ring structure containing carbon atoms or containing one or more heteroatoms selected from O, N and S.

2. A compound according to claim 1, wherein the substituents on the groups $R^1$, $R^2$, $R^3$ and $R^4$ are selected from halogen, hydroxy, formyl, nitro, oxo, thio, or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkylamino, alkoxyalkyl, alkylthio, thioalkyl groups, thioalkyl, alkylsulfenyl, alkylsulfonyl, carboxylic acid or its derivatives, or sulfonic acid or its derivatives or phosphonic acid or its derivatives.

3. A compound according to claim 1, wherein the group Ar represents a phenyl ring.

4. A compound according to claim 1, wherein Ar represents substituted or unsubstituted groups selected from divalent groups selected from phenylene, naphthylene. indenyl, dihydrobenzofiiryl, benzopyranyl, dihydrobenzopyranyl, indolyl, indolinyl, pyridyl, quinolinyl, a.zaindolyl, azaindolinyl, benzofuryl, benzothiazolyl or beuzoxazolyl groups.

5. A compound according to claim 1, wherein the substituents on the group represented by Ar represents substituted or unsubstituted linear or branched alkyl, alkoxy, thioalkyl, halogen, haloalkyl, haloalkoxy, acyl, amino, acylamino, thio or carboxylic or sulfonic acids and their derivatives, phosphonic acid and their derivatives.

6. A compound according to claim 4, wherein the substituents on the group represented by

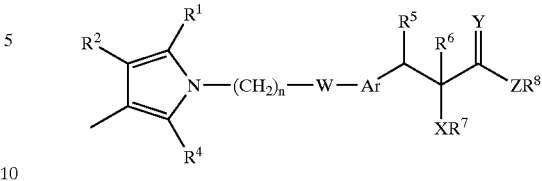

Ar represents substituted or unsubstituted linear or branched alkyl, alkoxy, thioalkyl halogen, halo alkyl, haloalkoxy, acyl, amino, acylamino, thio or carboxylic or sulfonic acids and their derivatives, phosphonic acid and their derivatives.

7. A compound according to claim 1, wherein the pharmaceutically acceptable salt is a Li, Na, Ca, Mg, lysine, arginine, guanidine and its derivatives, tromethamine, diethanolamine, choline, ammonium, substituted ammonium salts, or a aluminium salts.

8. A pharmaceutical composition which comprises a compound of formula (1), as defined in the claim 1 and a pharmaceutically acceptable carrier, diluent, excipients or solvate.

9. A pharmaceutical composition according to claim 8, in the form of a tablet, capsule, powder, syrup, solution or suspension.

10. A pharmaceutical composition which comprises, a compound according to claim 7, as an active ingredient and a pharmaceutically acceptable carrier, diluent, excipients or solvate.

11. A pharmaceutical composition which comprises, a compound according to claim 7, in the form of a tablet, capsule, powder, syrup, solution or suspension.

12. A method of treating diseases caused by hyperlipidaemia, hypercholesteremia, hyperglycemia, obesity, impaired glucose intolerance, leptin resistance, insulin resistance, diabetic complications, comprising administering an effective, non-toxic amount of compound of formula (1) as defined in claim 1 to a patient in need thereof.

13. The method according to claim 12, wherein the complication is type 2 diabetes, impaired glucose tolerance, dyslipidaemia, hypertension. obesity, atherosclerosis, hyperlipidaemia, coronary artery disease, cardiovascular disorders, renal diseases, microalbuminuria, glomerulonephritis, glomerulosclerosis, nephrotic syndrome, hypertensive nephrosclerosis, diabetic retinopathy, diabetic nephropathy, endothelial cell dysfunction, psoriasis, polycystic ovarian syndrome, dementia, end-stage renal disease, osteoporosis, inflammatory bowel diseases, myotonic dystrophy, pancreatitis, arteriosclerosis, xanthoma or cancer.

14. A compound according to claim 1 which is selected from:

(±) Ethyl 3-{4-[2-(pyrrol-1-yl)ethoxy]phenyl}-2-ethoxypropanoate;

(+) Ethyl 3-{4-[2-(pyrrol-1-yl)ethoxy]phenyl}-2-ethoxypropanoate;

(−) Ethyl 3-{4-[2-(pyrrol-1-yl)ethoxy]phenyl}-2-ethoxypropanoate;

(±) Ethyl 3-{4-[2-(2,5-dimethylpyrrol-1-yl)ethoxy] phenyl}-2-ethoxypropanoate;

(+) Ethyl 3-{4-[2-(2,5-dimethylpyrrol-1-yl) ethoxyjphenyl}-2-ethoxypropanoate;

(−) Ethyl 3-{4-[2-(2,5-dimethylpyrrol-1-yl)ethoxy] phenyl}-2-ethoxypropanoate;

(±) Ethyl 3-{4-[2-(2,4-dimethylpyrrol-1-yl)ethoxy]phenyl}-2-ethoxypropanoate;

(+) Ethyl 3-{4-[2-(2,4-dimethylpyrrol-1-yl)ethoxy]phenyl}-2-ethoxypropanoate;

(−) Ethyl 3-{4-[2-(2,4-dimethylpyrrol-1-yl)ethoxy]phenyl)-2-ethoxypropanoate;

(±) Ethyl 3-{4-[2-(2-formylpyrrol-1-yl)ethoxy]phenyl}-2-ethoxypropanoate (+) Ethyl 3-{4-[2-(2-formylpyrrol-1-yl)ethoxy]phenyl}-2-ethoxypropanoate;

(−) Ethyl 3-{4-[2-(2-formylpyrrol-1-yl)ethoxy]phenyl}-2-ethoxypropanoate;

(±) Ethyl 3-{4-[2-(2-acetylpyrrol-1-yl)ethoxy]phenyl}-2-ethoxypropanoate;

(+) Ethyl 3-{4-[2-(2-acetylpyrrol-1-yl)ethoxy]phenyl}-2-ethoxypropanoate;

(−) Ethyl 3-{4-[2-(2-acetylpyrrol-1-yl)ethoxy]phenyl}-2-ethoxypropanoate;

(±) Ethyl 3-{4-[2-(2-ethylpyrrol-1-yl)ethoxy]phenyl}-2-ethoxypropanoate;

(+) Ethyl 3-{4-[2-(2-ethylpyrrol-1-yl)ethoxy]phenyl}-2-ethoxypropanoate;

(−) Ethyl 3-{4-[2-(2-ethylpyrrol-1-yl)ethoxy]phenyl}-2-ethoxypropanoate;

(±) Ethyl 3-{4-[2-(2-ethyl-5-methylpyrrol-1-yl)ethoxy]phenyl)-2-ethoxypropanoate;

(+) Ethyl 3-{4-[2-(2-ethyl-5-methylpyrrol-1-yl)ethoxy]phenyl}-2-ethoxypropanoate;

(−) Ethyl 3-{4-[2-(2-ethyl-5-methylpyrrol-1-yl)ethoxy]phenyl}-2-ethoxypropanoate;

(±) Ethyl 3-{4-(2-(5-methyl-2-propylpyrrol-1-yl)ethoxy]phenyl)-2-ethoxypropanoate;

(+) Ethyl 3-(4-[2-(5-methyl-2-propylpyrrol-1-yl)ethoxy]phenyl)-2-ethoxypropanoate;

(−) Ethyl 3-(442-(5-methyl-2-propylpyrrol-1-yl)ethoxy]phenyl}-2-ethoxypropanoate;

(±) Ethyl 3-{4-[2-(5-methyl-2-n-butylpyrrol-1-yl)ethoxy]phenyl)-2-ethoxypropanoate;

(+) Ethyl 3-{4-[2-(5-methyl-2-n-butylpyrrol-1-yl)ethoxy]phenyl}-2-ethoxypropanoate;

(−) Ethyl 3-{4-[2-(5-methyl-2-n-butylpyrrol. 1-yl)ethoxy]phenyl}-2-ethoxypropanoate;

(±) Ethyl 3-(4-f 2-(5-methyl-2-phenylpyrrol-1-yl)ethoxy]phenyl)-2-ethoxypropanoate;

(+) Ethyl 3-{4-[2-(5-methyl-2-phenylpyrrol-1-yl)ethoxy]phenyl}-2-ethoxypropanoate;

(−) Ethyl 3-{4-[2-(5-methyl-2-phenylpyrrol-1-yl)ethoxy]phenyl)-2-ethoxypropanoate;

(±) Ethyl 3-{4-[2-(5-methyl-3-phenylpyrrol-1-yl)ethoxy]phenyl}-2-ethoxypropanoate;

(+) Ethyl 3-{4-[2-(5-methyl-3-phenylpyrrol-1-yl)ethoxy]phenyl)-2-ethoxypropanoate;

(−) Ethyl 3-{4-(2-(5-methyl-3-phenylpyrrol-1-yl)ethoxy]phenyl)-2-ethoxypropanoate;

(±) Ethyl 3-{4-[2-(5-methyl-2-phenylpyrrol-1-yl)ethoxy]phenyl)-2-methoxypropanoate;

(+) Ethyl 3-{4-[2-(5-methyl-2-phenylpyrrol-1-yl)ethoxy]phenyl)-2-methoxypropanoate;

(−) Ethyl 3-{4-[2-(5-methyl-2-phenylpyrrol-1-yl)ethoxy]phenyl)-2-methoxypropanoate;

(±) Methyl 3-{4-[2-(5-methyl-2-phenylpyrrol-1-yl)ethoxy]phenyl)-2-methoxypropanoate;

(+) Methyl 3-{4-[2-(5-methyl-2-phenylpyrrol-1-yl)ethoxy]phenyl)-2-methoxypropanoate;

(−) Methyl 3-{4-[2-(5-methyl-2-phenylpyrrol-1-yl)ethoxy]phenyl)-2-methoxypropanoate;

(±) Ethyl 3-{4-{2-(5-methyl-2-phenylpyrrol-1-yl)ethoxy]phenyl)-2-propoxypropanoate;

(+) Ethyl 3-{4-[2-(5-methyl-2-phenylpyrrol-1-yl)ethoxy]phenyl)-2-propoxypropanoate;

(−) Ethyl 3-(4-(2-(5-methyl-2-phenyl)pyrrol-1-yl)ethoxy]phenyl}-2-propoxypropanoate;

(±) Propyl 3-{4-(2-(S-methyl-2-phenylpyrrol-1-yl)ethoxy]phenyl)-2-propoxypropanoate;

(+) Propyl 3-{4-[2-(5-methyl-2-phenylpyrrol-1-yl)ethoxy]phenyl}-2-propoxypropanoate;

(−) Propyl 3-{4-[2-(5-methyl-2-phenylpyrrol-1-yl)ethoxy]phenyl}-2-propoxypropanoate;

(±) Ethyl 3-{4-[2-(5-methyl-2-(4-methylphenyl)pyrrol-1-yl)ethoxy]phenyl)-2-ethoxypropanoate;

(+) Ethyl 3-{4-(2-(5-methyl-2-(4-methylphenyl)pyrrol-1-yl)ethoxy]phenyl)-2-ethoxypropanoate;

(−) Ethyl 3-{4-[2-(5-methyl-2-(4-methylphenyl)pyrrol-1-yl)ethoxy]phenyl)-2-ethoxypropanoate;

(±) Ethyl 3-{4-[2-(5-methyl-2-(3-methylphenyl)pyrrol-1-yl)ethoxy]phenyl).2-ethoxypropanoate;

(+) Ethyl 3-(4-[2-(5-methyl-2-(3-methylphenyl)pyrrol-1-yl)ethoxy]phenyl)-2-ethoxypropanoate;

(−) Ethyl 3-(4-[2-(5-methyl-2-(3-methylphenyl)pyrrol-1-yl)ethoxy]phenyl}-2-ethoxypropanoate;

(±) Ethyl 3-(4-[2-(5-methyl-2-(2-methylphenyl)pyrrol-1-yl)ethoxy]phenyl)-2-ethoxypropanoate, (+) Ethyl 3-(4-[2-(5-methyl-2-(2-methylphenyl)pyrrol-1-yl)ethoxy]phenyl)-2-ethoxypropanoate;

(−) Ethyl 3-{4-[2.{5-methyl-2-(2-methylphenyl)pyrrol-1-yl)ethoxy]phenyl}-2-ethoxypropanoate;

(±) Ethyl 3-{4-{2-(5-methyl-2-(4-methoxyphenyl)pyrrol-1-yl)ethoxy]phenyl}-2-ethoxypropanoate;

(±) Ethyl 3-(4-(2-(5-methyl-2-(4-methoxyphenyl)pyrrol-1-yl)ethoxy]phenyl}-2-ethoxypropanoate, (−) Ethyl 3-{442-(5-methyl-2-(4-methoxyphenyl)pyrrol-1-yl)ethoxy]phenyl)-2-ethoxypropanoate;

(±) Ethyl 3-{4-[2-(5-methyl-2-(4-bromophenyl)pyrrol-1-yl)ethoxy]phenyl}-2-ethoxypropanoate;

(+) Ethyl 3-{4-[2-(5-methyl-2-(4-bromophenyl)pyrrol-1-yl)ethoxy]phenyl}-2-ethoxypropanoate;

(−) Ethyl 3-(4-[2-(5-methyl-2-(4-bromophenyl)pyrrol-1-yl)ethoxy]phenyl)-2-ethoxypropanoate;

(±) Ethyl 3-(4-[2-(5-methyl-2-(4-fluorophenyl)pyrrol-1-yl)ethoxy]phenyl)-2-ethoxypropanoate;

(+) Ethyl 3-{4-{2-(5-methyl-2-(4-fluorophenyl)pyrrol-1-yl)ethoxy]phenyl)-2-ethoxypropanoate;

(−) Ethyl 3-{4-[2-(5-methyl-2-(4-fluorophenyl)pyrrol-1-yl)ethoxy]phenyl}-2-ethoxypropanoate;

(±) Ethyl 3-{4-[2-(5-methyl-2-(4-chlorophenyl)pyrrol-1-yl)ethoxy]phenyl)-2-ethoxypropanoate;

(+) Ethyl 3-{4-[2-(5-methyl-2-(4-chlorophenyl)pyrrol-1-yl)ethoxy]phenyl)-2-ethoxypropanoate;

(−) Ethyl 3-{4-[2<5-methyl-2-(4-chlorophenyl)pyrrol-1-yl)ethoxy]phenyl)-2-ethoxypropanoate;

(±) Ethyl 3-(4-(2-(4-methyl-2-phenylpyrrol-1-yl)ethoxy]phenyl}-2-ethoxypropanoate;

(30) Ethyl 3-{4-[2-(4-methyl-2-phenylpyrrol-1-yl)ethoxy]phenyl}-2-ethoxypropanoate;

(−) Ethyl 3-(4-(2-(4-methyl-2-phenylpyrrol-1-yl)ethoxy)phenyl}-2-ethoxypropanoate;

(±) Ethyl 3-(4-[2-(5-methyl-2,3-diphenylpyrrol-1-yl)ethoxy]phenyl)-2-ethoxypropanoate;

(30) Ethyl 3-{4-(2.(5-methyl-2,3-diphenylpyrrol-1-yl)ethoxy]phenyl}-2-ethoxypropanoate;

(−) Ethyl 3-{4-[2-(5-methyl-2,3-diphenylpyrrol-1-yl)ethoxy]phenyl)-2-ethoxypropanoate;

(±) Ethyl 3-(4-(2-(2-isopropyl-5-methylpyrrol-1-yl)ethoxy]phenyl)-2-ethoxypropanoate;

(30) Ethyl 3-(4-[2-(2-isopropyl-5-methylpyrrol-1-yl)ethoxy]phenyl)-2-ethoxypropanoate;

(−) Ethyl 3-{4-[2-(2-isopropyl-5-methylpyrrol-1-yl)ethoxy]phenyl)-2-ethoxypropanoate;

(±) Ethyl 3-{4-[2-(2,5-diisopropylpyrrol-1-yl)ethoxy]phenyl)-2-ethoxypropanoate;

(+) Ethyl 3-44-(2-(2,5-diisopropylpyrrol-1-yl)ethoxy]phenyl)-2-ethoxypropanoate;

(−) Ethyl 3-{4-[2-(2,5-diisopropylpyrrol-1-yl)ethoxy]phenyl}-2-ethoxypropanoate;

(±) Ethyl 3-{4-[2-(5-isopropyl-2-phenylpyrrol-1-yl)ethoxy]phenyl)-2-ethoxypropanoate;

(+) Ethyl 3-{4-(2-(5-isopropyl-2-phenylpyrrol-1-yl)ethoxy]phenyl}-2-ethoxypropanoate;

(−) Ethyl 3-{4-[2-(5-isopropyl-2-phenylpyrrol-1-yl)ethoxy]phenyl}-2-ethoxypropanoate;

(±) Ethyl 3-{4-[2-(2,5-diisopropyl-3-phenylpyrrol-1-yl)ethoxy]phenyl}-2-ethoxypropanoate;

(+) Ethyl 3-{4-[2-(2,5-diisopropyl-3-phenylpyrrol-1-yl)ethoxy]phenyl}-2-ethoxypropanoate;

(−) Ethyl 3-(4-[2-(2,5-diisopropyl-3-phenylpyrrol-1-yl)ethoxy]phenyl}-2-ethoxypropanoate;

(±) Ethyl 3-(4-{2-f5-isopropyl-2-(4-methoxyphenyl)pyrrol-1-yl]ethoxy)phenyl)-2-ethoxypropanoate;

(+) Ethyl 3-(4-{2-[5-isopropyl-2-(4-methoxyphenyl)pyrrol-1-yl]ethoxy) phenyl)-2-ethoxypropanoate;

(−) Ethyl 3-(4-(2-[5-isopropyl-2-(4-methoxyphenyl)pyrrol-1-yl]ethoxy}phenyl)-2-ethoxypropanoate;

(±) Ethyl 3-(4-{2-(2-(4-fluorophenyl)-5-isopropylpyrrol-1-yl]ethoxy) phenyl)-2-ethoxypropanoate;

(+) Ethyl 3-(4-{2-[2-(4-fluorophenyl)-5-isopropylpyrrol-1-yl]ethoxy) phenyl)-2-ethoxypropanoate;

(−) Ethyl 3-(4-(2-[2-(4-fluorophenyl)-5-isopropylpyrrol-1-yl]-ethoxy}phenyl)-2-ethoxypropanoate;

(±) Ethyl 3-(4~{2~j~2-(4-fluorophenyl)-5-isopropyl-3-phenylpyrrol-1-yl]ethoxy}phenyl)-2-ethoxy propanoate;

(+) Ethyl 3-(4-(2-[2-(4-fluorophenyl)-5-isopropyl-3-phenylpyrrol-1-yl]ethoxy}phenyl)-2-ethoxy propanoate;

(−) Ethyl 3-(4-{2-[2-(4-fluorophenyl)-5-isopropyl-3-phenylpyrrol-1-yl]ethoxy}phenyl)-2-ethoxy propanoate;

(±) Ethyl 3-(4-{2-[2-(4-fluorophenyl)-5-isopropyl-4-phenylcarbamoylpyrrol-1-yl]ethoxy}phenyl)-2- ethoxypropanoate;

(+) Ethyl 3-(4-(2-[2-(4-fluorophenyl)-5 isopropyl-4-phenylcarbamoylpyrrol-1-yl]ethoxy}phenyl)-2- ethoxypropanoate;

(−) Ethyl 1-yl]ethoxy)phenyl)-2- ethoxypropanoate;

(±) Ethyl 3-(4-{2-(2-(4-fluorophenyl)-5-isopropyl-3-phenyl-4- phenylcarbamoylpyrrol-1-yl]ethoxy)phenyl)-2-ethoxypropanoate;

(+) Ethyl 3-(4-{2-f2-(4-fluorophenyl)-5-isopropyl-3-phenyl-4- phenylcarbamoylpyrrol -1-yl]ethoxy}phenyl)-2-ethoxypropanoate;

(−) Ethyl 3-(4-{2-[2-(4-fluorophenyl)-3-isopropyl-3-phenyl-4-phenylcarbamoylpyrrol-1-yl]ethoxy)phenyl)-2-ethoxypropanoate;

(±) Ethyl 3-(4-(3-1-yl]propoxy}phenyl)-2-ethoxypropanoate;

(+) Ethyl 3-(4-(3-(2-(4-fluorophenyl)-5-isopropyl-3-phenyl-4-phenylcarbamoylpyrrol-1-yl]propoxy}phenyl)-2-ethoxypropanoate;

(−) Ethyl 3-(4-(3-(2-(4-fluorophenyl)-5-isopropyl-3-phenyl-4 phenylcarbamoylpyrrol-1-yl]propoxy}phenyl)-2- ethoxypropanoate;

(±) Ethyl 3-(4-{2-[2-(4-fluorophenyl)-5-phenylpyrrol-1-yl]ethoxy}phenyl)-2-ethoxypropanoate;

(+) Ethyl 3-(4-{2-[2-(4-fluorophenyl)-5-phenylpyrrol-1-yl]ethoxy}phenyl)-2-ethoxypropanoate;

(−) Ethyl 3-(4-{2-[2-(4-fluorophenyl)-5-phenylpyrrol-1-yl]ethoxy}phenyl)-2-ethoxypropanoate; (±) Ethyl 3-(4-[2-[3-carboxy-5-phenyl-2(4-fluorophenyl)pyrrol-1-yl)ethoxy]phenyl-2-ethoxy propanoate;

(+) Ethyl 3-(4-[2-[3-carboxy-5-phenyl-2(4-fluorophenyl)pyrrol-1-yl)ethoxy]phenyl-2-ethoxy propanoate;

(−) Ethyl 3-(4-[2-[3-carboxy-5-phenyl-2(4-fluorophenyl)pyrrol-1-yl)ethoxy]phenyl-2-ethoxy propanoate;

(±) Ethyl 3-{4-[2-(2-methylthiopyrrol-1-yl)ethoxy]phenyl}-2-ethoxypropanoate;

(+) Ethyl 3-{4-[2-(2-methylthiopyrrol-1-yl)ethoxy]phenyl}-2-ethoxypropanoate;

(−) Ethyl 3-{4-[2-(2-methylthiopyrrol-1-yl)ethoxy]phenyl}-2-ethoxypropanoate;

Ethyl (E/Z) 3-{4-[2-(5-methyl-2-phenyl-pyrrol-1-yl)ethoxy]phenyl}-2-ethoxyprop-2-enenoate;

Ethyl (Z) 3-{4-(2-(5-methyl-2-phenyl-pyrrol-1-yl)ethoxy]phenyl{-2-ethoxyprop-2-enenoate;

Ethyl (E) 3-{4-[2-(5-methyl-2-phenyl-pyrrol-1-yl)ethoxy]phenyl{-2-ethoxyprop-2-enenoate; [(2R)-N(1 S)]-2-Ethoxy-3-{4-112-(5-methyl-2-phenylpyrrol-1-yl)ethoxy)phenyl}-N-(2-hydroxy-1- phenylethyl) propanamide

[(25)-N(1 S)1-2-Ethoxy-3-(4-[2-(5-methyl-2-phenylpyrrol-1-yl)ethoxy]phenyl}-N-(2-hydroxy-1-phenylethyl) propanamide (±) 3-{4-[2-(~pyrrol-1-yl)ethoxy]phenyl}-2-ethoxypropanoic acid and its pharmaceutically acceptable salts;

(+) 3-(4-[2-(pyrrol-1-yl)ethoxy]phenyl}-2-ethoxypropanoic acid and its pharmaceutically acceptable salts;

(−) 3-(4-[2-(pyrrol-1-yl)ethoxy]phenyl}-2-ethoxypropanoic acid and its pharmaceutically acceptable salts;

(±) 3-(4-[2-(2,5-dimethylpyrrol-1-yl)ethoxy]phenyl}-2-ethoxypropanoic acid and its pharmaceutically acceptable salts;

(+) 3(4-[2-(2,5-dimethylpyrrol-1-yl)ethoxy]phenyl}-2-ethoxypropanoic acid and its pharmaceutically acceptable salts;

(−) 3-(4-[2-(2,5-dimethylpyrrol-1-yl)ethoxy]phenyl}-2-ethoxypropanoic acid and its pharmaceutically acceptable salts;

(±) 3-(4-[2-(2,4-dimethylpyrrol-1-yl)ethoxy]phenyl}-2-ethoxypropanoic acid and its pharmaceutically acceptable salts;

(+) 3-(4-[2-(2,4-dimethylpyrrol-1-yl)ethoxy]phenyl}-2-ethoxypropanoic acid and its pharmaceutically acceptable salts;

(−) 3-(4-[2-(2,4-dimethylpyrrol-1-yl)ethoxy]phenyl}-2-ethoxypropanoic acid and its pharmaceutically acceptable salts;

(±) 3-(4-[2-(2-ethylpyrrol-1-yl)ethoxy]phenyl}-2-ethoxypropanoic, acid and its pharmaceutically acceptable salts;

(+) 3-(4-[2-(2-ethylpyrrol-1-yl)ethoxy]phenyl}-2-ethoxypropanoic, acid and its pharmaceutically acceptable salts;

(−) 3-(4-[2-(2-ethylpyrrol-1-yl)ethoxy]phenyl}-2-ethoxypropanoic, acid and its pharmaceutically acceptable salts;

(±) 3-(4-f2-(2-formylpyrrol-1-yl)ethoxy]phenyl}-2-ethoxypropanoic acid and its pharmaceutically acceptable salts;

(+) 3-(4-[2-(2-formylpyrrol-1-yl)ethoxy]phenyl}-2-ethoxypropanoic acid and its pharmaceutically acceptable salts;

(−) 3-(4-[2-(2-formylpyrrol-1-yl)ethoxy]phenyl}-2-ethoxypropanoic acid and its pharmaceutically acceptable salts;

(±) 3-(4-[2-(2-acetylpyrrol-1-yl)ethoxy]phenyl}-2-ethoxypropanoic acid and its pharmaceutically acceptable salts;

(+) 3-(4-[2-(2-acetylpyrrol-1-yl)ethoxy]phenyl}-2-ethoxypropanoic acid and its pharmaceutically acceptable salts;

(−) 3-(4-[2-(2-acetylpyrrol-1-yl)ethoxy]phenyl}-2-ethoxypropanoic acid and its pharmaceutically acceptable salts;

(±) 3-(4[-(2-ethyl-5-methylpyrrol-1-yl)ethoxy]phenyl)-2-ethoxypropanoic acid and its pharmaceutically acceptable salts;

(+) 3-(4[-(2-ethyl-5-methylpyrrol-1-yl)ethoxy]phenyl)-2-ethoxypropanoic acid and its pharmaceutically acceptable salts;

(−) 3-(4[-(2-ethyl-5-methylpyrrol-1-yl)ethoxy]phenyl)-2-ethoxypropanoic acid and its pharmaceutically acceptable salts;

(±) 3-{4-[2-(5-methyl-2-propylpyrrol-1-yl)ethoxy]phenyl}-2-ethoxypropanoic acid and its pharmaceutically acceptable salts;

(+) 3-(4-[2-(5-methyl-2-propylpyrrol-1-yl)ethoxy]phenyl}-2-ethoxypropanoic acid and its pharmaceutically acceptable salts;

(−) 3-(4-[2-(5-methyl-2-propylpyrrol-1-yl)ethoxy]phenyl}-2-ethoxypropanoic acid and its pharmaceutically acceptable salts;

(±) 3-(4-[2-(5-methyl-2-n-butylpyrrol-1-yl)ethoxy]phenyl}-2-ethoxypropanoic-acid and its pharmaceutically acceptable salts;

(+) 3-(4-[2-(5-methyl-2-n-butylpyrrol-1-yl)ethoxy]phenyl}-2-ethoxypropanoic-acid and its pharmaceutically acceptable salts;

(−) 3-(4-[2-(5-methyl-2-n-butylpyrrol-1-yl)ethoxy]phenyl}-2-ethoxypropanoic-acid and its pharmaceutically acceptable salts;

(±) 3-(4-[2-(5-methyl-2-phenylpyrrol-1-yl)ethoxy]phenyl}-2-ethoxypropanoic-acid and its pharmaceutically acceptable salts;

(+) 3-(4-[2-(5-methyl-2-phenylpyrrol-1-yl)ethoxy]phenyl}-2-ethoxypropanoic-acid and its pharmaceutically acceptable salts;

(−) 3-(4-[2-(5-methyl-2-phenylpyrrol-1-yl)ethoxy]phenyl}-2-ethoxypropanoic-acid and its pharmaceutically acceptable salts;

(±) 3-(4-[2-(5-methyl-2-phenylpyrrol-1-yl)ethoxy]phenyl}-2-ethoxypropanoic-acid and its pharmaceutically acceptable salts;

(+) 3-(4-[2-(5-methyl-2-phenylpyrrol-1-yl)ethoxy]phenyl}-2-ethoxypropanoic-acid and its pharmaceutically acceptable salts;

(−) 3-(4-[2-(5-methyl-2-phenylpyrrol-1-yl)ethoxy]phenyl}-2-ethoxypropanoic-acid and its pharmaceutically acceptable salts;

(±) 3-(4-[2-(5-methyl-2-methylphenyl)pyrrol-1-yl)ethoxy]phenyl}-2-propoxypropanoic-acid and its pharmaceutically acceptable salts;

(+) 3-(4-[2-(5-methyl-2-methylphenyl)pyrrol-1-yl)ethoxy]phenyl}-2-propoxypropanoic-acid and its pharmaceutically acceptable salts;

(−) 3-(4-[2-(5-methyl-2-methylphenyl)pyrrol-1-yl)ethoxy]phenyl}-2-propoxypropanoic-acid and its pharmaceutically acceptable salts;

(±) 3-(4-[2-(5-methyl-3-phenylpyrrol-1-yl)ethoxy]phenyl}-2-ethoxypropanoic acid and its pharmaceutically acceptable salts;

(+) 3-(4-[2-(5-methyl-3-phenylpyrrol-1-yl)ethoxy]phenyl}-2-ethoxypropanoic acid and its pharmaceutically acceptable salts;

(−) 3-(4-[2-(5-methyl-3-phenylpyrrol-1-yl)ethoxy]phenyl}-2-ethoxypropanoic acid and its pharmaceutically acceptable salts;

(±) 3-(4-[2-(5-methyl-2-(4-methylphenyl)pyrrol-1-yl)ethoxy]phenyl}-2-ethoxypropanoic acid and its pharmaceutically acceptable salts;

(+) 3-(4-[2-(5-methyl-2-(4-methylphenyl)pyrrol-1-yl)ethoxy]phenyl}-2-ethoxypropanoic acid and its pharmaceutically acceptable salts;

(−) 3-(4-[2-(5-methyl-2-(4-methylphenyl)pyrrol-1-yl)ethoxy]phenyl}-2-ethoxypropanoic acid and its pharmaceutically acceptable salts;

(±) 3-(4-[2-(5-methyl-2-(3-methylphenyl)pyrrol-1-yl)ethoxy]phenyl}-2-ethoxypropanoic acid and its pharmaceutically acceptable salts;

(+) 3-(4-[2-(5-methyl-2-(3-methylphenyl)pyrrol-1-yl)ethoxy]phenyl}-2-ethoxypropanoic acid and its pharmaceutically acceptable salts;

(−) 3-(4-[2-(5-methyl-2-(3-methylphenyl)pyrrol-1-yl)ethoxy]phenyl}-2-ethoxypropanoic acid and its pharmaceutically acceptable salts;

(±) 3-(4-[2-(5-methyl-2-(2-methylphenyl)pyrrol-1-yl)ethoxy]phenyl}-2-ethoxypropanoic acid and its pharmaceutically acceptable salts;

(+) 3-(4-[2-(5-methyl-2-(2-methylphenyl)pyrrol-1-yl)ethoxy]phenyl}-2-ethoxypropanoic acid and its pharmaceutically acceptable salts;

(−) 3-(4-[2-(5-methyl-2-(2-methylphenyl)pyrrol-1-yl)ethoxy]phenyl}-2-ethoxypropanoic acid and its pharmaceutically acceptable salts;

(±) 3-(4-[2-(5-methyl-2-(4-methylphenyl)pyrrol-1-yl)ethoxy]phenyl}-2-ethoxypropanoic acid and its pharmaceutically acceptable salts;

(+) 3-(4-[2-(5-methyl-2-(4-methylphenyl)pyrrol-1-yl)ethoxy]phenyl}-2-ethoxypropanoic acid and its pharmaceutically acceptable salts;

(−) 3-(4-[2-(5-methyl-2-(4-methylphenyl)pyrrol-1-yl)ethoxy]phenyl}-2-ethoxypropanoic acid and its pharmaceutically acceptable salts;

(±) 3-(4-[2-(5-methyl-2-(4-bromophenyl)pyrrol-1-yl)ethoxy]phenyl}-2-ethoxypropanoic acid and its pharmaceutically acceptable salts;

(+) 3-(4-[2-(5-methyl-2-(4-bromophenyl)pyrrol-1-yl)ethoxy]phenyl}-2-ethoxypropanoic acid and its pharmaceutically acceptable salts;

(−) 3-(4-[2-(5-methyl-2-(4-bromophenyl)pyrrol-1-yl)ethoxy]phenyl}-2-ethoxypropanoic acid and its pharmaceutically acceptable salts;

(±) 3-(4-[2-(5-methyl-2-(4-fluorophenyl)pyrrol-1-yl)ethoxy]phenyl}-2-ethoxypropanoic acid and its pharmaceutically acceptable salts;

(+) 3-(4-[2-(5-methyl-2-(4-fluorophenyl)pyrrol-1-yl)ethoxy]phenyl}-2-ethoxypropanoic acid and its pharmaceutically acceptable salts;

(−) 3-(4-[2-(5-methyl-2-(4-fluorophenyl)pyrrol-1-yl)ethoxy]phenyl}-2-ethoxypropanoic acid and its pharmaceutically acceptable salts;

(±) 3-(4-[2-(5-methyl-2-(4-chlorophenyl)pyrrol-1-yl)ethoxyjphenyl}-2-ethoxypropanoic acid and its pharmaceutically acceptable salts;

(+) 3-(4-[2-(5-methyl-2-(4-chlorophenyl)pyrrol-1-yl)ethoxy]phenyl}-2-ethoxypropanoic acid and its pharmaceutically acceptable salts;

(−) 3-(4-[2-(5-methyl-2-(4-chlorophenyl)pyrrol-1-yl)ethoxy]phenyl}-2-ethoxypropanoic acid and its pharmaceutically acceptable salts;

(±) 3-(4-[2-(4-methyl-2-phenylpyrrol-1-yl)ethoxy]phenyl}-2-ethoxypropanoic acid and its pharmaceutically acceptable salts;

(+) 3-(4-[2-(4-methyl-2-phenylpyrrol-1-yl)ethoxy]phenyl}-2-ethoxypropanoic acid and its pharmaceutically acceptable salts;

(−) 3-(4-[2-(4-methyl-2-phenylpyrrol-1-yl)ethoxy]phenyl}-2-ethoxypropanoic acid and its pharmaceutically acceptable salts;

(±) 3-{4-[2-(5-methyl-2,3-diphenylpyrrol-1-yl)ethoxy]phenyl}-2-ethoxypropanoic acid and its pharmaceutically acceptable salts;

(+) 3-{4-[2-(5-methyl-2,3-diphenylpyrrol-1-yl)ethoxy]phenyl}-2-ethoxypropanoic acid and its pharmaceutically acceptable salts;

(−) 3-{4-[2-(5-methyl-2,3-diphenylpyrrol-1-yl)ethoxy]phenyl}-2-ethoxypropanoic acid and its pharmaceutically acceptable salts;

(±) 3-(4-[2-(2-isopropyl-5-methylpyrrol-1-yl)ethoxy]phenyl}-2-ethoxypropanoic and its pharmaceutically acceptable salts;

(+) 3-(4-[2-(2-isopropyl-5-methylpyrrol-1-yl)ethoxy]phenyl}-2-ethoxypropanoic and its pharmaceutically acceptable salts;

(−) 3-(4-[2-(2-isopropyl-5-methylpyrrol-1-yl)ethoxy]phenyl}-2-ethoxypropanoic and its pharmaceutically acceptable salts;

(±) 3-{4-[2-(2,5-diisopropylpyrrol-1-yl)ethoxy]phenyl}-2-ethoxypropanoic acid and its pharmaceutically acceptable salts;

(+) 3-{4-[2-(2,5-diisopropylpyrrol-1-yl)ethoxy]phenyl}-2-ethoxypropanoic acid and its pharmaceutically acceptable salts;

(−) 3-{4-[2-(2,5-diisopropylpyrrol-1-yl)ethoxy]phenyl}-2-ethoxypropanoic acid and its pharmaceutically acceptable salts;

(±) 3-{4-[2-(5-isopropyl-2-phenylpyrrol-1-yl)ethoxy]phenyl}-2-ethoxypropanoic acid and its pharmaceutically acceptable salts;

(+) 3-{4-[2-(5-isopropyl-2-phenylpyrrol-1-yl)ethoxy]phenyl}-2-ethoxypropanoic acid and its pharmaceutically acceptable salts;

(−) 3-{4-[2-(5-isopropyl-2-phenylpyrrol-1-yl)ethoxy]phenyl}-2-ethoxypropanoic acid and its pharmaceutically acceptable salts;

(±) 3-(4-[2-(2,5-diisopropyl-3-phenylpyrrol-1-yl)ethoxy]phenyl}-2-ethoxypropanoic acid and its pharmaceutically acceptable salts;

(+) 3-(4-[2-(2,5-diisopropyl-3-phenylpyrrol-1-yl)ethoxy]phenyl}-2-ethoxypropanoic acid and its pharmaceutically acceptable salts;

(−) 3-(4-[2-(2,5-diisopropyl-3-phenylpyrrol-1-yl)ethoxy]phenyl}-2-ethoxypropanoic acid and its pharmaceutically acceptable salts;

(±) 3-{4-[2-(5-isopropyl-2-(4-methoxyphenyl)pyrrol-1-yl]ethoxy}phenyl)-2-ethoxypropanoic acid and its pharmaceutically acceptable salts;

(+) 3-{4-[2-(5-isopropyl-2-(4-methoxyphenyl)pyrrol-1-ylethoxy)phenyl]-2-ethoxypropanoic acid and its pharmaceutically acceptable salts;

(−) 3-{4-[2-(5-isopropyl-2-(4-methoxyphenyl)pyrrol-1-yl]ethoxy}phenyl)-2-ethoxypropanoic acid and its pharmaceutically acceptable salts;

(±) 3-(4-(2-[2-(4-fluorophenyl)-5-isopropylpyrrol-1-yl]ethoxy}phenyl)-2-ethoxypropanoic acid and its pharmaceutically acceptable salts;

(+) 3-(4-(2-[2-(4-fluorophenyl)-5-isopropylpyrrol-1-yl]ethoxy}phenyl)-2-ethoxypropanoic acid and its pharmaceutically acceptable salts;

(−) 3-(4-(2-[2-(4-fluorophenyl)-5-isopropylpyrrol-1-yl]ethoxy}phenyl)-2-ethoxypropanoic acid and its pharmaceutically acceptable salts;

(±) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(+) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(−) 3-(4-(2-[2-(4-fluorophenyl)-5-isopropyl-3-phenylpyrrol-1-yl]ethoxy)phenyl)-2-ethoxypropanoic acid and its pharmaceutically acceptable salts;

(±) 3-(4-(2-[2-(4-fluorophenyl)-5-isopropyl-4-phenylcarbamoylpyrrol-1-yl]ethoxy}phenyl)-2- ethoxypropanoic acid and its pharmaceutically acceptable salts;

(+) 3-(4-(2-[2-(4-fluorophenyl)-5-isopropyl-4-phenylcarbamoylpyrrol-1-yl]ethoxy}phenyl)-2- ethoxypropanoic acid and its pharmaceutically acceptable salts;

(−) 3-(4-(2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(±) 3-(4-(2-[2-(4-fluorophenyl)-5-isopropyl-3-phenyl-4-phenylcarbamoylpyrrol-1-yl]ethoxy)phenyl)-2- ethoxypropanoic acid its pharmaceutically acceptable salts;

(+) 3-(4-(2-[2-(4-fluorophenyl)-5-isopropyl-3-phenyl-4-phenylcarbamoylpyrrol-1-yl]ethoxy)phenyl)-2- ethoxypropanoic acid its pharmaceutically acceptable salts;

(−) 3-(4-(2-[2-(4-fluorophenyl)-5-isopropyl-3-phenyl-4-phenylcarbamoylpyrrol-1-yl]ethoxy)phenyl)-2-ethoxypropanoic acid its pharmaceutically acceptable salts;

(±) 3-(4-(3-[2-(4-fluorophenyl)-5-isopropyl-3-phenyl-4-phenylcarbamoylpyrrol-1-yl]propoxy{phenyl)-2-ethoxypropanoic acid its pharmaceutically acceptable salts;

(+) 3-(4-(3-[2-(4-fluorophenyl)-5-isopropyl-3-phenyl-4-phenylcarbamoylpyrrol-1-yl]propoxy{phenyl).2-ethoxypropanoic acid its pharmaceutically acceptable salts;

(−) 3-(4-(3-[2-(4-fluorophenyl)-5-isopropyl-3-phenyl-4-phenylcarbamoylpyrrol-1-yl]propoxy{phenyl)-2-ethoxypropanoic acid its pharmaceutically acceptable salts;

(±) 3-(4-(2-[(2-(4-fluorophenyl)-5-phenylpyrrol-1-yl]ethoxy)phenyl)-2-ethoxypropanoic acid and its pharmaceutically acceptable salts;

(+) 3-(4-(2-[(2-(4-fluorophenyl)-5-phenylpyrrol-1-yl]ethoxy}phenyl)-2-ethoxypropanoic acid and its pharmaceutically acceptable salts;

(−) 3-(4-(2-[(2-(4-fluorophenyl)-5-phenylpyrrol-1-yl]ethoxy}phenyl)-2-ethoxypropanoic acid and its pharmaceutically acceptable salts;

(±) 3-[4-[2-(3-carboxy-5-phenyl-2-(4-fluorophenyl)pyrrol-1-yl)ethoxy]phenyl)-2-ethoxypropanoic acid and its pharmaceutically acceptable salts;

(+) 3-[4-[2-(3-carboxy-5-phenyl-2-(4-fluorophenyl)pyrrol-1-yl)ethoxy]phenyl)-2-ethoxypropanoic acid and its pharmaceutically acceptable salts;

(−) 3-[4-[2-(3-carboxy-5-phenyl-2-(4-fluorophenyl)pyrrol-1-yl)ethoxy]phenyl)-2-ethoxypropanoic acid and its pharmaceutically acceptable salts;

(±) 3-{4-[2-(2-methylthiopyrrol-1-yl)ethoxyjphenyl}-2-ethoxypropanoic acid and its pharmaceutically acceptable salts;

(+) 3-{4-[2-(2-methylthiopyrrol-1-yl)ethoxy]phenyl}-2-ethoxypropanoic acid and its pharmaceutically acceptable salts;

(−) 3-(4-[2-(2-methylthiopyrrol-1-yl)ethoxy]phenyl}-2-ethoxypropanoic acid and its pharmaceutically acceptable salts;

(E/Z) 3-(4-[2-(5-methyl-2-phenylpyrrol-1-yl)ethoxy]phenyl}-2-ethoxyprop-2-enoic acid and its pharmaceutically acceptable salts;

(E) 3-(4-[2-(5-methyl-2-phenylpyrrol-1-yl)ethoxy]phenyl}-2-ethoxyprop-2-enoic acid and its pharmaceutically acceptable salts;

(Z) 3-(4-[2-(5-methyl-2-phenylpyrrol-1-yl)ethoxy]phenyl}-2-ethoxyprop-2-enoic acid and its pharmaceutically acceptable salts.

15. A compound according to claim 14, which is selected from: (±) 3-(4-[2(pyrrol-1 -yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(+) 3-(4-[2(pyrrol-1 -yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-(4-[2(pyrrol-1 -yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(±) 3-{4-[2(2,5-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2(2,5-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2(2,5-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2(2,4-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2(2,4-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2(2,4-dimethylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(2-ethylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(2-ethylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(2-ethylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(2-formylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(2-formylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(2-formylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(2-acetypyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(2-acetypyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(2-acetypyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(2-ethyl-5-methylpyrrol-1-yl)ethoxyjphenyl}-2-ethoxypropanoic acid, and its Li, Na, K, Ca, Image Page 18 Mg, lysine, arginine, guanidine, tromethamine, diethanolamine, choline, ammonium, substituted ammonium salts or aluminium salts;

(+) 3-{4-[2-(2-ethyl-5-methylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3(4-[2-(2-ethyl-5-methylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-propylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-propylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-propylpyrrol-1-yl)ethoxy]phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-n-butylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-n-butylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-n-butylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-phenylpyrrol-1-yl)ethoxy]phenyl}-2-methoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-phenylpyrrol-1-yl)ethoxy]phenyl}-2-methoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-phenylpyrrol-1-yl)ethoxy]phenyl}-2-methoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(4-methylphenyl)pyrrol-1-yl)ethoxy]phenyl}-2-propoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(4-methylphenyl)pyrrol-1-yl)ethoxyjphenyl}-2-propoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(4-methylphenyl)pyrrol-1-yl)ethoxy]phenyl}-2-propoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(5-methyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(4-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline. ammonium, substituted ammonium salts or aluminium salts;

(+) 3-(4-[2-(5-methyl-2-(4-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline. ammonium, substituted ammonium salts or aluminium salts;

(−) 3-(4-[2-(5-methyl-2-(4-methylphenyl)pyrrol-1-yl)ethoxy]phenyl}-2-ethoxypanoic acid, and its Li, Na, K, Ca, Mg, lysine, arginine, guanidine, tromethamine, diethanolamine, choline. ammonium, substituted ammonium salts or aluminium salts;

(±) 3-(4-[2-(5-methyl-2-(3-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(3-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(3-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(2-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(2-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(2-methylphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(5-methyl-2-(4-methoxyphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[-(5-methyl-2-(4-methoxyphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(4-methoxyphenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(4-bromophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(4-bromophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(4-bromophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(4-fluorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(4-fluorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-[2-(5-methyl-2-(4-fluorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-[2-(5-methyl-2-(4-chlorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-[2-(5-methyl-2-(4-chlorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(5-methyl-2-(4-chlorophenyl)pyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(4-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2-(4-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(4-methyl-2-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(5-methyl-2,3-diphenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2-(5-methyl-2,3-diphenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(5-methyl-2,3-diphenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-{2-[5-isopropyl-2-(4-methoxyphenyl)pyrrol-1-yl]ethoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2-(2-isopropyl-5-methylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(2-isopropyl-5-methylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[(2,5-diisopropylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[(2,5-diisopropylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[(2,5-diisopropylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(5-isopropyl-2-phenylpyrrol-1-yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(+) 3-{4-[2-(5-isopropyl-2-phenylpyrrol-1-yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-{4-[2-(5-isopropyl-2-phenylpyrrol-1-yl)ethoxy]phenyl}-2-ethoxypropanoic acid and its Li, Na, K, Ca, Mg, lysine, arginine, guanidine, tromethamine, diethanolamine, choline, ammonium, substituted ammonium salts or aluminium salts;

(±) 3-{4-[2-(2,5-diisopropyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(30) 3-{4-[2-(2,5-diisopropyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(2,5-diisopropyl-3-phenylpyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-{2-[5-isopropyl-2-(4-methoxyphenyl)pyrrol-1-yl]ethoxy}phenyl)-2-ethoxypropanoic acid, and its Li, Na, K, Ca, Mg, lysine, arginine, guanidine, tromethamine, diethanolamine, choline, ammomum, substituted ammonium salts or aluminium salts;

(+) 3-(4-{2-[5-isopropyl-2-(4-methoxyphenyl)pyrrol-1-yl]ethoxy}phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-(4-{2-[5-isopropyl-2-(4-methoxyphenyl)pyrrol-1-yl]ethoxy}phenyl)-2-ethoxypropan0k acid and its Li, Na, K, Ca, Mg, lysine, arginine, guanidine, tromethamine, diethanolamine, choline, ammonium, substituted ammonium salts or aluminium salts;

(±) 3-(4-{2-[2-(4-fluorophenyl)-5-isopropylpyrrol-1-yl]ethoxy}phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(+) 3-(4-{2-[2-(4-fluorophenyl)-5-isopropylpyrrol-1-yl]ethoxy}phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-(4-{2-[2-(4-fluorophenyl)-5-isopropylpyrrol-1-yl]ethoxy}phenyl>2-ethoxypropanoic acid and its Li, Na, K, Ca, Mg, lysine, arginine, guanidine, tromethamine, diethanolamine, choline, ammonium, substituted ammonium salts or aluminium salts;

(±) 3-(4-(2-[2-(4-fluorophenyl)-5-isopropyl-3-phenylpyrrol-1-yl]ethoxy)phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(+) 3-(4-(2-[2-(4-fluorophenyl)-5-isopropyl-3-phenylpyrrol-1-yl]ethoxy)phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-(4-(2-[2-(4-fluorophenyl)-5-isopropyl-3-phenylpyrrol-1-yl]ethoxy)phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(±) 3-(4-{2-[2-4-fluorophenyl)-5-isopropyl-4-phenylcarbamoylpyrrol-1-yl]ethoxy}phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(+) 3-(4-{2-[2-(4-fluorophenyl)-5-isopropyl-4-phenylcarbamoylpyrrol-1-yl]ethoxy}phenyl)-2-ethoxypropanoic acid and its Li, Na, K, Ca, Mg, lysine, arginine, guanidine, tromethamine, diethanolamine, choline, ammonium, substituted ammonium salts or aluminium salts;

(−) 3-(4-{2-[2-(4-fluorophenyl)-5-isopropyl-4-phenylcarbamoylpyrrol-1-yl]ethoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-{2-[2-(4-fluorophenyl)-5-isopropyl-3-phenyl-4-phenylcarbamoylpyrrol-1-yl]ethoxy}phenyl)-2-ethoxypropanoic acid, and its Li, Na, K, Ca, Mg, lysine, arginine, guanidine , tromethamine, diethanolamine, choline, ammonium, substituted ammonium salts or aluminium salts;

(+) 3-(4-{2-[2-(4-fluorophenyl)-5-isopropyl-3-phenyl-4-phenylcarbamoylpyrrol-1-yl]ethoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-{2-[2-(4-fluorophenyl)-5-isopropyl-3-phenyl-4-phenylcarbamoylpyrrol-1-yl]ethoxy}phenyl)-2- ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-{3-[2-(4-fluorophenyl)-5-isopropyl-3-phenyl-4-phenylcarbamoylpyrrol-1- yl]propoxy}phenyl) 2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-{3-[2-(4-fluorophenyl)-5-isopropyl-3-phenyl-4-phenylcarbamoylpyrrol-1-yl]propoxy}phenyl). 2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-{3-[2-(4-fluorophenyl)-5-isopropyl-3-phenyl-4-phenylcarbamoylpyrrol-1-yl]propoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-(4-(2-[2-(4-fluorophenyl)-5-phenylpyrrol-1-yl] ethoxy)phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-(4-{2-[2-(4-fluorophenyl)-5-phenylpyrrol-1-yl] ethoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-(4-{2-[2-(4-fluorophenyl)-5-phenylpyrrol-1-yl] ethoxy}phenyl)-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(3-carboxy-5-phenyl-2-(4-fluorophenyl) pyrrol-1-yl)ethoxy]phenyl]-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2-(3-carboxy-5-phenyl-2-(4-fluorophenyl) pyrrol-1-yl)ethoxy]phenyl]-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(3-carboxy-5-phenyl-2-(4-fluorophenyl) pyrrol-1-yl)ethoxy]phenyl]-2-ethoxypropanoic acid, and its Li, Na, K, Ca, Mg, lysine, arginine, guanidine, tromethamine, diethanolamine, choline, ammonium, substituted ammonium salts or aluminium salts;

(±) 3-{4-[2-(2-methylthiopyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(+) 3-{4-[2-(2-methylthiopyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(−) 3-{4-[2-(2-methylthiopyrrol-1-yl)ethoxy]phenyl}-2-ethoxypropanoic acid, and its Li, Na, K, Ca, Mg, lysine, arginine, guanidine, tromethamine, diethanolamine, choline, ammonium, substituted ammonium salts or aluminium salts;

(E/Z) 3-{4-[2-(5-methyl-2-phenylpyrrol-1-yl)ethoxy] phenyl}-2-ethoxyprop-2-enoic acid, and its Li, Na, K, Ca, Mg, lysine, arginine, guanidine, tromethamine, diethanolamine, choline, ammonium, substituted ammonium salts or aluminium salts;

(E) 3-{4-[2-(5-methyl-2-phenylpyrrol-1-yl)ethoxy] phenyl}-2-ethoxyprop-2-enoic acid, and its Li, Na, K, Ca, Mg, lysine, arginine, guanidine, tromethamine, diethanolamine, choline, ammonium, substituted ammonium salts or aluminium salts;

(Z) 3-{4-[2-(5-methyl-2-phenylpyrrol-1-yl)ethoxy] phenyl}-2-ethoxyprop-2-enoic acid, and its Li, Na, K, Ca, Mg, lysine, arginine, guanidine, tromethamine, diethanolamine, choline, ammonium, substituted ammonium salts or aluminium salts.

16. A pharmaceutical composition, which comprises a compound as defined in claim 14, and a pharmaceutically acceptable carrier, diluents or excipients or solvate.

17. A pharmaceutical composition as claimed in claim 16, in the form of a tablet, capsule, powder, syrup, solution or suspension.

18. A pharmaceutical composition, which comprises a compound as defined in claim 15, and a pharmaceutically acceptable carrier, diluents or excipients or solvate.

19. A pharmaceutical composition as claimed in claim 18, in the form of a tablet, capsule, powder, syrup, solution or suspension.

20. A process for the preparation of a compound of formula (I)

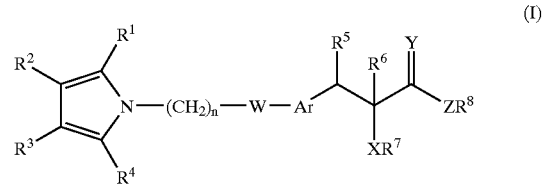

(I)

their tautomeric forms, their stereoisomers, their pharmaceutically acceptable salts, their pharmaceutically acceptable solvates, wherein one or more groups $R^1$, $R^2$, $R^3$, $R^4$ may be same or different and represent hydrogen, halogen, perhaloalkyl, hydroxy, thio, amino, nitro, cyano, formyl, amidino, guanidino, substituted or unsubstituted groups selected from linear or branched $(C_1-C_{12})$alkyl, linear or branched $(C_2-C_{12})$alkenyl, $(C_3-C_8)$cycloalkyl, $(C_3-C_8)$cycloalkenyl, bicycloalkyl, bicycloalkenyl, $(C_1-C_{12})$alkoxy, cyclo$(C_3-C_8)$alkoxy, aryl, aryloxy, aralkyl, ar$(C_1-C_{12})$ alkoxy, heterocyclyl, heteroaryl, heterocyclyl$(C_1-C_{12})$alkyl, heteroar$(C_1-C_{12})$alkyl, heteroaryloxy, heteroar$(C_1-C_{12})$ alkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, aminoalkyl, monoalkylaminoalkyl, dialkylaminoalkyl, alkoxyalkyl, aryloxyalkyl, aralkoxyalkyl, $(C_1-C_{12})$alkylthio, thio $(C_1-C_{12})$alkyl, arylthio, $(C_1-C_{12})$alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and derivatives of carboxylic acids selected from $CONH_2$, alkylaminocarbonyl, dialkylaminocarbonyl, arylaminocarbonyl; aralkylaminocarbonyl; heteroarylaminocarbonyl and heteroaralkylamino carbonyl groups; heterocyclylaminocarbonyl groups; sulfonic acid and its derivatives selected from $SO_2NH2$, $SO_2NHMe$, $SO_2NMe_2$, $SO_2NHCF_3$, $SO_2NHCO$ (C1-C6)alkyl, $SO_2NHCOaryl$ groups, phosphonic acid and its derivatives selected from $P(O)(QH)_2$, $P(O)(O\ C1-C6\ alkyl)_2$, $P(O)(O\ aryl)_2$, $P(O)(OH)\ (O\ C_1-C_6\ alkyl)$ groups; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, $(C_1-C_{12})$alkyl or aryl; Ar represents a substituted or unsubstituted divalent single or fused aromatic, heteroaromatic or heterocyclic group; R5 and $R^6$ represent both hydrogen or together represent a bond; R5 and R6 may also represent a hydroxy, $(C_1-C_{12})$alkyl. $(C_1-C_{12})$alkoxy, halogen, acyl, substituted or unsubstituted aralkyl group; X represents O or S; R7 represents hydrogen, perfluoro $(C_1-C_{12})$alkyl, substituted or unsubstituted groups selected from $(C_1-C_{12})$alkyl, cyclo$(C_1-C_{12})$alkyl, aryl, ar$(C_1-C_{12})$ alkyl, heteroaryl, heteroar$(C_1-C_{12})$alkyl, heterocyclyl, alkoxyalkyl, aryloxyalkyl, alkoxycarbonyl, aryloxycarbonyl, cycloalkyloxycarbonyl, alkylaminocarbonyl, arylaminocarbonyl, acyl groups; Y represents O or S; Z represents oxygen, sulfur or $NR^{10}$, where R10 represents hydrogen or substituted or unsubstituted groups selected from $(C_1-C_{12})$alkyl, aryl, ar$(C_1-C_{12})$alkyl, hydroxy$(C_1-C_{12})$alkyl, amino$(C_1-C_{12})$alkyl, heteroaryl, heteroar$(C_1-C_{12})$alkyl groups; R represents hydrogen, substituted or unsubstituted groups selected from $(C_1-C_{12})$ alkyl, aryl, ar$(C_1-C_{12})$alkyl, heteroaryl, heteroax$(C_1-C_{12})$ alkyl, heterocyclyl, heterocyclylalkyl, hydroxyalkyl, alkoxyalkyl, alkylaminoalkyl groups; R10 and R8 together may form a 5 or 6 membered substituted or unsubstituted cyclic ring structure containing carbon atoms or containing one or more heteroatoms selected from O, N and S which includes one or more of the following methods comprising;

a. reacting a compound of formula (1a), where all symbols are as defined above,

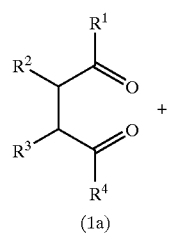

(1a)

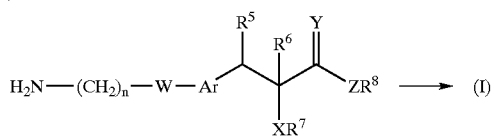

(1b)

with a compound of formula (1b) which may be racemic or chiral, where all symbols are as defined earlier to yield a compound of general formula (1);

b. reacting a compound of formula (1c), where $L^1$ represents a leaving group

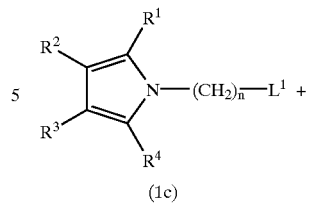

(1c)

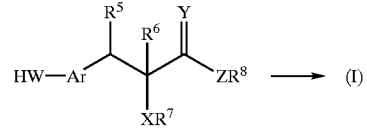

(1d)

with a compound of formula (Id) which may be racemic or chiral, where all symbols are as defined earlier to yield a compound of general formula (I); c. reacting the compound of formula (Ie),

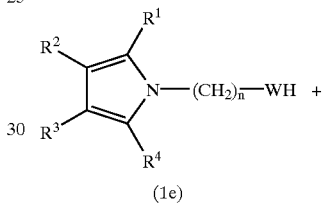

(1e)

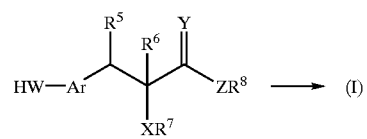

(1d)

with a compound of general formula (Id) which may be racemic or chiral, where W is particularly O or S and all other symbols are as defined earlier;

d. reacting a compound of formula (1f),

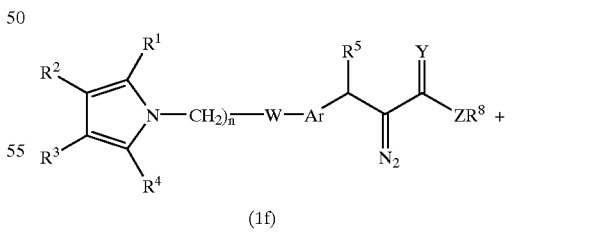

(1f)

(1g)

where all the symbols are as defined earlier with an alcohol of formula (1 g) wherein $R^7$ and X are as defined earlier, to produce a compound of formula (1), wherein all symbols are as defined earlier and R6 represents H;

e. reacting a compound of general formula (1h),

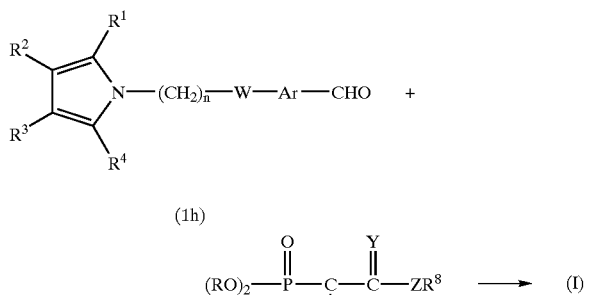

where all the symbols are as defined earlier, with a compound of formula (Ii) which may be chiral or racemic, where R represents ($C_1$–$C_8$) alkyl and other symbols are as defined earlier and to afford a compound of formula (I) where R5 and R6 together form a bond and other symbols are as defined earlier and; and for reacting a compound of general formula (1h),

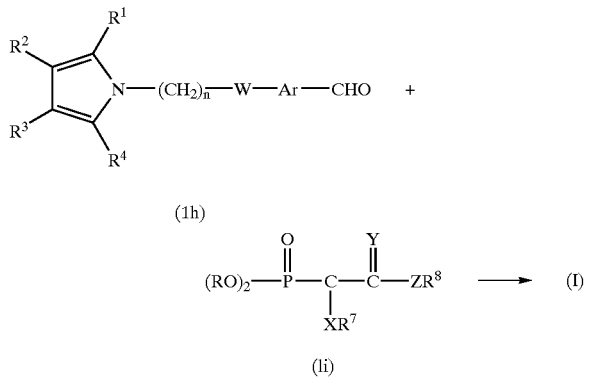

where all the symbols are as defined earlier, with a compound of formula (Ii) which may be chiral or racemic, where all the symbols are as defined earlier and R represents (C1-C8) alkyl to afford a compound of formula (I) wherein all symbols are as defined earlier and R5 and $R^6$ together form a bond which is reduction of the double bond formed together by R5 and $R^6$.

21. A process for converting an ester of the general formula (I) to a corresponding acid form and preparing a pharmaceutically acceptable salt and-or a pharmaceutically acceptable solvate thereof, comprising carrying out one or more of the following optional steps:

i. hydrolyzing a compound of formula (I),

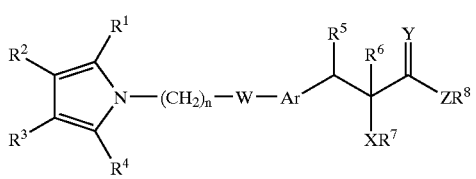

their tautomeric forms, their stereoisomers, wherein one or more groups $R^1$, $R^2$, $R^3$, $R^4$ may be the same or different and represent hydrogen, halogen, perhaloalkyl, hydroxy, thio, amino, nitro, cyano, formyl, amidino, guanidino. substituted or unsubstituted groups selected from linear or branched ($C_1$–$C_{12}$)alkyl, linear or branched ($C_2$–$C_{12}$)alkenyl. ($C_3$–$C_8$)cycloalkyl, ($C_3$–$C_7$)cycloalkenyl, bicycloalkyl, bicycloalkenyl, ($C_1$–$C_{12}$)alkoxy, cyclo($C_3$–$C_8$)alkoxy, aryl, aryloxy, aralkyl, ar($C_1$–$C_{12}$)alkoxy, heterocyclyl, heteroaryl, heterocyclyl($C_1$–$C_{12}$)alkyl, heteroar($C_1$–$C_{12}$)alkyl, heteroaryloxy, heteroar($C_1$–$C_{12}$)alkoxy, heterocyclyloxy, heterocyclylalkyloxy, acyl, acyloxy, acylamino, monoalkylamino, dialkylamino, arylamino, aralkylamino, alkoxycarbonyl, aryloxycarbonyl, aralkoxycarbonyl, heterocyclylalkoxycarbonyl, heteroaryloxycarbonyl, heteroaralkoxycarbonyl, heterocyclyloxycarbonyl, hydroxyalkyl, aminoalkyl, monoalkylaminoalkyl, dialkylaminoalkyl, alkoxyalkyl, aryloxyalkyl, aralkoxyalkyl, ($C_1$–$C_{12}$)alkylthio, thio($C_1$–$C_{12}$)alkyl, arylthio, ($C_1$–$C_{12}$)alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxylamino, derivatives of sulfenyl and sulfonyl groups, carboxylic acid and derivatives of carboxylic acids selected from $CONH_2$, alkylaminocarbonyl, dialkylaminocarbonyl, arylaminocarbonyl; aralkylaminocarbonyl; heteroarylaminocarbonyl and heteroaralkylamino carbonyl groups; heterocyclylaminocarbonyl groups; sulfonic acid and its derivatives selected from $SO_2NH2$, $SO_2NHMe$, $SO_2NMe_2$, $SO_2NHCF_3$, $SO_2NHCO$ ($C_1$–$C_6$)alkyl, $SO_2NHCO$aryl groups, phosphonic acid and its derivatives selected from $P(O)(OH)_2$, $P(O)(O\ C_1$–$C_6$ alkyl)$_2$, $P(O)(O\ aryl)_2$, $P(O)(OH)$ (O $C_1$–$C_6$ alkyl) groups; or the adjacent groups $R^2$ and $R^3$ together may form a five or a six membered ring, optionally containing one or more double bonds and optionally containing one or more heteroatoms selected from O, N, or S; n is an integer ranging from 1 to 8; W represents O, S or $NR^9$ where $R^9$ represents hydrogen, ($C_1$–$C_{12}$)alkyl or aryl; Ar represents a substituted or unsubstituted divalent single or fused aromatic, heteroaromatic or heterocyclic group; $R^5$ and $R^6$ represent both hydrogen or together represent a bond; R5 and R6 may also represent a hydroxy, ($C_1$–$C_{12}$)alkyl, ($C_1$–$C_{12}$)alkoxy, halogen, acyl, substituted or unsubstituted aralkyl group; X represents O or S; R7 represents hydrogen, perfluoro ($C_1$–$C_{12}$)alkyl, substituted or unsubstituted groups selected from ($C_1$–$C_{12}$)alkyl, cyclo($C_1$–$C_{12}$)alkyl, aryl, ar($C_1$–$C_{12}$) alkyl, heteroaryl, heteroar($C_1$–$C_{12}$)alkyl, heterocyclyl, alkoxyalkyl, aryloxyalkyl, alkoxycarbonyl, aryloxycarbonyl, cycloalkyloxycarbonyl, alkylaminocarbonyl, arylaminocarbonyl, acyl groups; Y represents O or S; Z represents oxygen, sulfur or $NR^{10}$, where R10 represents hydrogen or substituted or unsubstituted groups selected from ($C_1$–$C_{12}$)alkyl, aryl, ar($C_1$–$C_{12}$)alkyl, hydroxy($C_1$–$C_{12}$)alkyl, amino($C_1$–$C_{12}$)alkyl, heteroaryl, heteroar($C_1$–$C_{12}$)alkyl groups; R8 represents hydrogen, substituted or unsubstituted groups selected from ($C_1$–$C_{12}$) alkyl, aryl, ar($C_1$–$C_{12}$)alkyl, heteroaryl, heteroar($C_1$–$C_{12}$) alkyl, heterocyclyl, heterocyclylalkyl, hydroxyalkyl, alkoxyalkyl, alkylaminoalkyl groups when Z represents sulfur or $NR^{10}$; while R8 represents substituted or unsubstituted groups selected from ($C_1$–$C_{12}$)alkyl, aryl, ar($C_1$–$C_{12}$)alkyl, heteroaryl, heteroar($C_1$–$C_{12}$)alkyl, heterocyclyl, heterocyclylalkyl, hydroxyalkyl, alkoxyalkyl, alkylaminoalkyl groups, when Z represents O; to a corresponding acid of compound of formula (I), where all symbols are as defined earlier and Y & Z represents oxygen and $R^8$represents hydrogen, by reacting the ester with an alkaline hydrolytic reagent comprising LiOH, NaOH, KOH, or Ca(OH)2;

ii. preparing a pharmaceutically acceptable salt of the acid compound of formula (1) and, optionally a pharmaceutically acceptable solvate thereof, by reacting Li, Na, K, Ca, Mg, lysine, arginine, guanidine, tromethamine, diethanolamine, choline, ammonium, substituted ammonium or aluminium with a corresponding base of the compound.

* * * * *